(12) United States Patent
Valentine

(10) Patent No.: US 10,660,824 B2
(45) Date of Patent: May 26, 2020

(54) DEVICES, SYSTEM AND METHOD TO CONTROL THE DELIVERY OF ORAL MEDICATIONS TO ENSURE THEY ARE EFFICACIOUS, TAKEN AS PRESCRIBED, AND TO AVOID UNWANTED SIDE EFFECTS

(71) Applicant: Edmund L. Valentine, Palm Beach Gardens, FL (US)

(72) Inventor: Edmund L. Valentine, Palm Beach Gardens, FL (US)

( * ) Notice: Subject to any disclaimer, the term of this patent is extended or adjusted under 35 U.S.C. 154(b) by 0 days.

(21) Appl. No.: 15/751,371

(22) PCT Filed: Aug. 11, 2016

(86) PCT No.: PCT/US2016/046491
§ 371 (c)(1),
(2) Date: Feb. 8, 2018

(87) PCT Pub. No.: WO2017/027673
PCT Pub. Date: Feb. 16, 2017

(65) Prior Publication Data
US 2018/0228695 A1   Aug. 16, 2018

Related U.S. Application Data

(60) Provisional application No. 62/252,966, filed on Nov. 9, 2015, provisional application No. 62/203,638, filed on Aug. 11, 2015.

(51) Int. Cl.
*A61J 7/04* (2006.01)
*G06F 19/00* (2018.01)
*G16H 20/13* (2018.01)

(52) U.S. Cl.
CPC ............ *A61J 7/0418* (2015.05); *A61J 7/049* (2015.05); *A61J 7/0445* (2015.05); *A61J 7/0481* (2013.01); *G06F 19/30* (2013.01); *G16H 20/13* (2018.01); *A61J 2200/30* (2013.01); *A61J 2200/72* (2013.01); *A61J 2205/30* (2013.01); *A61J 2205/60* (2013.01); *Y02A 90/26* (2018.01)

(58) Field of Classification Search
USPC ........................................................ 705/2, 3
See application file for complete search history.

(56) References Cited

U.S. PATENT DOCUMENTS

2006/0149156 A1* 7/2006 Cochran ............... A61B 5/0006
600/509
2006/0157491 A1* 7/2006 Whittle ................. A61J 7/0481
221/9

(Continued)

OTHER PUBLICATIONS

Defanti e Souza, Frank Roger, A descriptive study about the use of pillboxes by older adults, 2013, Health, vol. 5, No. 12A, 103-109 (Year: 2013).*

*Primary Examiner* — Aryan E Weisenfeld
*Assistant Examiner* — Joshua B Blanchette
(74) *Attorney, Agent, or Firm* — Mayer Brown LLP

(57) ABSTRACT

The present invention describes a novel system, drug delivery device, mobile App, drug specific drug dispensing algorithm, and method to improve medication safety and effectiveness via the utilization of drug specific algorithms to control drug dispensing, avoid drug mediated adverse events, ensure prescription persistence and promote prescription compliance on a cost-effective real-time basis.

28 Claims, 20 Drawing Sheets

(56) References Cited

U.S. PATENT DOCUMENTS

| | | | | |
|---|---|---|---|---|
| 2007/0185615 A1* | 8/2007 | Bossi | ................ | G06F 19/3462 |
| | | | | 700/244 |
| 2008/0119958 A1* | 5/2008 | Bear | ................ | A61J 7/0481 |
| | | | | 700/244 |
| 2011/0115620 A1* | 5/2011 | Myers | ................ | G07C 9/28 |
| | | | | 340/539.12 |
| 2013/0335213 A1* | 12/2013 | Sherony | ................ | G08G 1/167 |
| | | | | 340/439 |
| 2014/0041441 A1* | 2/2014 | Hayter | ................ | A61B 5/14532 |
| | | | | 73/61.43 |
| 2014/0276549 A1* | 9/2014 | Osorio | ................ | A61M 5/1723 |
| | | | | 604/503 |
| 2014/0340191 A1* | 11/2014 | Clark | ................ | G06F 19/3462 |
| | | | | 340/5.2 |
| 2016/0136054 A1* | 5/2016 | Bunker | ................ | A61J 7/0481 |
| | | | | 340/573.1 |

* cited by examiner

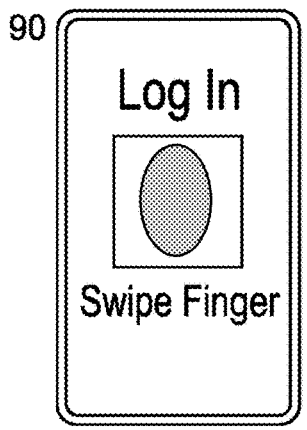
FIG. 3
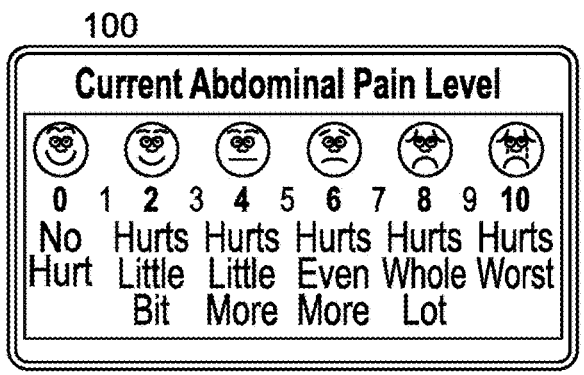
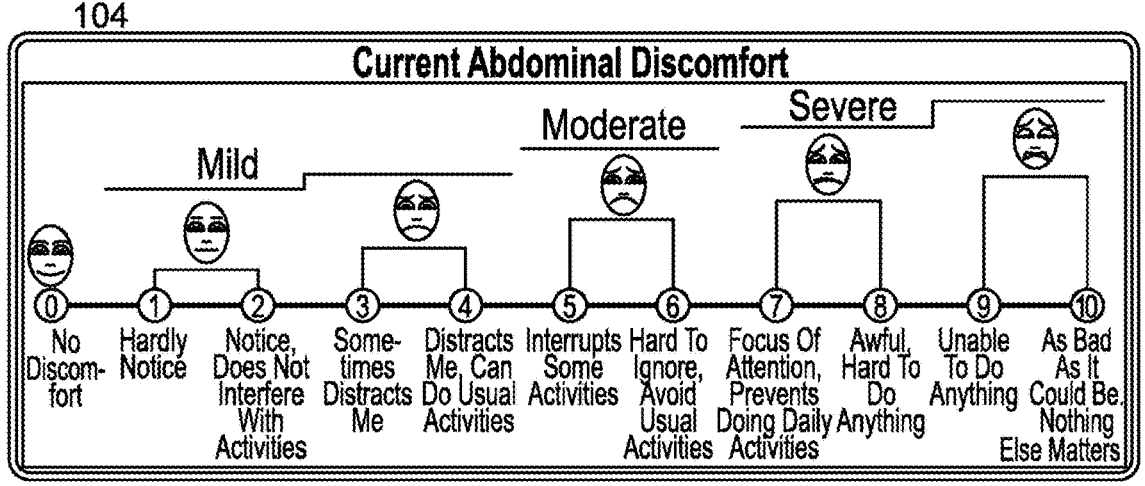
FIG. 4

Google's New Health Wearable

| 110 Wearable Monitoring Device | • Pulse<br>• heart rhythm<br>• skin temperature<br>• light exposure<br>• noise levels |
|---|---|

| 116 Hand-Held Diagnostic Device | • Temperature<br>• Blood Pressure<br>• Heart Rate<br>• Oximetry<br>• ECG<br>• HRV<br>• Stress<br>• UA |
|---|---|

| 112 Digital Scale | • Weight<br>• Fat<br>• Muscle<br>• Bone Mass<br>• BMI |
|---|---|

| 117 Lifestyle Monitor | • Exercise<br>• Duration<br>• Heart Rate<br>• Steps<br>• Calories |
|---|---|

| 114 Smart Phone | • Sleep<br>• Snoring<br>• Awakening |
|---|---|

| 118 Digitalized Home Diagnostic or Self-Diagnostic<br>Scanadu Urine | • Glucose<br>• Protein<br>• Leukocytes<br>• Nitrates<br>• Blood<br>• Bilirubin<br>• Urobilinogen<br>• Microalbumin<br>• Dreatinine<br>• Ketone<br>• Specific Gravity<br>• pH in Urine |
|---|---|

FIG. 5

5th — 200: In The Past 12 Hours, Have You Had Any Accidents (Lost Control Of Your Bowels?)
- Yes
- No

6th — 202: How Urgent Has Your Need To Have A Bowel Movement Been In Last 12 Hours
- No Immediate Need
- Slight Immediate Need
- Moderate Immediate Need
- Quite A Bit Immediate Need
- Extreme Immediate Need

7th — 204: How Many Incomplete Bowel Movements in Last 12 Hours
- ☐ One (1)
- ☐ Two (2)
- ☐ Three (3)
- ☐ Four (4)
- ☐ Five (5)
- ☐ Six (6)
- ☐ Seven (7)
- ☐ Eight (8)
- ☐ Nine (9)
- ☐ Ten (10) or more Created By MMC International.

8th — 206: How Many Complete Spontaneous Bowel Movements in Last 12 Hours
- ☐ One (1)
- ☐ Two (2)
- ☐ Three (3)
- ☐ Four (4)
- ☐ Five (5)
- ☐ Six (6)
- ☐ Seven (7)
- ☐ Eight (8)
- ☐ Nine (9)
- ☐ Ten (10) or more Created By MMC International.

FIG. 8B

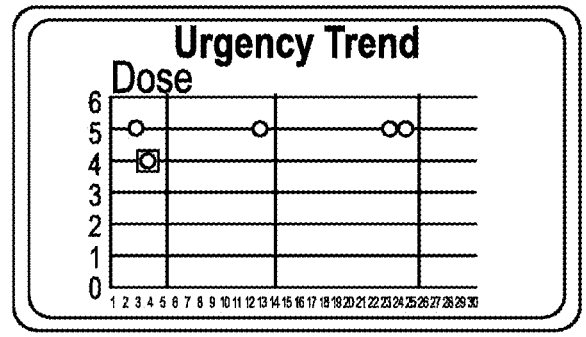
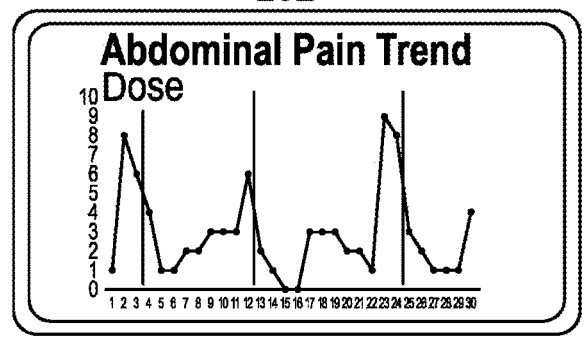
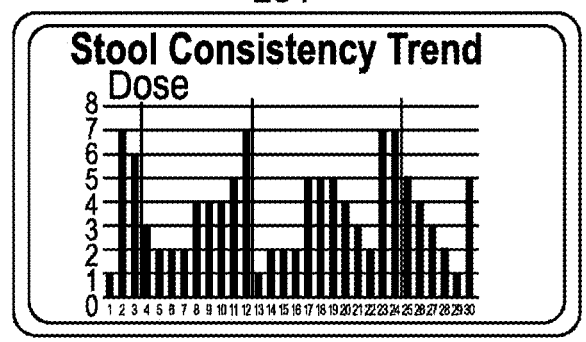
FIG. 11

FIG. 12    Front View

DEVICES, SYSTEM AND METHOD TO CONTROL THE DELIVERY OF ORAL MEDICATIONS TO ENSURE THEY ARE EFFICACIOUS, TAKEN AS PRESCRIBED, AND TO AVOID UNWANTED SIDE EFFECTS

CROSS REFERENCE TO RELATED APPLICATIONS

This application is a national stage entry of International Application No. PCT/US2016/046491, filed on Aug. 11, 2016, which claims benefit of U.S. Provisional Patent Application No. 62/203,638 filed on Aug. 11, 2015 and U.S. Provisional Patent Application No. 62/252,966 filed on Nov. 9, 2015; which are incorporated herein by reference in their entirety to the full extent permitted by law.

FIELD OF THE INVENTION

This application is a national stage entry of International Application No. PCT/US2016/046491, filed on Aug. 11, 2016, which claims benefit of U.S. Provisional Patent Application No. 62/203,638 filed on Aug. 11, 2015 and U.S. Provisional Patent Application No. 62/252,966 filed on Nov. 9, 2015; which are incorporated herein by reference in their entirety to the full extent permitted by law.

BACKGROUND OF THE INVENTION

Avoiding unnecessary medical complications or death by ensuring a drug is efficacious for the patient and that the patient is compliant and persistent with their prescription(s) represents a major unmet need and a trillion-dollar global market opportunity—this is larger than the global pharmaceutical industry. As an example, according to Express Scripts, the largest pharmacy benefit manager in the United States, only 25 to 30 percent of medications are taken per the prescriber's instructions (adherence) . . . and of those taken, only 15 to 20 percent are refilled per the prescriber's instructions (persistence). This lack of adherence and persistence is estimated to result in excess of $300 billion being wasted annually for the treatment of unnecessary medical complications in the United States.

Drug-related hospitalizations account for 2.4 to 6.5 percent of all medical admissions in the general population. A meta-analysis found a fourfold increase in the rate of hospitalization related to adverse drug events (ADE) in older adults compared with younger adults (16.6 versus 4.1 percent). A number of factors in older individuals contribute to their increased risk for developing a drug-related problem. These include frailty, coexisting medical problems, memory issues, polypharmacy, and the use of non-prescribed medications. Estimates indicate that 88 percent of the ADE hospitalizations among older adults were preventable, compared with 24 percent among young persons Optimizing drug therapy is an essential part of medical care. The process of prescribing a medication is complex and includes (i) deciding that a drug is indicated, (ii) choosing the best drug, (iii) determining a dose and schedule appropriate for the patient's physiologic status, (iv) monitoring for effectiveness and toxicity, (v) educating the patient about expected side effects, and (vi) indications for seeking consultation.

Avoidable adverse drug events are the serious consequence of (i) inappropriate drug prescribing, (ii) changes in the patient's reaction to the drug over time due to lifestyle, other medications, other medical conditions, worsening medical condition, or changes in the patients overall well-being, etc., or (iii) addition of new prescription or OTC medications, vitamins, dietary supplements, herbal medicines (e.g., ginseng, *Ginkgo biloba* extract, glucosamine, St. John's wort, echinacea, garlic, saw palmetto, kava, and valerian root), and/or recreational drugs, etc. Often, clinicians do not question patients about use of herbal medicines and patients do not routinely volunteer this information. Furthermore, most patients do not inform their clinician that they were using unconventional and/or recreational medications. A study of the use of 22 supplements in a survey of 369 patients aged 60 to 99 years found potential interactions between supplements and medications for ten of the 22 supplements surveyed. As a result, any new symptom should first be considered to be drug-related until proven otherwise.

Prescribing for older patients, who consume the most medications per capita, presents unique challenges. Premarketing drug trials often exclude geriatric patients and approved doses may not be appropriate for older adults. Many medications need to be used with special caution because of age-related changes in pharmacokinetics (i.e., absorption, distribution, metabolism, and excretion) and pharmacodynamics (the physiologic effects of the drug).

Larger drug storage reservoirs and decreased clearance prolong drug half-lives and lead to increased plasma drug concentrations in older people. Particular care must be taken in determining drug dosages. The proportional increase in body fat relative to skeletal muscle that generally accompanies aging may result in the increased volume of drug distribution. Decreased drug clearance may also result from the natural decline in renal function with age, even in the absence of renal disease.

The same dose could lead to higher plasma concentrations in an older, compared to younger, patient. For example, the volume of distribution for diazepam is increased, and the clearance rate for lithium is reduced, in older adults. From the pharmacodynamic perspective, increasing age may result in an increased sensitivity to the effects of certain drugs, e.g., benzodiazepines and opioids.

The use of greater numbers of drug therapies has been independently associated with an increased risk for an adverse drug event, irrespective of age, and increased risk of hospital admission. Polypharmacy is of particular concern in older people who, compared to younger individuals, tend to have more disease conditions for which therapies are prescribed. Approximately half of the patients taking drugs take two medications and 20 percent five or more. As an example, one study found that among ambulatory older adults with cancer, 84 percent were receiving five or more and 43 percent were receiving 10 or more medications.

The risk of an adverse event due to drug-drug interactions is substantially increased when multiple drugs are taken. For example, the risk of bleeding with warfarin therapy is increased with coadministration of selective and non-selective NSAIDs, SSRIs, omeprazole, lipid-lowering agents, amiodarone, and fluorouracil. A study found hospitalizations for hypoglycemia was six times more likely in patients who had received co-trimoxazole. Digoxin toxicity was 12 times more likely for patients who had been started on clarithromycin. Hyperkalemia was 20 times more likely for patients who were treated with a potassium sparing diuretic.

Periodic evaluation of a patient's drug regimen is an essential component of medical care. However, a survey of Medicare beneficiaries found that more than 30 percent of patients reported they had not talked with their doctor about their different medications in the previous 12 months. Furthermore, when these reviews are done, they often overlook OTC, supplements, herbal medicines and recreational drugs that are being taken by the patient.

Multiple factors contribute to the appropriateness and overall quality of drug prescribing. These include avoidance of inappropriate medications, appropriate use of indicated medications, monitoring for side effects and drug levels, avoidance of drug-drug interactions, and involvement of the patient and integration of patient values. Current measures of the quality of prescribing generally focus on one or some of these factors, but rarely on all.

BRIEF SUMMARY OF THE INVENTION

The present invention describes novel methods and drug dispensing devices, drug specific Apps, drug specific dispensing algorithms, and an integrated support center to ensure any oral medication taken by a patient is efficacious; is only dispensed as prescribed by the healthcare professional (e.g., physician, physician's assistant, nurse practitioner, pharmacist, etc.); is not dispensed if (i) the patient is trying to take the medication sooner than the prescribed interval, (ii) the algorithm deduces that taking the drug may result in an adverse event, even if it could be dispensed within the prescription's guidelines (iii) the drug is past its expiration date, (iv) the drug was not stored properly, e.g., within the right temperature and/or humidity guidelines, and/or (v) the drug batch has been recalled, etc.; and encourages the patient to continue taking the medication as prescribed. In this way, by increasing the drug's efficacy/safety profile, the dispensing system saves the healthcare system money by decreasing the number of interventions, physician's office visits, and hospitalizations—reducing the total cost of care.

The drug specific dispensing algorithm uses encrypted communications to control the drug dispensing device and to communicate with the patient and the support center. The algorithm uses the prescription information, dispensing device information, drug cassette information, patient self-assessment and/or digitally captured physiological, psychological, lifestyle, medications currently being taken, and/or environmental data in a novel drug specific diagnostic algorithm to decide if the drug dispenser should dispense the drug or keep the tamper resistant dispensing unit locked.

The novel drug specific App, which can be operated from a standalone drug dispensing device, interface device (smart phone, tablet and/or computer, or standalone drug dispensing device, etc. with Internet communication capabilities), reads and aggregates; (i) the drug information from the drug cassette, (ii) the devices serial number, operating, environmental and dispensing information from the dispensing device, (iii) patient self-assessment data from input screens on the standalone dispenser, smart phone, tablet, and/or computer, etc., and (iv) digital data generated by wearable devices, consumed, implanted, or injected diagnostic devices, monitoring devices, machines, instruments, gadgets, contraptions, apparatuses, utensils, implements, tools, mechanisms, and informalgizmos, etc.

The drug dispensing device is designed to automatically recognize the drug based upon the drug specific disposable drug cassette docked into the device. The cassette is marked to allow the drug dispenser to ascertain the name of the drug (brand and/or generic), the drug's NDC number, the drug batch number, and drug's expiration date, etc.

The drug dispensing device is designed to be water proof, tamper resistant, withstand being dropped and/or banged, operate and withstand hot and cold temperatures within defined temperature ranges, to be reusable and rechargeable, to have the drug cassette only docked or removed by a healthcare professional, to remain locked from dispensing unless the dispensing device receives an encrypted signal from the authorized smart App, and to dispense the drug with one click. The device, when interfaced with the drug specific App, transmits its serial number via a secure handshake with the App, reads and transmits the drug information on the drug cassette, transmits the current and historic temperatures since the last dispense, and the date and time the drug is dispensed. The drug dispensing device can be configured to dispense one or more drugs and to be controlled by one or more dispensing Apps, one App for each drug.

The multi-drug dispensing units utilize multiple drug cassettes (one each per drug) which are controlled by a consolidation App that combines the individual drug Apps into a single user interface to eliminate duplication of inputs and to facilitate one click drug dispensing for one or more medications. The handshake between Apps is controlled by the biometric security system.

The single drug App, as well as the multi-drug App, require biometric sign on by the patient and utilize a drug specific decision tree algorithm to make dispensing decisions. An encrypted sign on alternative may also be provided. No messages or further communication with the patient are required if drug dispensing is within prescribing guidelines and no potential adverse events are detected by the algorithm. However, if the algorithm decides to keep the dispensing unit locked and not to dispense, even if within prescribing guidelines, then a number of alternative messages are shown on the interface device (standalone dispensing unit, smart phone, tablet, and/or computer, etc. with Internet communications capabilities). These range from telling the patient that the next dose is not authorized by the prescription for a specified period of time to a message indicating that a dose, even within the prescription dosing schedule parameters, should not be taken without first talking with the integrated support center (which serves as a disease management center for patients) or the prescribing healthcare professional. The App facilitates calling the support center using a single click on the alert window.

The App uses the biometric sign on and encrypted communications with the support center to let them know if, for example, (i) the patient may be heading for an undesired event, (ii) that the prescription should be changed, (iii) the drug may have to be changed based upon efficacy concerns, (iv) the patient tries early dispensing too many times (depends on the drug type, e.g., opioids), (iv) appears to be following an abuse pattern, etc., (v) is not following prescribing guidelines, and (vi) is failing to take the medication, etc.

The App allows the patient to ask certain questions regarding when they took their last medication (or medications for multidrug dispensers), how much medication is left, when their next dose is due, the medications expiration date, and the drugs package insert information, etc. It further provides access to personalized analytical charts, some which may be downloaded from the integrated support center's servers or created by the App from the limited information stored by the App, to show how the patient's symptoms are affected when the patient takes a drug dose. This is designed to aid in patient prescription persistence and assist in reinforcing the importance of prescription compliance.

The integrated support center IT system stores authorized log on information, all App history data and enables the continual update of the App history on all the patient's devices where the App has been downloaded. The centralized servers are also designed to: (i) update individual App software as required, (ii) exchange information with authorized electronic medical records, (iii) to, on a real time basis, update the call center's disease management patient specific counselor screens, (iv) conduct metadata analysis on both the patient's individual data as well as analysis that may include information from the patient's electronic medical record, (v) carry out comparative patient analysis against metadata across a patient population with similar characteristics, etc. The analytical output is designed to assist the call center's disease management group in its counseling of the individual patient as well as any reporting and contacts with the patient's prescribing medical professional.

The call center IT systems are designed to allow the call center, via the patient's drug specific App, (i) to change a patient's prescription based on an authorized prescriber's instructions, (ii) to lock and unlock the dispensing ability on the individual drug dispensing unit based upon a discussion with the patient and/or his care giver, and (iii) to lock all appropriate dispensing devices that contain a recalled drug and to instruct the patient via email and/or voice messages to go to their pharmacy to get the drug replaced or to follow the recalling manufacturer's instructions.

The call center's disease management team uses metadata analysis as well as drug registry information, as requested by the prescribing medical profession, to assist them in developing the best course of therapy based on specific queries of the integrated support center's databases and any authorized related electronic medical records.

BRIEF DESCRIPTION OF THE DRAWINGS

Advantages of embodiments of the present invention will be apparent from the following detailed description of the exemplary embodiments thereof, which description should be considered in conjunction with the accompanying drawings in which:

FIG. 3 is an exemplary embodiment of a Biometric Authentication screen.

FIG. 4 is an exemplary embodiment of Patient Self-Assessment Screens.

FIG. 5 is an exemplary embodiment of digitally available patient related diagnostic and physiological information.

FIG. 11 is an exemplary embodiment of Patient Self-Assessment Reporting Screens.

DETAILED DESCRIPTION OF THE INVENTION

I. Terms and Acronyms

Figure 1:
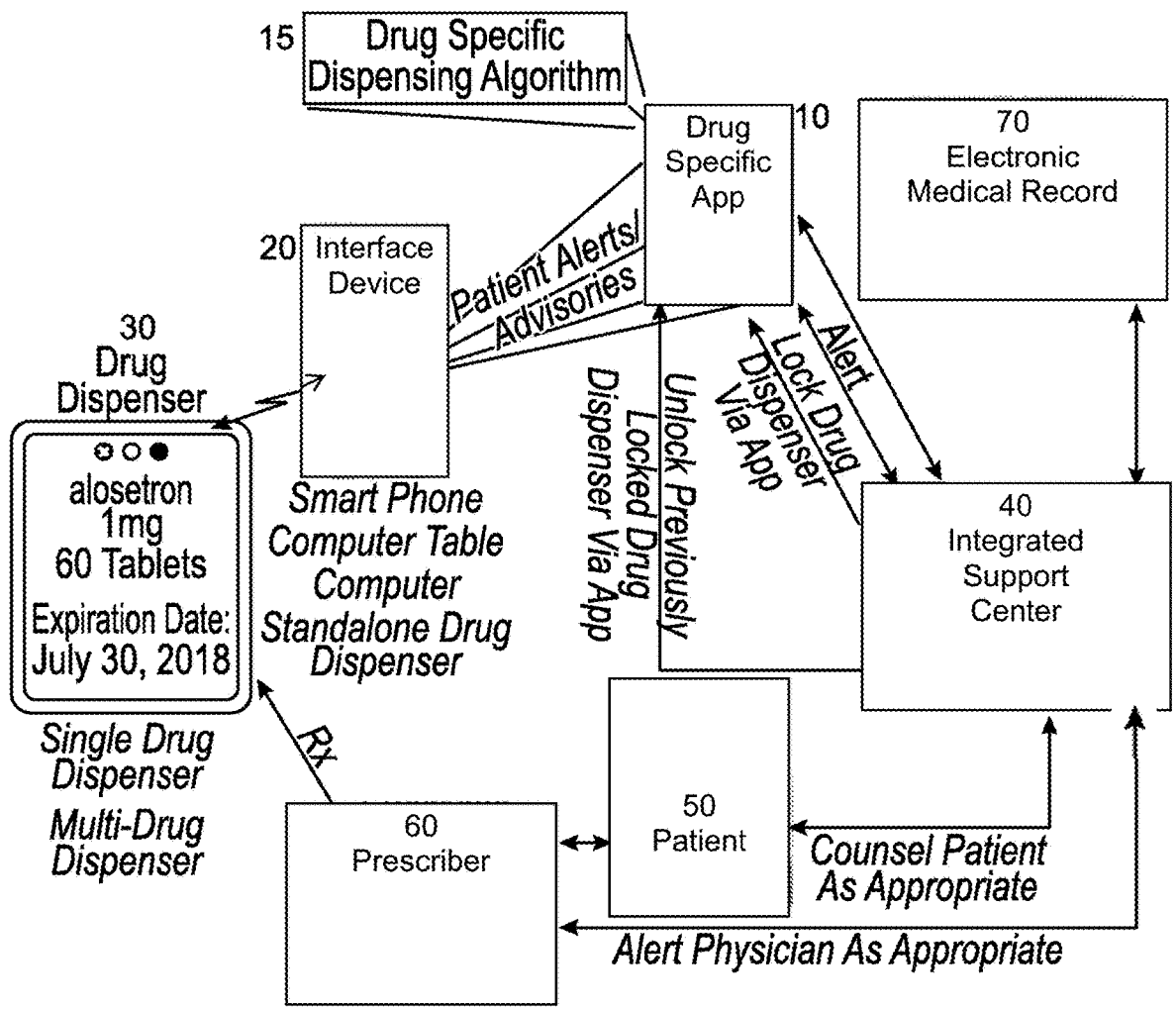
FIG. 1 is an exemplary embodiment of a closed loop system controlled by a Drug Specific Dispensing Algorithm.

Terms used in this document, AKA denotes terms used interchangeably:

Adverse Event (AKA: AE, Adverse Event, Adverse Experience, Adverse Drug Reaction, ADR, or Unexpected Adverse Drug Reaction) refers to (i) a medical occurrence temporally associated with the use of a medicinal product, but not necessarily causally related, (ii) any response to a drug which is noxious and unintended, and which occurs at doses normally used in man for the prophylaxis, diagnosis, or therapy of disease, or for the modifications of physiological function, (iii) an unexpected reaction not consistent with applicable product information or characteristics of the drug, and (iv) the unintended effect occurring at normal dose related to the pharmacological properties of a medication, etc.

Biometric Authentication (AKA biometric identification and biometric authentication.) The definition encompasses but is not limited to biometric technologies that digitally capture fingerprint, palm and full-hand scanners, voice, facial recognition systems, iris scanning technology, document readers, biometric software, and related services capable of wireless, mobile or stationary use to limit access to the Patient. In this document the term also incorporates any system, while not biometric, that allows access via the use of a Login Name in combination with a Password and/or any additional security information.

Consolidation App (AKA multiunit dispenser App) is an App designed to recognize other Drug Specific Apps resident on an Interface Device and then to consolidate the requisite Patient Self-Assessment screens into a single interface for the control and dispensing of multiple drugs.

Digitally Captured refers to Patient data captured by diagnostic or monitoring devices and stored in a machine readable format.

Dispensing Device refers to the Drug Dispensing Unit with a Docked Drug Cassette whose dispensing is controlled by a Drug Specific App.

Dispensing System is comprised of the Dispensing Device and the Integrated Support Center.

Docked refers to the Drug Cassette residing in the Drug Dispensing Unit.

Drug (AKA pharmaceutical, medication, medicament, OTC drug, supplement, or herbal remedy, etc.)

Drug Cassette is the disposable unit that contains a Drug to be dispensed over a defined period of time and/or days per the prescription instructions.

Drug Dispensing Unit is the device where the Drug Cassette is Docked and whose dispensing mechanism (lock, unlock, and dispensing) are controlled by a Drug Specific App.

Drug Specific App refers to an app that requires Biometric Authentication prior to a Patient being able to respond to Patient Self-Assessment screens which are used by the App's Drug Specific Dispensing Algorithm to decide whether or not to signal the Dispensing Device to dispense the medication or to indicate to the patient and/or Integrated Support Center why the drug will not be dispensed.

Drug Specific Dispensing Algorithm refers to the decision tree based algorithm specifically develop for each drug to ascertain if the drug should or should not be dispensed.

Electronic Medical Record (AKA EMR, Patient Medical Record, PMR, etc.)

Encryption (AKA Encrypted, Encrypted communications) is the most effective way to achieve data security. Access requires a secret key or password that enables decryption. Unencrypted data is called plain text; encrypted data is referred to as cipher text.

Expiration Date refers to the date after which a medication should not be taken.

Handshake (AKA Digital Handshake) refers to an exchange of signals between devices ensuring synchronization whenever a connection, as with another device, is initially established.

Integrated Support Center refers to a call center designed to provide patient support, disease management services and/or Dispensing Device support for patients, Prescribers, and/or payers.

Interface Device refers to the device (standalone drug delivery device, smart phone, tablet, computer, etc. with Internet communications capabilities) where the Drug Specific App resides.

Locked indicates the drug cannot be dispensed by the Dispensing Device until the Drug Specific App unlocks the Dispensing Device.

Metadata Analysis (AKA structural metadata and descriptive metadata) as used herein refers to the use of the organization of patient data to enable analysis of both individual and patient population data to ascertain how to best manage medication therapy on a drug by drug and patient by patient basis.

Patient refers to the individual that is prescribed and is taking a medication or medications. Examples include physicians, physician assistants, nurse practitioners, nurses, pharmacists, etc.

Patient Self-Assessment (AKA patient-reported outcome or PRO) covers a whole range of potential types of measurement self-reported by the patient. Each self-assessment scale or question measures a single underlying characteristic (s).

Prescriber is defined as any healthcare professional authorized by an individual country to write a prescription for a drug.

Recall refers to a drug recall issued by the manufacturer or a regulatory agency indicating that a particular drug batch or drug should not be taken.

Tamper Resistant refers to a design that makes it difficult to change, open, remove the cassette, or cause damage to the unit by anyone but authorized persons.

II. List of Drugs, Drug Mechanisms of Action, and Diseases that Invention in its Various Embodiments is Applicable to The invention and its various embodiments can enable the personalization of drug therapy, improve each drugs safety profile, ensure the continued efficacy of a drug for each patient, improve the quality of care, improve the patients quality of life by ensuring proper prescribing and prescription compliance, by promoting prescription persistence, and thereby decreasing the number of drug related medical interventions, and disease related physician visits and hospitalizations thereby decreasing the total cost of patient care. This Invention in its various embodiments is applicable to and by reference incorporates the drugs, drug mechanisms of action, and diseases listed in Table 1-Table 8.

Table 1 lists oral drugs with REMS programs. The listed approved drugs are encompassed in the embodiment of the invention by reference can benefit from an improved drug safety profile. The Invention mitigates prescription risk for the drug manufacturer and prescriber as it shifts the responsibility to the patient. The listing for each drug includes by definition each drug's respective indication(s), strength, dosage form, route of administration, side effect profile, drug interactions, etc.). In addition to Table 1, the embodiment incorporates by reference the Food and Drug Administration's (FDA) Approved Risk Evaluation and Mitigation Strategies (REMS) drugs listing.

TABLE 1

| Oral Drugs with Required REMS Programs |
|---|
| Antipsychotic |
| Seroquel (Quetiapine)<br>Pain Relievers<br>Opioids<br>Codeine<br>Fentanyl and Analogs<br>(Causing Overdoses)<br>Hydrocodone<br>Hydromorphone<br>Methadone<br>Oxycodone<br>Oxymorphone<br>Sedatives (Barbiturates) |
| Amytal (amobarbital)<br>Nembutal (pentobarbital)<br>Seconal (secobarbital)<br>Stimulants (ADHD) |
| Adderall (Amphetamine)<br>Methylphenidate<br>Daytrana<br>Concerta<br>Ritalin<br>Tranquilizers<br>A. Benzodiazepines, Like |
| Klonopin (clonazepam)<br>Valium (diazepam)<br>Xanax (alprazolam)<br>B. Non-Benzodiazepines, Like |
| Ambien (zolpidem)<br>Lunesta (eszopiclone)<br>Sonata (zaleplon)<br>Others |
| Chantix<br>Revlimid<br>Trader<br>Xeljans (Jak Compounds) |

Table 2 lists the Paragraph IV Challenged Drugs that can benefit from the increased patent protection afforded by the drug/device (Invention) combination. The following approved drugs and the FDA's Paragraph IV Drug Product Applications: Generic Drug Patent Challenge Notifications list are encompassed in the embodiment of the invention by reference. The listing for each drug includes by definition each drug's respective indication(s), strength, dosage form, route of administration, side effect profile, drug interactions, etc.

TABLE 2

Paragraph IV Challenged Drugs

| BRAND | GENERIC NAME |
|---|---|
| Ampyra | Dalfampridine |
| Daliresp | Roflumilast |
| Angeliq | Drospirenone and Estradiol |
| Nexavar | Sorafenib Tosylate |
| Kuvan | Sapropterin Dihydrochloride |
| Pradaxa | Dabigatran Etexilate Mesylate |
| Tradjenta | Linagliptin |
| Thalomid | Thalidomide |
| Gabitril | Tiagabine Hydrochloride |
| Zohydro ER | Hydrocodone Bitartrate |
| Viibryd | Vilazodone Hydrochloride |
| Abstral | Fentanyl Citrate |
| Letairis | Ambrisentan |
| Lamictal XR | Lamotrigine |
| Zorvolex | Diclofenac |
| Zytiga | Abiraterone Acetate |
| Ella | Ulipristal Acetate |
| Xartemis XR | Oxycodone Hydrochloride and Acetaminophen |
| Doryx | Doxycycline Hyclate |
| Noxafil | Posaconazole |
| Tekturna HCT | Aliskiren Hemifumarate and Hydrochlorothiazide |
| Promacta | Eltrombopag Olamine |

TABLE 2-continued

Paragraph IV Challenged Drugs

| BRAND | GENERIC NAME |
|---|---|
| Gilenya | Fingolimod |
| Afinitor | Everolimus |
| Gleevec | Imatinib Mesylate |
| Brisdelle | Paroxetine |
| Tikosyn | Dofetilide |
| Hysingla ER | Hydrocodone Bitartrate |
| Suboxone | Buprenorphine Hydrochloride and Naloxone Hydrochloride |
| Latuda | Lurasidone Hydrochloride |
| Trokendi XR | Topiramate |
| Contrave | Naltrexone Hydrochloride and Bupropion Hydrochloride |
| Equetro | Carbamazepine |
| Minastrin 24 Fe | Norethindrone Acetate and Ethinyl Estradiol and Ferrous Fumarate |

Table 3: Marketed Drugs lists approved drugs which are encompassed in the embodiment of the invention by reference. Drug compounds of interest are also listed in: Goodman & Gilman's, The Pharmacological Basis of Therapeutics (12th Ed) (Goodman et al. eds) (McGraw-Hill) (2011); and 2015 Physician's Desk Reference which are also encompassed in the embodiment of the invention by reference. The listing for each drug includes by definition each drug's respective indication(s), strength, dosage form, route of administration, side effect profile, drug interactions, etc.

TABLE 3

| Marketed Drug |
|---|
| Abilify (aripiprazole) |
| Abraxane (paclitaxel protein-bound particles for injectable suspension) |
| ABREVA (docosanol) |
| Abstral (fentanyl sublingual tablets) |
| Abthrax (raxibacumab) |
| Accolate |
| Accretropin (somatropin rDNA Original) |
| Aciphex (rabeprazole sodium) |
| Actemra (ocilizumab) |
| Actemra (tocilizumab) |
| Actiq |
| Activella (Estradiol/Norethindrone Acetate) Tablets |
| Actonel |
| ACTOplus met (pioglitazone hydrochloride and metformin hydrochloride) |
| ACTOS |
| Acular (ketorolac tromethamine ophthalmic solution) 0.5% |
| Acuvail (ketorolac tromethamine) |
| Acyclovir Capsules |
| Adcetris (brentuximab vedotin) |
| Adcirca (tadalafil) |
| Adderall (mixed salts of a single-entity amphetamine) |
| Adderall XR |
| Addyi (flibanserin) |
| Adempas (riociguat) |
| Advicor (extended-release niacin/lovastatin) |
| Afinitor (everolimus) |
| Afrezza (insulin human) Inhalation Powder |
| Agenerase (amprenavir) |
| Aggrenox |
| Agrylin (anagrelide HCL) |
| AK-Con-A (naphazoline ophthalmic) |
| Akten (lidocaine hydrochloride) |
| Akynzeo (netupitant and palonosetron) |
| Alamast |
| Albenza (albendazole) |
| Aldara (imiquimod) |
| Aldurazyme (laronidase) |
| Alesse (100 mcg levonorgestrel/20 mcg ethinyl estradiol tablets) |
| Alimta (pemetrexed for injection) |
| Alinia (nitazoxanide) |
| Allegra (fexofenadine hydrochloride) |

TABLE 3-continued

| Marketed Drug |
| --- |

Allegra-D
Alora
Aloxi (palonosetron)
Alphagan (brimonidine)
AlphaNine SD Coagulation Factor IX (Human)
Alprolix [Coagulation Factor IX (Recombinant), Fc Fusion Protein]
Alrex
Altabax (retapamulin)
Altocor (lovastatin) Extended-Release Tablets
Alvesco (ciclesonide)
Amaryl (Glimepiride)
Amerge
Amevive (alefacept)
Amitiza (lubiprostone)
Amoxil (amoxicillin)
Ampyra (dalfampridine)
Amrix (cyclobenzaprine hydrochloride extended release)
Amturnide (aliskiren + amlodipine + hydrochlorothiazide)
Androderm (Testosterone Transdermal System)
AndroGel testosterone gel
AneuVysion Assay
Anexsia
Angiomax (bivalirudin)
Anoro Ellipta (umeclidinium and vilanterol inhalation powder)
Antizol Injection
Anturol (oxybutynin) Gel
Anzemet
Aphthasol
Aplenzin (bupropion hydrobromide)
Apokyn (apomorphine hydrochloride)
Apthasol (Amlexanox)
Aptiom (eslicarbazepine acetate)
Aptivus (tipranavir)
Arava
Arcapta (indacaterol maleate inhalation powder)
Aredia (pamidronate disodium for injection)
Arestin (minocycline hydrochloride)
Argatroban Injection
ARICEPT (donepezil hydrochloride)
Arimidex (anastrozole)
Arixtra
Arnuity Ellipta (fluticasone furoate inhalation powder)
Aromasin Tablets
Arranon (nelarabine)
Arthrotec
Arzerra (ofatumumab)
Asacol (mesalamine)
Astelin nasal spray
Astepro (azelastine hydrochloride nasal spray)
Atacand (candesartan cilexetil)
Atracurium Besylate Injection
Atridox
Atrovent (ipratropium bromide)
Atryn (antithrombin recombinant lyophilized powder for reconstitution)
Aubagio (teriflunomide)
Augmentin (amoxicillin/clavulanate)
Auryxia (Ferric citrate)
Avandamet (rosiglitazone maleate and metformin HCl)
Avandia (rosiglitazone maleate)
Avastin (bevacizumab)
Aveed (testosterone undecanoate) injection
Avelox I.V. (moxifloxacin hydrochloride)
Avinza (morphine sulfate)
Avita Gel
Avonex (Interferon Beta 1-A)
Avycaz (ceftazidime-avibactam)
Axert (almotriptan malate) tablets
Axid AR (nizatidine
Axona (caprylidene)
AzaSite (azithromycin)
Azmacort (triamcinolone acetonide) Inhalation Aerosol
Azor (amlodipine besylate; olmesartan medoxomil)
Azulfidine EN-tabs Tablets (sulfasalazine delayed release tablets, USP)
Bactroban Cream
Bactroban Nasal 2% (mupirocin calcium ointment)
Banzel (rufinamide)
Baraclude (entecavir)
Baycol (cerivastatin sodium)

TABLE 3-continued

Marketed Drug

Bayer Extra Strength Asprin
Beleodaq (belinostat)
Belsomra (suvorexant)
Belviq (lorcaserin hydrochloride)
BeneFIX (coagulation Factor IX (recombinant))
Benicar
Benlysta (belimumab)
Benzamycin (erythromycin 3%-benzoyl peroxide 5% topical gel)
Bepreve (bepotastine besilate ophthalmic solution)
Berinert (C1 Esterase Inhibitor (Human))
Besivance (besifloxacin ophthalmic suspension)
Betapace AF Tablet
Betaxon
Bexsero (Meningococcal Group B Vaccine)
Bextra
Bexxar
Biaxin XL (clarithromycin extended-release tablets)
BiDil (isosorbide dinitrate/hydralazine hydrochloride)
Bio-T-Gel (testosterone gel)
Blincyto (blinatumomab)
Boniva (ibandronate)
Bosulif (bosutinib)
Botox (onabotulinumtoxinA)
Botox Cosmetic (botulinum toxin type A)
Bravelle (urofollitropin for injection, purified)
Breathe Right
Breo Ellipta (fluticasone furoate and vilanterol inhalation powder)
Brilinta (ticagrelor)
Brintellix (vortioxetine)
Brisdelle (low-dose paroxetine mesylate)
Bromfenac
Brovana (arformoterol tartrate)
BSS Sterile Irrigating Solution
Bunavail (buprenorphine and naloxone)
Busulflex
Butrans (buprenorphine) Transdermal System
Bydureon (exenatide extended-release for injectable suspension)
Byetta (exenatide)
Caduet (amlodipine/atorvastatin)
Cafcit Injection
Cambia (diclofenac potassium for oral solution)
Campath
Campostar
Campral (acamprosate calcium)
Camptosar
Canasa (mesalamine)
Cancidas
Captopril and hydrochlorotiazide
Carbaglu (carglumic acid)
Carbatrol
Cardizem (R) (Diltiazem HCl for injection) Monvial (R)
Carrington patch
Caverject (alprostadil)
Cayston (aztreonam for inhalation solution)
CEA-Scan
Cedax (ceftibuten)
Cefazolin and Dextrose USP
Ceftin (cefuroxime axetil)
Celexa
CellCept
Cenestin
Cerdelga (eliglustat)
Cernevit
Cervarix [Human Papillomavirus Bivalent (Types 16 and 18) Vaccine, Recombinant
Cetrotide
Chantix (varenicline)
Children's Advil (pediatric ibuprofen)
Children's Motrin Cold
Chloraprep (chlorhexidine gluconate)
Cholbam (cholic acid)
Cialis (tadalafil)
Cimetadine Hydrochloride Oral Solution 300 mg/5 ml
Cimetidine Hydrochloride Oral Solution
Cimzia (certolizumab pegol)
Cinryze (C1 Inhibitor (Human))
Cipro (ciprofloxacin HCl)
Cipro (ciprofloxacin) I.V. and Cipro (ciprofloxacin HCl) tablets
Clarinex TABLE 3-continued

| Marketed Drug |
| --- |
| Clarithromycin (Biaxin) |
| Claritin RediTabs (10 mg loratadine rapidly-disintegrating tablet) |
| Claritin Syrup (loratadine) |
| Claritin-D 24 Hour Extended Release Tablets (10 mg loratadine, 240 mg pseudoephedrine sulfate) |
| Clemastine fumarate syrup |
| Cleocin (clindamycin phosphate) |
| Cleviprex (clevidipine) |
| Climara |
| Clindamycin phosphate topical gel |
| Clindamycin Phosphate Topical Solution USP 1% |
| Clolar (clofarabine) |
| Clomipramine hydrochloride |
| Clonazepam |
| Coartem (artemether/lumefantrine) |
| Colazal (balsalazide disodium) |
| Colcrys (colchicine) |
| Combivir |
| Cometriq (cabozantinib) |
| Complera (emtricitabine/rilpivirine/tenofovir disoproxil fumarate) |
| Comtan |
| Concerta |
| Condylox Gel 0.5% (pokofilox) |
| Confide |
| Contrave (naltrexone HCl and bupropion HCl) |
| Copaxone |
| Corlanor (ivabradine) |
| Corlopam |
| Corvert Injection (ibutilide fumarate injection) |
| Cosentyx (secukinumab) |
| Cosopt |
| Covera-HS (verapamil) |
| Cresemba (isavuconazonium sulfate) |
| Crestor (rosuvastatin calcium) |
| Crinone 8% (progesterone gel) |
| Crixivan (Indinavir sulfate) |
| Curosurf |
| Cuvposa (glycopyrrolate) |
| Cycloset, bromocriptine mesylate |
| Cylert |
| Cymbalta (duloxetine) |
| Cyramza (ramucirumab) |
| Cystaran (cysteamine hydrochloride) |
| Dacogen (decitabine) |
| Daklinza (daclatasvir) |
| Daliresp (roflumilast) |
| Dalvance (dalbavancin) |
| Daptacel |
| Degarelix (degarelix for injection) |
| DentiPatch (lidocaine transoral delivery system) |
| Depakote (divalproex sodium) |
| Depakote ER (divalproex sodium) |
| Dermagraft-TC |
| Desmopressin Acetate (DDAVP) |
| Desonate (desonide) |
| Detrol (tolterodine tartrate) |
| Detrol LA (tolterodine tartrate) |
| Diclegis (doxylamine succinate + pyridoxine hydrochloride DR tablets) |
| Differin (adapalene gel) Gel, 0.1% |
| Dificid (fidaxomicin) |
| Diltiazem HCL, Extended-Release Capsules |
| Diovan (valsartan) |
| Diovan HCT (valsartan) |
| Ditropan XL (oxybutynin chloride) |
| Doribax (doripenem) |
| Dostinex Tablets (cabergoline tablets) |
| Doxil (doxorubicin HCl liposome injection) |
| Droxia |
| Duavee (conjugated estrogens/bazedoxifene) |
| Duexis (ibuprofen and famotidine) |
| Dulera (mometasone furoate + formoterol fumarate dihydrate) |
| DuoNeb (albuterol sulfate and ipratropium bromide) |
| Duopa (carbidopa and levodopa) enteral suspension |
| Durezol (difluprednate) |
| Dutasteride |
| Dyloject (diclofenac sodium) Injection |
| Dymista (azelastine hydrochloride and fluticasone propionate) |
| Dynabac |

TABLE 3-continued

| Marketed Drug |
| --- |
| DynaCirc CR |
| Edarbi (azilsartan medoxomil) |
| Edarbyclor (azilsartan medoxomil and chlorthalidone) |
| EDEX |
| Edluar (zolpidem tartrate) |
| Edurant (rilpivirine) |
| Effexor (venlafaxin HCL) |
| Effexor XR (venlafaxin HCI) |
| Efient (prasugrel) |
| Egrifta (tesamorelin for injection) |
| Elaprase (idursulfase) |
| Elelyso (taliglucerase alfa) |
| Elestrin (estradiol gel) |
| Elidel |
| Eligard (leuprolide acetate) |
| Eliquis (apixaban) |
| Elitek (rasburicase) |
| Ellence |
| Elliotts B Solution (buffered intrathecal electrolyte/dextrose injection) |
| Elmiron (pentosan polysulfate sodium) |
| Eloctate [Antihemophilic Factor (Recombinant), Fc Fusion Protein] |
| Eloxatin (oxaliplatin/5-fluorouracil/leucovorin) |
| Embeda (morphine sulfate and naltrexone hydrochloride) |
| Emend (aprepitant) |
| Enbrel (etanercept) |
| Entereg (alvimopan) |
| Entocort EC (budesonide) |
| Entresto (sacubitril and valsartan) |
| Entyvio (vedolizumab) |
| Envarsus XR (tacrolimus extended-release) |
| Epanova (omega-3-carboxylic acids) |
| Epivir (lamivudine) |
| Eraxis (anidulafungin) |
| Erbitux (cetuximab) |
| Erivedge (vismodegib) |
| Erwinaze (asparaginase Erwinia chrysanthemi) |
| Esbriet (pirfenidone) |
| Esclim |
| Estradiol tablets |
| Estradiol Transdermal System |
| Estratab (.3 mg) |
| EstroGel (estradiol gel 0.06%) |
| Estrostep (norethindrone acetate and ethinyl estradiol) |
| Ethyol (amifostine) |
| Etodolac |
| Eulexin (flutamide) |
| Evamist (estradiol) |
| Evista (raloxifene hydrochloride) |
| Evotaz (atazanavir and cobicistat) |
| Evoxac |
| Exalgo (hydromorphone hydrochloride) extended release |
| Excedrin Migraine |
| Exelon (rivastigmine tartrate) |
| Exparel (bupivacaine liposome injectable suspension) |
| Extavia (Interferon beta-1 b) |
| Extina (ketoconazole) |
| Eylea (aflibercept) |
| Fabrazyme (agalsidase beta) |
| Famvir (famciclovir) |
| Fanapt (iloperidone) |
| Farxiga (dapagliflozin) |
| Farydak (panobinostat) |
| Faslodex (fulvestrant) |
| Femara (letrozole) |
| Femhrt Tablets |
| FemPatch |
| Femstat 3 (butoconazole nitrate 2%) |
| FEMSTAT One |
| Fenofibrate |
| Feraheme (ferumoxytol) |
| Feridex I.V. |
| Ferriprox (deferiprone) |
| Ferrlecit |
| Fertinex (urofollitropin for injection, purified) |
| Fetzima (levomilnacipran) |
| Finacea (azelaic acid) Gel, 15% |
| Finevin |
| Firazyr (icatibant) |

TABLE 3-continued

Marketed Drug

Flagyl ER
FLOMAX
Flonase Nasal Spray
Flovent Rotadisk
Floxin otic
Floxin Tablets (ofloxacin tablets)
Flublok (seasonal influenza vaccine)
Flucelvax, Influenza Virus Vaccine
FluMist ( Influenza Virus Vaccine)
Fluzone Preservative-free
Focalin (dexmethylphenidate HCl)
Follistim (TM) (follitropin beta for injection)
Folotyn (pralatrexate injection)
Foradil Aerolizer (formoterol fumarate inhalation powder)
Forteo (teriparatide)
Fortesta (testosterone gel)
Fortovase
Fosamax (alendronate sodium)
Fosrenol, lanthanum carbonate
Fragmin
Frova (frovatriptan succinate)
Fulyzaq (crofelemer)
Fusilev (levoleucovorin)
Fuzeon (enfuvirtide)
Fycompa (perampanel)
Galzin (zinc acetate)
Gardasil (quadrivalent human papillomavirus (types 6, 11, 16, 18) recombinant vaccine)
Gastrocrom Oral Concentrate (cromolyn sodium)
GastroMARK
Gattex (teduglutide)
Gazyva (obinutuzumab)
Gelnique (oxybutynin chloride)
Gemzar (gemcitabine HCL)
Generic Transdermal Nicotine Patch
Genotropin (somatropin) injection
Genotropin (somatropin) lyophilized powder
Geodon (ziprasidone mesylate)
Geref (sermorelin acetate for injection)
Gilenya (fingolimod)
Gilotrif (afatinib)
Gleevec (imatinib mesylate)
Gliadel Wafer (polifeprosan 20 with carmustine implant)
Glipizide Tablets
Glucagon
Glyburide Tablets
Glyset (miglitol)
Gonal-F (follitropin alfa for injection)
Gralise (gabapentin)
Grastek (Timothy Grass Pollen Allergen Extract)
Halaven (eribulin mesylate)
Harvoni (ledipasvir and sofosbuvir)
Havrix
Hectorol (Doxercalciferol) Injection
Hepsera (adefovir dipivoxil)
Herceptin
Herceptin (trastuzumab)
Hetlioz (tasimelteon)
Hiberix (Haemophilus b Conjugate Vaccine; Tetanus Toxoid Conjugate)
Horizant (gabapentin enacarbil)
Humalog (insulin lispro)
Humatrope (somatropin [rDNA origin] for injection)
Humira (adalimumab)
Hycamtin (topotecan hydrochloride)
HyQvia [Immune Globulin Infusion 10% (Human) with Recombinant Human Hyaluronidase]
Iamin
Ibrance (palbociclib)
Iclusig (ponatinib)
Ilaris (canakinumab)
Imagent (perflexane lipid microspheres)
Imbruvica (ibrutinib)
Imitrex (sumatriptan) injection and tablets
Imitrex (sumatriptan) nasal spray
Impavido (miltefosine)
Incivek (telaprevir)
Increlex (mecasermin)
Incruse Ellipta (umeclidinium inhalation powder)
Infasurf TABLE 3-continued

| Marketed Drug |
| --- |
| INFERGEN (interferon alfacon-1) |
| Inform HER-2/neu breast cancer test |
| Injectafer (ferric carboxymaltose injection) |
| Inlyta (axitinib) |
| Innohep (tinzaparin sodium) injectable |
| Inspra (eplerenone tablets) |
| Integrilin |
| Intelence (etravirine) |
| Intermezzo (zolpidem tartrate sublingual tablet) |
| Interstim Continence Control Therapy |
| Intron A (Interferon alfa-2b, recombinant) |
| Intuniv (guanfacine extended-release) |
| Invanz |
| Invega (paliperidone) |
| Invirase (saquinavir) |
| Invokana (canagliflozin) |
| Iontocaine |
| Iressa (gefitinib) |
| Isentress (raltegravir) |
| Istodax (romidepsin) |
| IvyBlock |
| Ixempra (ixabepilone) |
| Ixiaro (Japanese Encephalitis Vaccine, Inactivated, Adsorbed) |
| Jakafi (ruxolitinib) |
| Jalyn (dutasteride + tamsulosin) |
| Januvia (sitagliptin phosphate) |
| Jardiance (empagliflozin) |
| Jentadueto (linagliptin plus metformin hydrochloride) |
| Jetrea (ocriplasmin) |
| Jevtana (cabazitaxel) |
| Jublia (efinaconazole) 10% topical gel |
| Juvisync (sitagliptin and simvastatin) |
| Juxtapid (lomitapide) |
| Kadcyla (ado-trastuzumab emtansine) |
| Kadian |
| Kalbitor (ecallantide) |
| Kaletra Capsules and Oral Solution |
| Kalydeco (ivacaftor) |
| Kapvay (clonidine hydrochloride) |
| Kcentra (Prothrombin Complex Concentrate) |
| Kengreal (cangrelor) |
| Keppra |
| Kerydin (tavaborole) |
| Ketek (telithromycin) |
| Ketoprofen |
| Keytruda (pembrolizumab) |
| Kineret |
| Kineret, anakinra |
| Klaron (sodium sulfacet amide lotion) Lotion, 10% |
| Kogenate FS (Antihemophilic Factor Recombinant) |
| Korlym (mifepristone) |
| Krystexxa (pegloticase) |
| Kuvan (sapropterin dihydrochloride) |
| Kybella (deoxycholic acid) |
| Kynamro (mipomersen sodium) |
| Kyprolis (carfilzomib) |
| Kytril (granisetron) solution |
| Kytril (granisetron) tablets |
| Lamictal (lamotrigine) Chewable Dispersible Tablets |
| Lamictal Chewable Dispersible Tablets |
| Lamisil (terbinafine hydrochloride) Dermagel, 1% |
| Lamisil (terbinafine hydrochloride) Solution, 1% |
| Lamisil (terbinafine hydrochloride) Tablets |
| Lamisil Solution, 1% |
| Lantus (insulin glargine [rDNA origin] injection) |
| Latuda (lurasidone) |
| Lazanda (fentanyl citrate) nasal spray |
| Lemtrada (alemtuzumab) |
| Lenvima (lenvatinib) |
| Lescol (fluvastatin sodium) |
| Lescol (fluvastatin sodium) capsules, Rx |
| Lescol XL (fluvastatin sodium) tablet, extended release |
| Letairis (ambrisentan) |
| Leukine (sargramostim) |
| Levaquin |
| Levitra (vardenafil) |
| Levo-T (levothyroxine sodium) |
| Levoxyl |

TABLE 3-continued

| Marketed Drug |
|---|
| Lexapro (escitalopram oxalate) |
| Lexiva (fosamprenavir calcium) |
| Lexxel (enalapril maleate-felodipine ER) |
| Lidoderm Patch (lidocaine patch 5%) |
| Linzess (linaclotide) |
| Lipitor (atorvastatin calcium) |
| Liptruzet (ezetimibe and atorvastatin) |
| Lithobid (Lithium Carbonate) |
| Livalo (pitavastatin) |
| Lo Minastrin, (norethindrone acetate, ethinyl estradiol, ferrous fumarate) |
| Lodine (etodolac) |
| Lodine XL (etodolac) |
| Lotemax |
| Lotrisone (clotrimazole/betamethasone diproprionate) lotion |
| Lotronex (alosetron HCL) Tablets |
| Lovenox (enoxaparin sodium) Injection |
| Lucentis (ranibizumab injection) |
| Lucentis (ranibizumab) |
| Lumigan (bimatoprost ophthalmic solution) |
| Lunesta (eszopiclone) |
| Lupron Depot (leuprolide acetate for depot suspension) |
| Lusedra (fospropofol disodium) |
| Lustra |
| LUVOX (fluvoxamine maleate) |
| Luxiq (betamethasone valerate) Foam |
| Luzu (luliconazole) Cream 1% |
| Lynparza (olaparib) |
| Lyrica (pregabalin) |
| Lysteda (tranexamic acid) |
| Macugen (pegaptanib) |
| Makena (hydroxyprogesterone caproate injection) |
| Malarone (atovaquone; proguanil hydrochloride) Tablet |
| Marplan Tablets |
| Marqibo (vinCRIStine sulfate LIPOSOME injection) |
| Mavik (trandolapril) |
| Maxalt |
| Mekinist (trametinib) |
| Mentax (1% butenafine HCl cream) |
| Menveo (meningitis vaccine) |
| MERIDIA |
| Merrem I.V. (meropenem) |
| Mesnex |
| Metadate CD |
| Metaglip (glipizide/metformin HCl) |
| Metaprotereol Sulfate Inhalation Solution, 5% |
| Metozolv ODT (metoclopramide hydrochloride) |
| MetroLotion |
| Metronidazole 1.3% Vaginal Gel |
| Mevacor (lovastatin) tablets |
| Miacalcin (calcitonin-salmon) Nasal Spray |
| Micardis (telmisartan) |
| Micardis HCT (telmisartan and hydrochlorothiazide) |
| Microzide (hydrochlorothiazide) |
| Migranal |
| Minoxidil Topical Solution 2% for Women |
| Miraluma test |
| Mirapex |
| Mircera (methoxy polyethylene glycol-epoetin beta) |
| Mircette |
| Mirena (levonorgestrel-releasing intrauterine system) |
| Mirvaso (brimonidine) |
| Mobic (meloxicam) Tablets |
| Monistat 3 (miconazole nitrate) |
| Monurol |
| Movantik (naloxegol) |
| Moxatag (amoxicillin) |
| Mozobil (plerixafor injection) |
| Multaq (dronedarone) |
| Muse |
| Myalept (metreleptin for injection) |
| Mylotarg (gemtuzumab ozogamicin) |
| Myobloc |
| Myozyme (alglucosidase alfa) |
| Myrbetriq (mirabegron) |
| Naglazyme (galsulfase) |
| Naltrexone Hydrochloride Tablets |
| Namenda (memantine HCl) |
| Namzaric (memantine hydrochloride extended-release + donepezil hydrochloride) |

TABLE 3-continued

| Marketed Drug |
|---|

Naprelan (naproxen sodium)
Nasacort AQ (triamcinolone acetonide) Nasal Spray
NasalCrom Nasal Spray
Nascobal Gel (Cyanocobalamin, USP)
Nasonex Nasal Spray
Natazia (estradiol valerate + dienogest)
Natazia (estradiol valerate and estradiol valerate/dienogest)
Natesto, (testosterone) nasal gel
Natpara (parathyroid hormone)
Natrecor (nesiritide)
Nesina (alogliptin)
Neulasta
Neumega
Neupogen
Neupro (Rotigotine Transdermal System)
Neupro (rotigotine)
Neurontin (gabapentin)
Neurontin (gabapentin) oral solution
Neutroval (tbo-filgrastim)
Nexavar (sorafenib)
Nexium (esomeprazole magnesium)
Niaspan
NicoDerm CQ
Nicorette (nicotine polacrilex)
Nicotrol nasal spray
Nicotrol transdermal patch
Nitrostat (nitroglycerin) Tablets
Nolvadex
NORCO tablets (Hydrocodone Bitartrate/Acetaminophen 10 mg/325 mg)
Norditropin (somatropin (rDNA origin) for injection)
Noritate
Normiflo
Northera (droxidopa)
Norvir (ritonavir)
Novantrone (mitoxantrone hydrochloride)
NovoLog (insulin aspart)
Novolog Mix 70/30
Novothyrox (levothyroxine sodium)
Noxafil (posaconazole)
Nplate (romiplostim)
Nucynta (tapentadol)
Nuedexta (dextromethorphan hydrobromide and quinidine sulfate)
Nulojix (belatacept)
Nutropin (somatropin-rDNA origin)
NuvaRing
Nuvigil (armodafinil)
Nymalize (nimodipine)
Obizur [Antihemophilic Factor (Recombinant), Porcine Sequence]
Ocuflox (ofloxacin opthalmic solution) 0.3%
OcuHist
Odomzo (sonidegib)
Ofev (nintedanib)
Oleptro (trazodone hydrochloride)
Olysio (simeprevir)
Omidria (phenylephrine and ketorolac injection)
Omnicef
Omontys (peginesatide)
Onfi (clobazam)
Onglyza (saxagliptin)
Onsolis (fentanyl buccal)
Opdivo (nivolumab)
Opsumit (macitentan)
Oral Cytovene
Oralair (Sweet Vernal, Orchard, Perennial Rye, Timothy and Kentucky Blue Grass Mixed Pollens Allergen Extract)
Oravig (miconazole)
Orbactiv (oritavancin)
Orencia (abatacept)
Orfadin (nitisinone)
Orkambi (lumacaftor and ivacaftor)
Ortho Evra
Ortho Tri-Cyclen Tablets (norgestimate/ethinyl estradiol)
Ortho-Prefest
OsmoCyte Pillow Wound Dressing
Osphena (ospemifene)
Otezla (apremilast)
Ovidrel (gonadotropin, chorionic human recombinant)
Oxecta (oxycodone HCl)

TABLE 3-continued

| Marketed Drug |
| --- |

Oxtellar XR (oxcarbazepine extended release)
Oxycodone and Aspirin
Oxycodone with Acetaminophen 5 mg/325 mg
OxyContin (oxycodone HCl controlled-release)
Oxytrol (oxybutynin transdermal system)
Ozurdex (dexamethasone)
Pancreaze (pancrelipase)
Panretin Gel
Patanase (olopatadine hydrochloride)
Paxil (paroxetine hydrochloride)
Paxil CR (paroxetine hydrochloride)
Pediarix Vaccine
Pegasys (peginterferon alfa-2a)
Peg-Intron (peginterferon alfa-2b)
Pennsaid (diclofenac sodium topical solution)
Pentoxifylline
Pepcid Complete
Periostat (doxycycline hyclate)
Perjeta (pertuzumab)
PhosLo
Photodynamic Therapy
Photofrin
Picato (ingenol mebutate) gel
Pindolol
Plavix (clopidogrel bisulfate)
Plegridy (peginterferon beta-1a)
Plenaxis (abarelix for injectable suspension)
Pomalyst (pomalidomide)
Posicor
Potiga (ezogabine)
Pradaxa (dabigatran etexilate mesylate)
Praluent (alirocumab)
Pramipexole
Prandin
Pravachol (pravastatin sodium)
Precose (acarbose)
Premarin (conjugated estrogens)
Prempro
Prempro & Premphase (conjugated estrogens/medroxyprogesterone acetate tablets)
Prestalia (perindopril arginine and amlodipine besylate)
PREVACID(R) (lansopraxole)
PREVEN; Emergency Contraceptive Kit
Prevnar 13 (Pneumococcal 13-valent Conjugate Vaccine)
Prevpac
Prezcobix (darunavir and cobicistat)
Prezista (darunavir)
Priftin
Prilosec (omeprazole)
Prilosec (omeprazole)/Biaxin (clarithromycin) Combination Therapy
Prinivil or Zestril (Lisinopril)
ProAmatine (midodrine)
Procanbid (procainamide hydrochloride extended-release tablets)
Prochloroperazine
Prochlorperazine
Procysbi (cysteamine bitartrate)
Prograf
Proleukin
Prolia (denosumab)
Promacta (eltrombopag)
Prometrium
Propecia
Proscar
Protonix (pantoprazole sodium) Delayed Release Tablets
Protonix (pantoprazole sodium) Delayed-Release Tablets
Protonix (pantoprazole sodium) Intravenous Formulation
Protopic (tacrolimus) ointment
Provenge (sipuleucel-T)
Proventil HFA Inhalation Aerosol
Prozac Weekly (fluoxetine HCl)
Pulmozyme (dornase alfa)
Qnasl (beclomethasone dipropionate) nasal aerosol
Qsymia (phentermine + topiramate extended-release)
Quadramet (Samarium Sm 153 Lexidronam Injection)
Quartette (levonorgestrel/ethinyl estradiol and ethinyl estradiol)
Qudexy XR (topiramate)
Quillivant XR (methylphenidate hydrochloride)
Quixin (levofloxacin)
Qutenza (capsaicin)

TABLE 3-continued

| Marketed Drug |
|---|
| Qvar (beclomethasone dipropionate) |
| Ragwitek (Short Ragweed Pollen Allergen Extract) |
| Ranexa (ranolazine) |
| Ranitidine Capsules |
| Ranitidine Tablets |
| Rapamune (sirolimus) oral solution |
| Rapamune (sirolimus) Tablets |
| Rapivab (peramivir injection) |
| Raplon |
| Ravicti (glycerol phenylbutyrate) |
| Raxar (grepafloxacin) |
| Rayos (prednisone) delayed-release tablets |
| Rebetol (ribavirin) |
| REBETRON (TM) Combination Therapy |
| Rebif (interferon beta-1a) |
| Reclast (zoledronic acid) |
| Rectiv (nitroglycerin) ointment 0.4% |
| Redux (dexfenfluramine hydrochloride) |
| Refludan |
| REGRANEX (becaplermin) Gel |
| Relenza |
| Relpax (eletriptan hydrobromide) |
| Remeron (Mirtazapine) |
| Remeron SolTab (mirtazapine) |
| Remicade (infliximab) |
| Reminyl (galantamine hydrobromide) |
| Remodulin (treprostinil) |
| Renagel (sevelamer hydrochloride) |
| RenaGelRenagel (sevelamer hydrochloride) |
| Renova (tretinoin emollient cream) |
| Renvela (sevelamer carbonate) |
| ReoPro |
| Repatha (evolocumab) |
| REPRONEX(menotropins for injection, USP) |
| Requip (ropinirole hydrochloride) |
| Rescriptor Tablets (delavirdine mesylate tablets) |
| Rescula (unoprostone isopropyl ophthalmic solution) 0.15% |
| RespiGam (Respiratory Syncitial Virus Immune Globulin Intravenous) |
| Restasis (cyclosporine ophthalmic emulsion) |
| Retavase (reteplase) |
| Retin-A Micro (tretinoin gel) microsphere, 0.1% |
| Revlimid (lenalidomide) |
| Rexulti (brexpiprazole) |
| Reyataz (atazanavir sulfate) |
| Rhinocort Aqua Nasal Spray |
| Rid Mousse |
| Rilutek (riluzole) |
| Risperdal Oral Formulation |
| Ritalin LA (methylphenidate HCl) |
| Rituxan |
| Rixubis (Coagulation Factor IX (Recombinant)] |
| Rocephin |
| Rotarix (Rotavirus Vaccine, Live, Oral) |
| Rotateq (rotavirus vaccine, live oral pentavalent) |
| Rozerem (ramelteon) |
| Ruconest (C1 esterase inhibitor [recombinant]) |
| Rytary (carbidopa and levodopa) extended-release capsules |
| Rythmol |
| Sabril (vigabatrin) |
| Saizen |
| Salagen Tablets |
| Samsca (tolvaptan) |
| Sanctura (trospium chloride) |
| Sancuso (granisetron) |
| Saphris (asenapine) |
| Savaysa (edoxaban) |
| Savella (milnacipran hydrochloride) |
| Saxenda (liraglutide [rDNA origin] injection) |
| Sclerosol Intrapleural Aerosol |
| Seasonale, Lo Seasonale, Seasonique (ethinylestradiol + levonorgestrel) |
| SecreFlo (secretin) |
| Selegiline tablets |
| Self-examination breast pad |
| Selzentry (maraviroc) |
| Sensipar (cinacalcet) |
| Seprafilm |
| Serevent |
| Seroquel (R) (quetiapine fumarate) Tablets |

TABLE 3-continued

| Marketed Drug |
| --- |
| Signifor (pasireotide diaspartate) |
| Signifor LAR (pasireotide) |
| Silenor (doxepin) |
| Simponi (golimumab) |
| Simulect |
| Singulair |
| Sirturo (bedaquiline) |
| Sitavig (acyclovir) buccal tablets |
| Sivextro (tedizolid phosphate) |
| Skelid (tiludronate disodium) |
| Skin Exposure Reduction Paste Against Chemical Warfare Agents (SERPACWA) |
| Sklice (ivermectin) lotion |
| Soliris (eculizumab) |
| Somatuline Depot (lanreotide acetate) |
| Somavert (pegvisomant) |
| Sonata |
| Soolantra (ivermectin) cream, 1% |
| Sovaldi (sofosbuvir) |
| Spectracef |
| Spiriva HandiHaler (tiotropium bromide) |
| SPORANOX (itraconazole) |
| Sprix (ketorolac tromethamine) |
| Sprycel (dasatinib) |
| Stavzor (valproic acid delayed release) |
| Stelara (ustekinumab) |
| Stendra (avanafil) |
| Stiolto Respimat (tiotropium bromide and olodaterol) |
| Stivarga (regorafenib) |
| Strattera (atomoxetine HCl) |
| Stribild (elvitegravir, cobicistat, emtricitabine, tenofovir disoproxil fumarate) |
| Striverdi Respimat (olodaterol) |
| Stromectol (ivermectin) |
| Subsys (fentanyl sublingual spray) |
| Subutex/Suboxone (buprenorphine/naloxone) |
| Sulfamylon |
| Supartz |
| Supprelin LA (histrelin acetate) |
| Surfaxin (lucinactant) |
| Sustiva |
| Sutent (sunitinib malate) |
| Sutent (sunitinib) |
| Sylatron (peginterferon alfa-2b) |
| Sylvant (siltuximab) |
| Symlin (pramlintide) |
| Synagis |
| Synercid I.V. |
| Synjardy (empagliflozin and metformin hydrochloride) |
| Synribo (omacetaxine mepesuccinate) |
| Synthroid (levothyroxine sodium) |
| Synvisc, Synvisc-One (Hylan GF 20) |
| Tafinlar (dabrafenib) |
| Tamiflu capsule |
| Tanzeum (albiglutide) |
| Tarceva (erlotinib, OSI 774) |
| Targiniq ER (oxycodone hydrochloride + naloxone hydrochloride) extended-release tablets |
| Tasigna (nilotinib hydrochloride monohydrate) |
| Tasmar |
| Tavist (clemastine fumarate) |
| Taxol |
| Taxotere (Docetaxel) |
| Tazorac topical gel |
| Tecfidera (dimethyl fumarate) |
| Technivie, (ombitasvir, paritaprevir and ritonavir) |
| Teczem (enalapril maleate/diltiazem malate) |
| Teflaro (ceftaroline fosamil) |
| Tegretol (carbamazepine) |
| Tegretol XR (carbamazepine) |
| Tekamlo (aliskiren + amlodipine) |
| Tekturna (aliskiren) |
| Temodar |
| Tequin |
| Testim |
| Testoderm TTS CIII |
| Teveten (eprosartan mesylate plus hydrochlorothiazide) |
| Teveten (eprosartan mesylate) |
| Thalomid |
| Tiazac (diltiazem hydrochloride) |

TABLE 3-continued

| Marketed Drug |
|---|
| Tikosyn Capsules |
| Tilade (nedocromil sodium) |
| Timentin |
| Tindamax, tinidazole |
| Tivicay (dolutegravir) |
| Tivorbex (indomethacin) |
| Tobi |
| Tolmetin Sodium |
| Topamax (topiramate) |
| Toprol-XL (metoprolol succinate) |
| Torisel (temsirolimus) |
| Toviaz (fesoterodine fumarate) |
| Tracleer (bosentan) |
| Tradjenta (linagliptin) |
| Travatan (travoprost ophthalmic solution) |
| Trazadone 150 mg |
| Treanda (bendamustine hydrochloride) |
| Trelstar Depot (triptorelin pamoate) |
| Trelstar LA (triptorelin pamoate) |
| Tretten (Coagulation Factor XIII A-Subunit [Recombinant]) |
| Tribenzor (olmesartan medoxomil + amlodipine + hydrochlorothiazide) |
| Tricor (fenofibrate) |
| Trileptal (oxcarbazepine) Tablets |
| Trilipix (fenofibric acid) |
| Tri-Nasal Spray (triamcinolone acetonide spray) |
| Tripedia (Diptheria and Tetanus Toxoids and Acellular Pertussis Vaccine Absorbed) |
| Trisenox (arsenic trioxide) |
| Triumeq (abacavir, dolutegravir, and lamivudine) |
| Trivagizole 3 (clotrimazole) Vaginal Cream |
| Trivora-21 and Trivora-28 |
| Trizivir (abacavir sulfate; lamivudine; zidovudine AZT) Tablet |
| Trokendi XR (topiramate) |
| Trovan |
| Trulicity (dulaglutide) |
| Tudorza Pressair (aclidinium bromide inhalation powder) |
| Twinrix |
| Tygacil (tigecycline) |
| Tykerb (lapatinib) |
| Tysabri (natalizumab) |
| Tyvaso (treprostinil) |
| Tyzeka (telbivudine) |
| Uceris (budesonide) |
| Uloric (febuxostat) |
| Ultracet (acetaminophen and tramadol HCl) |
| UltraJect |
| Ultresa (pancrelipase) delayed-release capsules |
| Unituxin (dinutuximab) |
| UroXatral (alfuzosin HCl extended-release tablets) |
| Urso |
| UVADEX Sterile Solution |
| Valchlor (mechlorethamine) gel |
| Valcyte (valganciclovir HCl) |
| Valstar |
| Valtrex (valacyclovir HCl) |
| Vancenase AQ 84 mcg Double Strength |
| Vanceril 84 mcg Double Strength (beclomethasone dipropionate, 84 mcg) Inhalation Aerosol |
| Vandetanib (vandetanib) |
| Vaprisol (conivaptan) |
| Varithena (polidocanol injectable foam) |
| VariZIG, Varicella Zoster Immune Globulin (Human) |
| Varubi (rolapitant) |
| Vascepa (icosapent ethyl) |
| Vectibix (panitumumab) |
| Velcade (bortezomib) |
| Veltin (clindamycin phosphate and tretinoin) |
| Venofer (iron sucrose injection) |
| Ventolin HFA (albuterol sulfate inhalation aerosol) |
| Veramyst (fluticasone furoate) |
| Verapamil |
| Verdeso (desonide) |
| Veregen (kunecatechins) |
| VERSED (midazolam HCl) |
| Vesicare (solifenacin succinate) |
| Vfend (voriconazole) |
| Viadur (leuprolide acetate implant) |
| Viagra |
| Vibativ (telavancin) |

TABLE 3-continued

| Marketed Drug |
|---|
| Viberzi (eluxadoline) |
| Victoza (liraglutide) |
| Victrelis (boceprevir) |
| Vidaza (azacitidine) |
| Videx (didanosine) |
| Viekira Pak (ombitasvir, paritaprevir, ritonavir and dasabuvir) tablets |
| Viibryd (vilazodone hydrochloride) |
| Vimizim (elosulfase alfa) |
| Vimovo (naproxen + esomeprazole) |
| Vimpat (lacosamide) |
| Viokace (pancrelipase) tablets |
| Vioxx (rofecoxib) |
| VIRACEPT (nelfinavir mesylate) |
| Viramune (nevirapine) |
| Viread (tenofovir disoproxil fumarate) |
| Viroptic |
| Visicol Tablet |
| Visipaque (iodixanol) |
| Vistide (cidofovir) |
| Visudyne (verteporfin for injection) |
| Vitrasert Implant |
| Vitravene Injection |
| Vivelle (estradiol transdermal system) |
| Vivelle-Dot (estradiol transdermal system) |
| Vivitrol (naltrexone for extended-release injectable suspension) |
| Vogelxo (testosterone) gel |
| Voraxaze (glucarpidase) |
| Votrient (pazopanib) |
| Vpriv (velaglucerase alfa for injection) |
| Vyvanse (Lisdexamfetamine Dimesylate) |
| Warfarin Sodium tablets |
| Welchol (colesevelam hydrochloride) |
| Western blot confirmatory device |
| Wilate (von Willebrand Factor/Coagulation Factor VIII Complex (Human) |
| Xalkori (crizotinib) |
| Xarelto (rivaroxaban) |
| Xartemis XR (oxycodone hydrochloride and acetaminophen) extended release |
| Xeljanz (tofacitinib) |
| Xeloda |
| Xenazine (tetrabenazine) |
| Xenical/Orlistat Capsules |
| Xeomin (incobotulinumtoxinA) |
| Xgeva (denosumab) |
| Xiaflex (collagenase clostridium histolyticum) |
| Xifaxan (rifaximin) |
| Xigduo XR (dapagliflozin + metformin hydrochloride) |
| Xigris (drotrecogin alfa [activated]) |
| Xofigo (radium Ra 223 dichloride) |
| Xolair (omalizumab) |
| Xopenex |
| Xtandi (enzalutamide) |
| Xtoro (finafloxacin otic suspension) 0.3% |
| Xyrem (sodium oxybate) |
| Xyzal (levocetirizine dihydrochloride) |
| Yasmin (drospirenone/ethinyl estradiol) |
| Yervoy (ipilimumab) |
| ZADITOR |
| Zagam (sparfloxacin) tablets |
| Zaltrap (ziv-aflibercept) |
| Zanaflex (tizanidine hydrochloride) |
| Zantac 75 Efferdose |
| Zelboraf (vemurafenib) |
| Zelnorm (tegaserod maleate) Tablets |
| Zemaira (alpha1-proteinase inhibitor) |
| Zemplar |
| Zenapax |
| Zenpep (pancrelipase) |
| Zerbaxa (ceftolozane + tazobactam) |
| Zerit (stavudine) |
| Zevalin (ibritumomab tiuxetan) |
| Zingo (lidocaine hydrochloride monohydrate) |
| Zioptan (tafluprost ophthalmic solution) |
| Ziprasidone (ziprasidone hydrochloride) |
| Zipsor (diclofenac potassium) |
| Zirgan (ganciclovir ophthalmic gel) |
| Zithromax (azithromycin) |
| Zocor |
| Zofran |

TABLE 3-continued

Marketed Drug

Zohydro ER (hydrocodone bitartrate) Extended-Release Capsules
Zoladex (10.8 mg goserelin acetate implant)
Zoloft (sertraline HCl)
Zometa (zoledronic acid)
Zomig (zolmitriptan)
Zonegran (zonisamide) Capsules
Zontivity (vorapaxar)
Zortress (everolimus)
Zosyn (sterile piperacillin sodium/tazobactam sodium)
Zubsolv (buprenorphine and naloxone)
Zuplenz (ondansetron oral soluble film)
Zyban Sustained-Release Tablets
Zyclara (imiquimod)
Zydelig (idelalisib)
Zyflo (Zileuton)
Zykadia (ceritinib)
Zymaxid (gatifloxacin ophthalmic solution)
Zyprexa
Zyrtec (cetirizine HCl)
Zytiga (abiraterone acetate)

Table 4 lists sample drugs and their side effects. The listed drugs and their side effects highlight a number side effects that can be used for the development of the Patient Specific Dispensing Algorithm. The following approved drugs in Table 4 and in the following marketed drug compounds and drug compounds in development are encompassed in the embodiment of the invention by reference. Marketed drug compounds of interest are also listed in: Goodman & Gilman's, The Pharmacological Basis of Therapeutics (12th Ed) (Goodman et al. eds) (McGraw-Hill) (2011); and 2015 Physician's Desk Reference. Drug compounds in development that are of interest are also listed in: Cortellis™ Competitive Intelligence by Thomson Reuters; Adis R&D; and Pharmaprojects by Citeline. The drug The listing for each drug includes by definition each drug's respective indication(s), strength, dosage form, route of administration, side effect profile, drug interactions, etc.

TABLE 4

SAMPLE DRUGS AND THEIR SIDE EFFECTS

| | |
|---|---|
| Afinitor | Common:<br>Cardiovascular: Hypertension (tumors, 4% to 13%; kidney transplant, 30%; liver transplant, 17%), Peripheral edema (tumors, 13% to 39%; kidney transplant, 45%; liver transplant, 18%)<br>Dermatologic: Acne (tumors, 10% to 22%; transplant, 1% to less than 10%), Eczema (renal angiomyolipoma, 10%), Rash (tumors, 5% to 59%)<br>Endocrine metabolic: Dyslipidemia (kidney transplant, 15%), Hypercholesterolemia (tumors, 66% to 85%; kidney transplant, 17%), Hyperlipidemia (kidney transplant, 21%; liver transplant, 24%), Hypertriglyceridemia (tumors, 27% to 73%), Hypoalbuminemia (breast cancer, 33%), Hypophosphatemia (tumors, 9% to 49%; kidney transplant, 13%), Increased glucose level, All grades (tumors, 14% to 75%; kidney transplant, 12%)<br>Gastrointestinal: Constipation (tumors, 10% to 14%; kidney transplant, 38%), Decrease in appetite (tumors, 6% to 30%; transplant, 1% to less than 10%), Diarrhea (tumors, 14% to 50%; kidney transplant, 19%; liver transplant, 19%), Nausea (tumors, 16% to 29%; kidney transplant, 29%; liver transplant, 14%), Stomatitis (tumors, 44% to 78%; kidney transplant, 8%), Vomiting (tumors, 15% to 29%; kidney transplant, 15%)<br>Hematologic: Anemia, All Grades (tumors, 41% to 86%; kidney transplant, 26%), Decreased lymphocyte count, All grades (tumors, 20% to 54%), Partial thromboplastin time increased (subependymal giant cell astrocytoma, 72%), Thrombocytopenia, All grades (tumors, 19% to 54%; transplant, up to 10%)<br>Hepatic: Alkaline phosphatase raised (tumors, 32% to 74%; transplant, 1% to less than 10%), ALT/SGPT level raised (tumors, 18% to 51%), AST/SGOT level raised (tumors, 23% to 69%)<br>Immunologic: Impaired wound healing (kidney transplant, 35%; liver transplant, 11%)<br>Neurologic: Asthenia (tumors, 13% to 33%)<br>Otic: Otitis media (renal angiomyolipoma, 6%)<br>Psychiatric: Mental disorder (subependymal giant cell astrocytoma, 21%)<br>Renal: Serum creatinine raised (tumors, 19% to 50%; kidney transplant, 18%), Urinary tract infectious disease (tumors, 5% to 16%; kidney transplant, 22%)<br>Reproductive: Amenorrhea (renal angiomyolipoma, 15%), |

TABLE 4-continued

SAMPLE DRUGS AND THEIR SIDE EFFECTS

|  |  |
|---|---|
|  | Irregular periods (tumors, 10% to 11%), Menorrhagia (renal angiomyolipoma, 10%)<br>Respiratory: Cough (tumors, 20% to 30%; kidney transplant, 7%), Dyspnea (tumors, 20% to 24%), Sinusitis (tumors, 3% to 6%), Upper respiratory infection (tumors, 11% to 31%; kidney transplant, 16%)<br>Other: Fatigue (tumors, 14% to 45%; kidney transplant, 9%), Fever (tumors, 15% to 31%; kidney transplant, 19%; liver transplant, 13%)<br>Serious:<br>Cardiovascular: Pericardial effusion (Transplant, less than 1%)<br>Hematologic: Anemia, Grade 3 or 4 (tumors, 6.6% to 15%), Decreased lymphocyte count, Grade 3 or 4 (tumors, 1% to 16%), Hemorrhage (renal cell carcinoma, 3%), Leukopenia (tumors, 37% to 58%; kidney transplant, 3%; liver transplant, 12%), Pancytopenia, All grades (transplant, 1% to less than 10%), Thrombosis, Thrombotic microangiopathy (Transplant, less than 1%), Thrombotic thrombocytopenic purpura (Transplant, less than 1%), Venous thromboembolism (transplant, 1% to less than 10%)<br>Immunologic: Infectious disease (tumors, 37% to 50%; kidney transplant, 62%; liver transplant, 50%)<br>Neurologic: Seizure (renal angiomyolipoma, 5%)<br>Renal: Hemolytic uremic syndrome (Transplant, less than 1%), Renal failure (renal cell carcinoma, 3%), Thrombosis of renal artery (transplant, 1% to less than 10%)<br>Respiratory: Interstitial lung disease (Less than 1%), Non-infectious pneumonia (Up to 19%), Pleural effusion (tumors, 7%), Pneumocystis pneumonia, Pneumonia (renal cell carcinoma, 6%), Pulmonary embolism (PNET, 2.5%; transplant, 1% to less than 10%)<br>Other: Angioedema (Transplant, up to 6.8%), Sepsis (tumors less than 1%; transplant, 1% to less than 10%) |
| Ampyra | Common<br>Gastrointestinal: Abdominal pain (7%), Nausea (7% to 13%), Vomiting (13%)<br>Musculoskeletal: Abnormal gait (5%), Backache (5%)<br>Neurologic: Asthenia (7%), Dizziness (7%), Headache (7%), Insomnia (9%)<br>Psychiatric: Anxiety (5%)<br>Renal: Urinary tract infectious disease (12%)<br>Serious<br>Immunologic: Anaphylaxis, Hypersensitivity reaction<br>Neurologic: Seizure |
| Angeliq | Common<br>Gastrointestinal: Abdominal pain (3.6% to 6.5%)<br>Neurologic: Headache (6%)<br>Reproductive: Abnormal vaginal bleeding (3.6% to 14%), Pain of breast (3.3% to 17.9%)<br>Serious<br>Cardiovascular: Myocardial infarction<br>Gastrointestinal: Disorder of gallbladder<br>Hematologic: Deep venous thrombosis<br>Neurologic: Cerebrovascular accident<br>Ophthalmic: Thrombosis of retinal vein<br>Reproductive: Breast cancer, Endometrial carcinoma, Ovarian cancer<br>Respiratory: Pulmonary embolism |
| Brisdelle | Common<br>Dermatologic: Diaphoresis (1% to 14%)<br>Gastrointestinal: Constipation (4.9% to 16%), Diarrhea (7.9% to 19.2%), Loss of appetite (2% to 9%), Nausea (up to 36.3%), Xerostomia (10.8% to 20.6%)<br>Neurologic: Asthenia (2.9% to 22%), Dizziness (6% to 14%), Headache (psychiatric conditions, 17% to 18%; menopausal vasomotor symptoms, 6.3%), Insomnia (11% to 24%), Somnolence (12.7% to 24%), Tremor (up to 14.7%)<br>Ophthalmic: Blurred vision (2% to 7.8%)<br>Reproductive: Abnormal ejaculation (5.8% to 28%), Disorder of female genital organs (2% to 9%), Erectile dysfunction (1.9% to 9%), Reduced libido (males, 6% to 15%; females, 0% to 9%)<br>Serious<br>Psychiatric: Depression, Exacerbation, Suicidal thoughts, Suicide<br>Other: Serotonin syndrome |
| Contrave | Common:<br>Gastrointestinal: Constipation (19.2%), Diarrhea (7.1%), Nausea (32.5%), Vomiting (10.7%), Xerostomia (8.1%)<br>Neurologic: Dizziness (9.9%), Headache (17.6%), Insomnia (9.2%)<br>Psychiatric: Anxiety (4.2%) |

TABLE 4-continued

SAMPLE DRUGS AND THEIR SIDE EFFECTS

| | |
|---|---|
| | Serious: |
| | Cardiovascular: Hypertension (3.2%), Increased heart rate, Myocardial infarction (Less than 2%) |
| | Dermatologic: Erythema multiforme (Rare), Stevens-Johnson syndrome (Rare) |
| | Endocrine metabolic: Hypoglycemia |
| | Gastrointestinal: Cholecystitis (Less than 2%), Hematochezia (Less than 2%) |
| | Hepatic: Hepatotoxicity |
| | Immunologic: Anaphylaxis, Delayed hypersensitivity disorder |
| | Musculoskeletal: Intervertebral disc prolapse (Less than 2%) |
| | Neurologic: Amnesia (Less than 2%), Seizure (0.1%) |
| | Ophthalmic: Angle-closure glaucoma |
| | Psychiatric: Depression (6.3% to 7.1%), Mania, Psychiatric symptom, Suicidal thoughts (0.03%) |
| | Renal: Infectious disorder of kidney (Less than 2%), Serum creatinine raised (Less than 2%) |
| | Respiratory: Pneumonia (Less than 2%) |
| Daliresp | Common: |
| | Endocrine metabolic: Weight decreased (7% to 20%) |
| | Gastrointestinal: Decrease in appetite (2.1%), Diarrhea (9.5%), Nausea (4.7%) |
| | Immunologic: Influenza (2.8%) |
| | Musculoskeletal: Backache (3.2%) |
| | Neurologic: Dizziness (2.1%), Headache (4.4%), Insomnia (2.4%) |
| | Serious: |
| | Psychiatric: Suicidal thoughts |
| Doryx | Common: |
| | Dermatologic: Rash (4%) |
| | Gastrointestinal: Diarrhea (3.3%), Loss of appetite, Nausea (8% to 13.4%), Sensitive dentin, Sore gums, Vomiting (8.1%) |
| | Musculoskeletal: Myalgia (6.4%) |
| | Reproductive: Bacterial vaginosis (3.3%) |
| | Serious: |
| | Dermatologic: Drug hypersensitivity syndrome, Erythema multiforme, Photosensitivity, Stevens-Johnson syndrome, Toxic epidermal necrolysis |
| | Gastrointestinal: Clostridium difficile diarrhea |
| | Hepatic: Hepatotoxicity (Rare) |
| | Immunologic: Anaphylaxis, Superinfection |
| | Musculoskeletal: Arrest of bone development AND/OR growth |
| | Neurologic: Pseudotumor cerebri |
| Ella | Common: |
| | Gastrointestinal: Abdominal pain (8% to 15%), Nausea (12% to 13%) |
| | Neurologic: Headache (18% to 19%) |
| Equetro | Common |
| | Cardiovascular: Hypotension |
| | Dermatologic: Pruritus (8%), Rash (7%) |
| | Gastrointestinal: Constipation (10%), Nausea (29%), Vomiting (18%), Xerostomia (8%) |
| | Neurologic: Asthenia (8%), Ataxia (15%), Dizziness (44%), Somnolence |
| | Ophthalmic: Blurred vision (6%), Nystagmus |
| | Serious |
| | Cardiovascular: Atrioventricular block, Cardiac dysrhythmia, Congestive heart failure, Eosinophilic myocarditis, Hypersensitivity, Syncope |
| | Dermatologic: Stevens-Johnson syndrome, Toxic epidermal necrolysis |
| | Endocrine metabolic: Hypocalcemia, Hyponatremia (4% to 21.7%), Water intoxication syndrome |
| | Gastrointestinal: Pancreatitis |
| | Hematologic: Agranulocytosis, Aplastic anemia, Bone marrow depression, Eosinophilia, Leukopenia, Pancytopenia, Thrombocytopenia |
| | Hepatic: Hepatitis, Hepatotoxicity, Liver failure, Vanishing bile duct syndrome |
| | Immunologic: Drug hypersensitivity syndrome |
| | Neurologic: Acute intermittent porphyria |
| | Renal: Azotemia, Renal failure |
| | Respiratory: Pulmonary hypersensitivity |
| | Other: Angioedema |
| Gabitril | Common: |
| | Dermatologic: Pruritus (2%) |
| | Gastrointestinal: Abdominal pain (5% to 7%), Nausea (11%) |
| | Neurologic: Asthenia (18% to 23%), Ataxia (5% to 9%), Confusion (5%), Disturbance in speech (4%), Dizziness (27 to 31%), Feeling |

TABLE 4-continued

SAMPLE DRUGS AND THEIR SIDE EFFECTS

| | |
|---|---|
| | nervous (10% to 14%), Insomnia (5% to 6%), Somnolence (18% to 21%), Tremor (9% to 21%), Unable to concentrate (6% to 14%)<br>Respiratory: Pharyngitis (7% to 8%)<br>Serious:<br>Dermatologic: Stevens-Johnson syndrome<br>Neurologic: Seizure, in patients without epilepsy, Status epilepticus, Status epilepticus, in patients without a history of seizure<br>Psychiatric: Suicidal thoughts |
| Gilenya | Common:<br>Gastrointestinal: Abdominal pain (11%), Diarrhea (13%)<br>Hepatic: Increased liver enzymes (All elevations (ALT/GGT/AST),15%; up to 3 times ULN (ALT, AST), 14%; 5 times ULN or greater (ALT, AST), 4.5%)<br>Immunologic: Influenza (11%)<br>Musculoskeletal: Backache (10%), Pain, In Extremity (10%)<br>Neurologic: Headache (25%)<br>Respiratory: Cough (12%), Sinusitis (11%)<br>Serious:<br>Cardiovascular: Atrioventricular block (up to 4.7%), Bradyarrhythmia (3%.)<br>Dermatologic: Malignant melanoma<br>Hematologic: Lymphocytopenia (Severe) (7%)<br>Immunologic: Cryptococcosis, Herpesvirus infection (9%), Infectious disease (All infections, 72%; serious infections, 2.3%)<br>Neurologic: Cryptococcal meningitis, Posterior reversible encephalopathy syndrome, Progressive multifocal leukoencephalopathy<br>Ophthalmic: Macular retinal edema (0.5% to 1.5%) |
| Gleevec | Common:<br>Cardiovascular: Edema<br>Dermatologic: Night sweats (13% to 17%), Rash (Adult, 8.9% to 38.1%; pediatric, acute lymphocytic leukemia, grade 3 or 4, 4%)<br>Endocrine metabolic: Weight increased (5% to 32%)<br>Gastrointestinal: Diarrhea (Adult, 25% to 59.3%; pediatric, acute lymphoblastic leukemia, grade 3 or 4, 9%), Nausea (Adults, 41.7% to 73%; pediatric, acute lymphoblastic leukemia, grade 3 or 4, 16%), Vomiting (10.8% to 58%)<br>Musculoskeletal: Arthralgia (8.8% to 40%), Cramp (28% to 62%), Musculoskeletal pain (Chronic myeloid leukemia, 20.5% to 49%), Myalgia (Adult, 9% to 33.2%; pediatric, acute lymphoblastic leukemia grade 3 or 4, 5%), Spasm (16.3% to 49%)<br>Neurologic: Asthenia (12% to 21%), Dizziness (4.6% to 16%), Headache (8.2% to 36%), Insomnia (9.8% to 14%)<br>Respiratory: Cough (13% to 27%), Nasopharyngitis (1% to 30.5%), Pain, Pharyngolaryngeal (Chronic myeloid leukemia, 18.1%), Pharyngitis (Chronic myeloid leukemia, 10% to 15%)<br>Other: Fatigue (20% to 57%), Fever (6.2% to 41%), Influenza (Chronic myeloid leukemia, 0.8% to 13.8%), Rigor (10% to 12%)<br>Serious:<br>Cardiovascular: Cardiac tamponade, Cardiogenic shock, Congestive heart failure (0.1% to 1%)<br>Dermatologic: Bullous eruption (0.1% to 1%), Erythema multiforme (0.01% to 0.1%), Stevens-Johnson syndrome (0.01% to 0.1%), Toxic epidermal necrolysis<br>Gastrointestinal: Gastrointestinal perforation, Pancreatitis (0.1% to 1%)<br>Hematologic: Anemia (Up to 42%), Febrile neutropenia (1% to 10%), Hemorrhage (All grades, 1% to 53%; grade 3 or 4, 0% to 19%), Neutropenia (Grade 3 or 4, 3.1% to 64%), Pancytopenia (1% to 10%), Thrombocytopenia (Chronic myeloid leukemia (CML), grade 3, 8.5% to 30%; CML, grade 4, up to 33%; dermatofibrosarcoma protuberans (oral route): 17%)<br>Hepatic: ALT/SGPT level raised (grade 3 and above, up to 7%), Ascites (0.1% to 1%), AST/SGOT level raised, Hepatic necrosis (0.01% to 0.1%), Hepatotoxicity (chronic myeloid leukemia: all grades, 6% to 12%), Liver failure (0.01% to 0.1%)<br>Neurologic: Cerebral edema, Raised intracranial pressure (0.01% to 0.1%)<br>Ophthalmic: Optic disc edema (0.01% to 0.1%)<br>Otic: Sensorineural hearing loss<br>Renal: Acute renal failure (0.1% to 1%)<br>Respiratory: Acute respiratory failure, Hypoxia (Pediatrics, acute lymphoblastic leukemia, grade 3 or 4, 9%), Pleural effusion (Pediatrics, acute lymphoblastic leukemia, grade 3 or 4, 7%), Pneumonia (Chronic myeloid leukemia, 4% to 13%), Pneumonitis (Pediatric, acute lymphoblastic leukemia, grade 3 or 4, 8%) |

TABLE 4-continued

SAMPLE DRUGS AND THEIR SIDE EFFECTS

| | |
|---|---|
| | Other: Secondary malignant neoplastic disease, Tumor lysis syndrome |
| Hysingla ER | Common: |
| | Cardiovascular: Peripheral edema (1% to less than 5%%) |
| | Dermatologic: Pruritus (0% to less than 5%) |
| | Gastrointestinal: Abdominal pain (1% to less than 5%), Constipation (3% to 11%), Nausea (7% to 10%), Vomiting (3% to 6%), Xerostomia (1% to less than 5%) |
| | Musculoskeletal: Spasm (1% to less than 5%) |
| | Neurologic: Dizziness (2% to 3%), Headache (2% to 4%), Somnolence (1% to 5%), Tremor (3%) |
| | Renal: Urinary tract infectious disease (1% to 5%) |
| | Respiratory: Upper respiratory infection (1% to 3%) |
| | Other: Fatigue (1% to 4%) |
| | Serious: |
| | Cardiovascular: Hypotension (less than 1%), Orthostatic hypotension (less than 1%), Prolonged QT interval, Syncope |
| | Gastrointestinal: Difficulty swallowing (less than 1%) |
| | Neurologic: Raised intracranial pressure, Seizure |
| | Respiratory: Respiratory depression |
| | Other: Drug withdrawal syndrome in neonate of dependent mother, Opioid withdrawal (less than 1%) |
| Kuvan | Common: |
| | Gastrointestinal: Diarrhea (4% or more), Vomiting (4% or more) |
| | Neurologic: Headache (4% or greater) |
| | Respiratory: Cough (4% or more), Nasal congestion (4% or more), Nasal discharge (4% or more), Pain in throat (4% or more), Upper respiratory infection (17%) |
| | Serious: |
| | Cardiovascular: Myocardial infarction |
| | Gastrointestinal: Gastrointestinal hemorrhage |
| | Hematologic: Hemorrhage, Post-procedural |
| | Neurologic: Seizure |
| | Respiratory: Respiratory failure |
| Lamictal XR | Common: |
| | Dermatologic: Rash (7% to 14%) |
| | Gastrointestinal: Abdominal pain (immediate-release, 5% to 10%), Diarrhea (immediate-release, 6% to 11%; extended-release, 5%), Indigestion (immediate-release, 2% to 7%), Nausea (immediate-release, 7% to 25%; extended-release, 7%), Vomiting (immediate-release, 5% to 20%; extended-release, 6%)) |
| | Neurologic: Asthenia (immediate-release, 2% to 8%; extended-release, 6%), Ataxia (immediate-release, 2% to 11%), Coordination problem (immediate-release, 6% to 7%; extended-release, 3%), Dizziness (immediate-release, 7% to 54%; extended release, 14%), Headache (immediate-release, 29%), Insomnia (immediate-release, 5% to 10%), Somnolence (immediate-release, 9% to 17%; extended-release, 5%), Tremor (immediate-release, 4% to 10%; extended-release, 6%), Vertigo (immediate-release, 2%; extended-release, 3%) |
| | Ophthalmic: Blurred vision (immediate-release, 11% to 25% (adults) and 4% (children); extended-release, 3%), Diplopia (immediate-release, 24% to 49% (adults) and 5% (children); extended-release, 5%) |
| | Psychiatric: Anxiety (immediate-release, 4%; extended-release, 3%), Depression (immediate-release, 4%; extended-release, 3%) |
| | Reproductive: Dysmenorrhea (immediate-release, 5% to 7%) |
| | Respiratory: Rhinitis (immediate-release, 7% to 14%) |
| | Other: Pain (immediate-release, 5%) |
| | Serious: |
| | Dermatologic: Erythema multiforme (less than 0.1%), Rash, Serious (0.08% to 0.8%), Stevens-Johnson syndrome (0.08% to 0.8%.), Toxic epidermal necrolysis (0.08% to 0.8%) |
| | Hematologic: Anemia (immediate release, less than 0.1%), Disseminated intravascular coagulation, Eosinophilia (immediate release, less than 0.1%), Leukopenia (immediate release, 0.1% to 1%), Thrombocytopenia (immediate release, less than 0.1%) |
| | Hepatic: Liver failure |
| | Immunologic: Drug hypersensitivity syndrome |
| | Neurologic: Aseptic meningitis |
| | Other: Angioedema (less than 0.1%), Neuroleptic malignant syndrome |
| Latuda | Common: |
| | Gastrointestinal: Diarrhea (3% to 5%), Nausea (10% to 17%), Vomiting (2% to 8%) |
| | Neurologic: Akathisia (5.6% to 22%), Extrapyramidal disease (10% to 39%), Parkinsonism (5% to 17%), Somnolence (7.3% to 26.5%) |

TABLE 4-continued

SAMPLE DRUGS AND THEIR SIDE EFFECTS

| | |
|---|---|
| | Psychiatric: Anxiety (4% to 5%)<br>Serious:<br>Cardiovascular: Orthostatic hypotension (0.3% to 2.1%), Syncope (0.1%)<br>Hematologic: Agranulocytosis<br>Neurologic: Cerebrovascular accident (0.1% to 1%), Seizure (less than 1%), Tardive dyskinesia, Transient ischemic attack<br>Psychiatric: Suicidal thoughts (0.4% to 1.1%)<br>Renal: Serum creatinine raised (2% to 4%)<br>Other: Neuroleptic malignant syndrome |
| Minastrin 24 FE | Common:<br>Dermatologic: Acne (2.7%)<br>Endocrine metabolic: Abnormal weight gain (2%)<br>Gastrointestinal: Nausea (4.6%), Vomiting (2% to 6%)<br>Neurologic: Headache (6.3%)<br>Psychiatric: Mood swings (2.2%)<br>Reproductive: Abnormal cervical smear (3.1%), Amenorrhea (22% to 36%), Bacterial vaginosis (3.1%), Breast tenderness (3.4%), Candida vaginitis (6.1%), Intermenstrual bleeding - irregular (24 to 35%), Menstrual cramp (4.4%)<br>Serious:<br>Cardiovascular: Myocardial infarction<br>Hematologic: Arterial thrombosis, Venous thromboembolism<br>Hepatic: Adenoma of liver, Liver carcinoma<br>Neurologic: Cerebrovascular accident<br>Ophthalmic: Thrombosis of retinal vein |
| Nexavar | Common:<br>Cardiovascular: Hypertension, All grades (19.1%)<br>Dermatologic: Acral erythema (hepatocellular carcinoma, 21%; renal cell carcinoma, 30%; thyroid carcinoma, 69%), Alopecia (hepatocellular carcinoma, 14%; renal cell carcinoma, 27%; thyroid carcinoma, 67%), Peeling of skin, Rash (up to 35%)<br>Endocrine metabolic: Hypoalbuminemia (hepatocellular carcinoma, 59%), Hypocalcemia (hepatocellular carcinoma, 27%; renal cell carcinoma, 12%; thyroid carcinoma, 36%), Hypophosphatemia (35% to 45%), Raised TSH level (thyroid carcinoma, 41%), Weight decreased (hepatocellular carcinoma, 30%; renal cell carcinoma, 10%; thyroid carcinoma, 49%)<br>Gastrointestinal: Abdominal pain (renal cell carcinoma, 11%; hepatocellular carcinoma, 31%; thyroid carcinoma, 20%), Decrease in appetite (thyroid carcinoma, 30%), Diarrhea (43% to 68%), Increased serum lipase level (40% to 41%), Loss of appetite (16% to 29%), Nausea (21% to 24%), Serum amylase raised (30% to 34%)<br>Hematologic: Lymphocytopenia (renal cell carcinoma, 23%; hepatocellular carcinoma, 47%), Thrombocytopenia (renal cell carcinoma; 12%; hepatocellular carcinoma, 46%)<br>Hepatic: ALT/SGPT level raised, All grades (thyroid carcinoma, 59%), AST/SGOT level raised, All grades (thyroid carcinoma, 54%)<br>Immunologic: Infectious disease (10% or greater)<br>Other: Fatigue (37% to 46%), Pain (10% or greater)<br>Serious:<br>Cardiovascular: Congestive heart failure (1.9%), Hypertension, Grade 3 or 4 (4.3%), Hypertensive crisis (0.1% to less than 1%), Myocardial infarction, Myocardial ischemia, Prolonged QT interval (Less than 0.1%)<br>Dermatologic: Squamous cell carcinoma of skin (thyroid carcinoma, 3%), Stevens-Johnson syndrome, Toxic epidermal necrolysis<br>Gastrointestinal: Gastrointestinal hemorrhage, Gastrointestinal perforation (0.1% to less than 1%), Pancreatitis (0.1% to less than 1%)<br>Hematologic: Hemorrhage (renal cell carcinoma, 15.3%; thyroid carcinoma, 17.4%)<br>Hepatic: ALT/SGPT level raised, Grade 3 or higher (thyroid carcinoma, 4%), AST/SGOT level raised, Grade 3 or 4 (thyroid carcinoma, 2%), Hepatitis (less than 0.1%)<br>Neurologic: Cerebral hemorrhage (0.1% to less than 1%), Posterior reversible encephalopathy syndrome (0.1% to less than 1%)<br>Respiratory: Interstitial lung disease (0.1% to less than 1%), Respiratory tract hemorrhage |
| Noxafil | Common:<br>Endocrine metabolic: Hypokalemia (prophylaxis, 22% to 30%)<br>Gastrointestinal: Diarrhea (prophylaxis, 29% to 42%; oropharyngeal candidiasis, 10%; refractory oropharyngeal candidiasis, 13%), Nausea (prophylaxis, 19% to 38%; oropharyngeal candidiasis, 9%; refractory oropharyngeal |

TABLE 4-continued

SAMPLE DRUGS AND THEIR SIDE EFFECTS

| | |
|---|---|
| | candidiasis, 29%), Vomiting (prophylaxis, 12% to 29%; oropharyngeal candidiasis, 7%; refractory oropharyngeal candidiasis, 28%)<br>Neurologic: Headache (prophylaxis, 14% to 28%; oropharyngeal candidiasis, 8%; refractory oropharyngeal candidiasis, 20%)<br>Other: Fever (prophylaxis, 21% to 45%; oropharyngeal candidiasis, 6%; refractory oropharyngeal candidiasis, 34%)<br>Serious:<br>Cardiovascular: Prolonged QT interval (1% to 2%), Torsades de pointes (less than 5%)<br>Hepatic: Cholestasis (rare), Liver failure (rare) |
| Pradaxa | Common:<br>Gastrointestinal: Esophagitis, Gastritis, Gastroesophageal reflux disease (Atrial fibrillation, 5.5%), Gastrointestinal hemorrhage (DVT and pulmonary embolism, 0.7% to 3.1%; nonvalvular atrial fibrillation, 6.1%), Gastrointestinal ulcer, Indigestion (DVT and pulmonary embolism, 7.5%)<br>Hematologic: Bleeding (DVT and pulmonary embolism prophylaxis, 10.5%; nonvalvular atrial fibrillation, 16.6%)<br>Serious:<br>Cardiovascular: Myocardial infarction (DVT and pulmonary embolism, 0.32% to 0.66%; nonvalvular atrial fibrillation, 0.7%)<br>Gastrointestinal: Gastrointestinal hemorrhage, Major (DVT and pulmonary embolism, 0.3% to 0.6%; nonvalvular atrial fibrillation, 1.6%)<br>Hematologic: Bleeding, Major (DVT and pulmonary embolism, 0.3% to 1.4%; nonvalvular atrial fibrillation, 3.3%), Thrombosis<br>Immunologic: Anaphylaxis<br>Neurologic: Epidural hematoma, Intracranial hemorrhage (nonvalvular atrial fibrillation, 0.3%; DVT and pulmonary embolism, 0.1%), Traumatic spinal subdural hematoma<br>Respiratory: Bleeding, Alveolar |
| Promacta | Common:<br>Gastrointestinal: Diarrhea (Chronic hepatitis C-associated thrombocytopenia, 19%; chronic idiopathic thrombocytopenic purpura, adults, 9%, pediatric, 5%; aplastic anemia, 21%), Nausea (Chronic hepatitis C-associated thrombocytopenia, 19%; chronic idiopathic thrombocytopenic purpura, 4% to 9%; aplastic anemia, 33%), Pain in throat (Chronic idiopathic thrombocytopenic purpura, 4%; aplastic anemia, 14% 4%), Pharyngitis (4%), Vomiting (6%)<br>Hematologic: Anemia (chronic hepatitis C-associated thrombocytopenia, 40%)<br>Hepatic: ALT/SGPT level raised (Chronic idiopathic thrombocytopenic purpura, 5% to 6%; chronic ITP, pediatric, 6%), AST/SGOT level raised (Adult, 4%; pediatric, 5%), Hyperbilirubinemia (6% to 8%)<br>Musculoskeletal: Myalgia (2% to 12%)<br>Neurologic: Headache (Chronic hepatitis C-associated thrombocytopenia and aplastic anemia, 21%; chronic idiopathic thrombocytopenic purpura, 10%)<br>Ophthalmic: Cataract (4% to 7%)<br>Renal: Urinary tract infectious disease (5%)<br>Respiratory: Cough (Aplastic anemia, 23%; chronic ITP, pediatric, 9%), Epistaxis (13%)<br>Other: Fatigue (Chronic hepatitis C-associated thrombocytopenia and aplastic anemia, 28%; chronic idiopathic thrombocytopenic purpura, 4%), Fever (Chronic hepatitis C-associated thrombocytopenia, 30%; aplastic anemia, 14%)<br>Serious:<br>Hematologic: Bleeding, Portal vein thrombosis (chronic hepatitis C-associated thrombocytopenia, 1%), Thrombosis (chronic hepatitis C-associated thrombocytopenia, 3%)<br>Hepatic: Hepatotoxicity, Liver failure (chronic hepatitis C-associated thrombocytopenia, 7%), Liver function tests abnormal (11%)<br>Renal: Acute renal failure |
| Promacta<br>Suboxone | Common:<br>Dermatologic: Hyperhidrosis (SL tablet, 14%; buccal film, 1% to less than 5%)<br>Gastrointestinal: Abdominal pain (SL tablet, 11.2%), Constipation (SL tablet, 12.1%; buccal film, 1% to less than 5%), Nausea (SL tablet, induction phase, 5%; long-term use, 15%), Vomiting (SL tablet, 5% to 7.5%)<br>Neurologic: Headache (SL tablet, induction phase, 7%; long-term use, 36.4%; buccal film, 5% or greater), Insomnia (SL tablet, 14%; buccal film, greater than 1% and less than 5%) |

TABLE 4-continued

SAMPLE DRUGS AND THEIR SIDE EFFECTS

| | |
|---|---|
| | Other: Drug withdrawal (SL tablet, 25.2%; buccal film, at least 5%), Pain (SL tablet, 22.4%)<br>Serious:<br>Hepatic: Hepatitis<br>Immunologic: Anaphylaxis<br>Neurologic: Central nervous system depression<br>Respiratory: Respiratory depression<br>Other: Drug dependence (Buccal film, 1% to less than 5%) |
| Tekturna HCT | Common:<br>Endocrine metabolic: Hyperkalemia (0.8% to 36.9%), Hypokalemia (2.2%)<br>Gastrointestinal: Diarrhea (1.6%)<br>Neurologic: Dizziness (2.3%)<br>Renal: Serum blood urea nitrogen raised (11.8%)<br>Respiratory: Cough (1.3%)<br>Serious:<br>Cardiovascular: Hypotension<br>Ophthalmic: Angle-closure glaucoma, acute, Myopia (Acute), Transient |
| Thalomid | Common:<br>Cardiovascular: Edema (multiple myeloma, 13% to 56%), Peripheral edema (erythema nodosum leprosum, 3.1% to 8.3%; multiple myeloma, 34%)<br>Dermatologic: Dry skin (multiple myeloma, 21%), Rash (erythema nodosum leprosum, 20.8%)<br>Endocrine metabolic: Hypocalcemia (multiple myeloma, 72%), Weight gain (multiple myeloma, 3% to 22%), Weight loss (multiple myeloma, 23%)<br>Gastrointestinal: Constipation (erythema nodosum leprosum, 2.8% to 9.4%; multiple myeloma, 50% to 55%), Diarrhea (erythema nodosum leprosum, 4.2% to 18.7%), Indigestion (multiple myeloma, 11%), Nausea (erythema nodosum leprosum, 4.2%; multiple myeloma, 13% to 28%)<br>Hematologic: Leukopenia (erythema nodosum, 16.7% to 25%; multiple myeloma, 35%)<br>Musculoskeletal: Muscle weakness (multiple myeloma, 40%)<br>Neurologic: Asthenia (erythema nodosum leprosum, 5.6% to 21.9%; multiple myeloma, 24%), Confusional state (multiple myeloma, 28%), Dizziness (erythema nodosum leprosum, 4.2% to 19.2%; multiple myeloma, 23%), Somnolence (erythema nodosum leprosum, 36.1% to 37.5%; multiple myeloma, 3% or more), Tremor (erythema nodosum leprosum, 4.2%; multiple myeloma, 26%)<br>Respiratory: Dyspnea (multiple myeloma, 42%), Pneumonia (multiple myeloma, 15%)<br>Other: Fatigue (multiple myeloma, 21% to 79%), Fever (erythema nodosum leprosum, 19.4% to 21.9%; multiple myeloma, 24%)<br>Serious:<br>Cardiovascular: Atrial fibrillation, Grade 3/4 (multiple myeloma, 5%), Cardiac dysrhythmia, Ischemic heart disease (11.1%), Myocardial infarction (1.3%) |
| Tikosyn | Common:<br>Cardiovascular: Chest pain (10%)<br>Neurologic: Dizziness (8%), Headache (11%)<br>Serious:<br>Cardiovascular: Heart block (up to 1.2%), Prolonged QT interval, Torsades de pointes (0.8%), Ventricular arrhythmia (up to 14.5%), Ventricular fibrillation (up to 4.8%), Ventricular tachycardia (up to 12.4%) |
| Tradjenta | Common:<br>Endocrine metabolic: Hypoglycemia (monotherapy, 6.6%; combination therapy, 22.9%)<br>Respiratory: Nasopharyngitis (7%)<br>Serious:<br>Gastrointestinal: Pancreatic cancer, Pancreatitis<br>Immunologic: Anaphylaxis, Hypersensitivity reaction<br>Other: Angioedema, Pancreatic cancer |
| Trokendi XR | Common:<br>Dermatologic: Flushing (pediatrics, 5%)<br>Endocrine metabolic: Serum bicarbonate level abnormal (25% to 67%)<br>Gastrointestinal: Loss of appetite (10% to 24%), Weight decreased (4% to 21%)<br>Immunologic: Infectious disease (2% to 8%)<br>Neurologic: Confusion (3% to 11%), Dizziness (4% to 25%), Impaired cognition (2% to 7%), Impaired psychomotor performance (2% to 13%), Memory impairment (3% to 12%), |

TABLE 4-continued

SAMPLE DRUGS AND THEIR SIDE EFFECTS

| | |
|---|---|
| | Paresthesia (1% to 51%), Reduced concentration span (2% to 10%), Somnolence (6% to 29%)<br>Psychiatric: Feeling nervous (4% to 16%), Mood disorder (4% to 11%)<br>Other: Fatigue (6% to 16%), Fever (1% to 12%)<br>Serious:<br>Dermatologic: Erythema multiforme, Stevens-Johnson syndrome, Toxic epidermal necrolysis<br>Endocrine metabolic: Hyperammonemia (Adolescents, 26%), Hypohidrosis, Increased body temperature, Metabolic acidosis<br>Hepatic: Liver failure<br>Neurologic: Drug-induced encephalopathy<br>Ophthalmic: Glaucoma, Myopia, Visual field defect (epilepsy, 0.1% to 1%)<br>Psychiatric: Suicidal thoughts<br>Renal: Nephrolithiasis (adults, 1% to 3%) |
| Viibryd | Common:<br>Gastrointestinal: Diarrhea (26% to 29%), Nausea (22% to 24%), Vomiting (4% to 5%)<br>Neurologic: Insomnia (6% to 7%)<br>Serious:<br>Cardiovascular: Ventricular premature beats (0.1% to 1%)<br>Psychiatric: Suicidal behavior, Suicidal thoughts<br>Other: Drug withdrawal, Serotonin syndrome (0.1%) |
| Xartemis XR | Common:<br>Gastrointestinal: Constipation (extended-release, 4%), Nausea (extended-release, 31%), Vomiting (extended-release, 9%)<br>Neurologic: Dizziness (extended-release, 13%), Headache (extended-release, 10%), Lightheadedness, Sedated, Somnolence (extended-release, 4%)<br>Serious:<br>Cardiovascular: Disorder of pulmonary circulation, Hypotension, Shock<br>Dermatologic: Acute generalized exanthematous pustulosis, Stevens-Johnson syndrome, Toxic epidermal necrolysis<br>Hematologic: Agranulocytosis, Neutropenia<br>Hepatic: Hepatic necrosis, Hepatotoxicity, Liver failure<br>Immunologic: Anaphylaxis, Hypersensitivity reaction<br>Respiratory: Apnea, Respiratory arrest, Respiratory depression<br>Other: Neonatal Abstinence Syndrome |
| Zohydro ER | Common:<br>Cardiovascular: Peripheral edema (1% to less than 5%%)<br>Dermatologic: Pruritus (0% to less than 5%)<br>Gastrointestinal: Abdominal pain (1% to less than 5%), Constipation (3% to 11%), Nausea (7% to 10%), Vomiting (3% to 6%), Xerostomia (1% to less than 5%)<br>Musculoskeletal: Spasm (1% to less than 5%)<br>Neurologic: Dizziness (2% to 3%), Headache (2% to 4%), Somnolence (1% to 5%), Tremor (3%)<br>Renal: Urinary tract infectious disease (1% to 5%)<br>Respiratory: Upper respiratory infection (1% to 3%)<br>Other: Fatigue (1% to 4%)<br>Serious:<br>Cardiovascular: Hypotension (less than 1%), Orthostatic hypotension (less than 1%), Prolonged QT interval, Syncope<br>Gastrointestinal: Difficulty swallowing (less than 1%)<br>Neurologic: Raised intracranial pressure, Seizure<br>Respiratory: Respiratory depression<br>Other: Drug withdrawal syndrome in neonate of dependent mother, Opioid withdrawal (less than 1%) |
| Zorvolex | Common<br>Gastrointestinal: Constipation (5% to 8%), Diarrhea (6%), Nausea (6% to 7%)<br>Hepatic: Increased liver function test (15%)<br>Neurologic: Headache (4% to 8%)<br>Renal: Urinary tract infectious disease (7%)<br>Respiratory: Nasopharyngitis (6%), Sinusitis (3% to 5%), Upper respiratory infection (8%)<br>Serious<br>Cardiovascular: Myocardial infarction, Thrombosis<br>Dermatologic: Erythema multiforme, Erythroderma, Stevens-Johnson syndrome, Toxic epidermal necrolysis<br>Gastrointestinal: Gastrointestinal hemorrhage, Gastrointestinal perforation<br>Hematologic: Aplastic anemia, Blood coagulation disorder, Hemolytic anemia, Thrombocytopenia<br>Hepatic: Increased liver enzymes, Jaundice, Liver failure<br>Immunologic: Anaphylactoid reaction |

TABLE 4-continued

SAMPLE DRUGS AND THEIR SIDE EFFECTS

| | |
|---|---|
| | Neurologic: Cerebrovascular accident |
| | Renal: Acute renal failure |
| | Respiratory: Bronchospasm |
| Zytiga | Common |
| | Dermatologic: Contusion (13.3%), Flushing (19% to 22.3%) |
| | Endocrine metabolic: Hypercholesterolemia (Greater than 20%), Hyperglycemia (56.6%), Hypertriglyceridemia (62.5%), Hypophosphatemia (23.8%) |
| | Gastrointestinal: Diarrhea (17.6% to 21.6%), Vomiting (10% or higher) |
| | Hematologic: Anemia (Greater than 20%), Lymphocytopenia, All grades (38.2%) |
| | Hepatic: Alkaline phosphatase raised (Greater than 20%) |
| | Musculoskeletal: Joint swelling (29.5% to 30.3%) |
| | Renal: Urinary tract infectious disease (11.5%) |
| | Respiratory: Cough (10.6% to 17.3%), Dyspnea (11.8%) |
| | Other: Fatigue (39.1%) |
| | Serious |
| | Cardiovascular: Cardiac dysrhythmia (7.2%), Cardiorespiratory arrest (0.5%), Chest discomfort, Chest pain, Edema (25.1% to 26.7%), Heart failure (2.1% to 2.3%), Hypertension (8.5% to 21.6%), Myocardial infarction, Sudden cardiac death |
| | Endocrine metabolic: Adrenal insufficiency (0.5%), Hypokalemia (17.2% to 28.3%) |
| | Hematologic: Lymphocytopenia, Grade 3 or 4 (8.7%) |
| | Hepatic: ALT/SGPT level raised (11.1% to 41.9%), AST/SGOT level raised (30.6% to 37.3%), Serum bilirubin raised (6.6%) |
| Seroquel (Quetiapine) | Common: |
| | Cardiovascular: Increased diastolic arterial pressure (Pediatric, 40.6%), Increased systolic arterial pressure (Pediatric, 15.2%), Orthostatic hypotension (Up to 7%), Tachycardia (Up to 6%) |
| | Endocrine metabolic: Serum cholesterol raised (7% to 18%), Serum triglycerides raised (8% to 28%), Weight gain (3% to 28%) |
| | Gastrointestinal: Abdominal pain (3% to 7%), Constipation (2% to 11%), Increased appetite (2% to 12%), Indigestion (2% to 7%), Nausea (Pediatric, 6% to 10%), Vomiting (Pediatric, 7% to 8%), Xerostomia (Adult, 9% to 44%; pediatric, 4% to 10%) |
| | Hepatic: Increased liver enzymes (1% to 6%) |
| | Musculoskeletal: Backache (3% to 5%) |
| | Neurologic: Asthenia (Up to 10%), Dizziness (8% to 19%), Extrapyramidal disease (1.1% to 12.9%), Headache (17% to 21%), Insomnia (8% to 12%), Lethargy (1% to 5%), Somnolence (18% to 57%), Tremor (2% to 8%) |
| | Psychiatric: Agitation (6% to 20%) |
| | Respiratory: Nasal congestion (3% to 5%), Pharyngitis (4% to 6%) |
| | Other: Fatigue (3% to 14%), Pain (7%) |
| | Serious: |
| | Cardiovascular: Prolonged QT interval (0.1% to less than 1%), Sudden cardiac death, Syncope (0.3% to 1%) |
| | Endocrine metabolic: Diabetic ketoacidosis |
| | Gastrointestinal: Pancreatitis |
| | Hematologic: Agranulocytosis, Leukopenia, Neutropenia (0.3% to 1.5%) |
| | Immunologic: Anaphylaxis |
| | Neurologic: Seizure (0.05% to 0.5%), Tardive dyskinesia |
| | Psychiatric: Suicidal thoughts |
| | Reproductive: Priapism |
| | Other: Neuroleptic malignant syndrome |
| Pain Relievers | |
| Opioids | |
| Codeine | Common |
| | Gastrointestinal: Constipation, Nausea, Vomiting |
| | Neurologic: Dizziness, Lightheadedness, Sedated, Somnolence |
| | Respiratory: Dyspnea |
| | Serious |
| | Cardiovascular: Hypotension |
| | Gastrointestinal: Bowel obstruction, Pancreatitis |
| | Neurologic: CSF pressure: raised, Seizure |
| | Respiratory: Respiratory depression |
| Fentanyl and Analogs | Common |
| | Cardiovascular: Hypotension (up to 5% (buccal film)), Peripheral edema (1% or greater (nasal spray); 5% to 32% (buccal tablet)) |
| | Dermatologic: Application site reaction (10% (buccal tablet)), Rash (3% to 8% (lozenge)) |
| | Endocrine metabolic: Abnormal weight loss (up to 13% (buccal tablet/film)), Hypokalemia (up to 15% (buccal tablet)) |

TABLE 4-continued

SAMPLE DRUGS AND THEIR SIDE EFFECTS

| | |
|---|---|
| | Gastrointestinal: Abdominal pain (1% or greater (nasal spray); up to 15%), Constipation (4% to 26%), Diarrhea (up to 16% (buccal tablet/film)), Loss of appetite (2% to 11% (buccal tablet/film)), Nausea (5.6% to 42%), Vomiting (4% to 37%)<br>Hematologic: Anemia (1% or greater (nasal spray); 9% to 32% (buccal tablet)), Neutropenia (1% or greater (nasal spray); up to 8% (buccal tablet))<br>Musculoskeletal: Arthralgia (up to 8% (buccal tablet)), Backache (up to 11% (buccal tablet))<br>Neurologic: Asthenia (up to 30% (lozenge, buccal tablet/film)), Confusion (up to 16%), Dizziness (6% (nasal spray); up to 26% (lozenge, sublingual, buccal tablet/film)), Headache (1% or greater (nasal spray); up to 17% (lozenge, sublingual, buccal tablet/film)), Insomnia (up to 11% (lozenge, buccal tablet/film)), Somnolence (up to 15% (sublingual, buccal tablet))<br>Psychiatric: Anxiety (3% to 9% (buccal film, lozenge)), Depression (up to 11% (buccal tablet))<br>Respiratory: Cough (up to 9%), Pneumonia (1% to 16% (buccal tablet, nasal spray))<br>Other: Dehydration (up to 21% (buccal tablet, film)), Fatigue (1% to 20% (buccal tablet, film))<br>Serious<br>Cardiovascular: Bradyarrhythmia (1% or greater (sublingual tablet)), Cardiorespiratory arrest (1% or greater (nasal spray)), Tachyarrhythmia (1% or greater (sublingual, buccal tablet/film))<br>Gastrointestinal: Bowel obstruction (1% or greater (buccal film); up to 4% (lozenge))<br>Hematologic: Deep venous thrombosis (1% or greater (nasal spray))<br>Musculoskeletal: Muscle rigidity<br>Respiratory: Dyspnea (up to 19% (lozenge, buccal tablet/film)), Respiratory depression |
| (Causing Overdoses) | |
| Hydrocodone | Common<br>Cardiovascular: Peripheral edema (1% to less than 5%%)<br>Dermatologic: Pruritus (0% to less than 5%)<br>Gastrointestinal: Abdominal pain (1% to less than 5%), Constipation (3% to 11%), Nausea (7% to 10%), Vomiting (3% to 6%), Xerostomia (1% to less than 5%)<br>Musculoskeletal: Spasm (1% to less than 5%)<br>Neurologic: Dizziness (2% to 3%), Headache (2% to 4%), Somnolence (1% to 5%), Tremor (3%)<br>Renal: Urinary tract infectious disease (1% to 5%)<br>Respiratory: Upper respiratory infection (1% to 3%)<br>Other: Fatigue (1% to 4%)<br>Serious<br>Cardiovascular: Hypotension (less than 1%), Orthostatic hypotension (less than 1%), Prolonged QT interval, Syncope<br>Gastrointestinal: Difficulty swallowing (less than 1%)<br>Neurologic: Raised intracranial pressure, Seizure<br>Respiratory: Respiratory depression<br>Other: Drug withdrawal syndrome in neonate of dependent mother, Opioid withdrawal (less than 1%) |
| Hydromorphone | Common<br>Dermatologic: Flushing (extended-release, less than 2%), Pruritus (extended-release, 1% to 8%), Sweating<br>Gastrointestinal: Constipation (extended-release, 7% to 31%), Nausea (extended-release, 9% to 28%.), Vomiting (extended-release, 6% to 14%)<br>Neurologic: Asthenia (1% to 11%), Dizziness (1% to 11%), Headache (1% to 12%), Somnolence (less than 2%)<br>Serious<br>Cardiovascular: Hypotension (less than 2%), Syncope (less than 2%)<br>Neurologic: Coma, Myoclonus (less than 2%), Raised intracranial pressure, Seizure (less than 2%)<br>Psychiatric: Suicidal thoughts (extended-release, less than 2%)<br>Respiratory: Apnea (less than 1%), Respiratory arrest, Respiratory depression (less than 2%)<br>Other: Drug dependence (less than 1%), Drug withdrawal (less than 1%), Neonatal Abstinence Syndrome |
| Methadone | Common<br>Cardiovascular: Hypotension<br>Endocrine metabolic: Diaphoresis<br>Gastrointestinal: Constipation, Nausea, Vomiting<br>Neurologic: Asthenia, Dizziness, Lightheadedness, Sedated<br>Serious |

TABLE 4-continued

SAMPLE DRUGS AND THEIR SIDE EFFECTS

|   |   |
|---|---|
|   | Cardiovascular: Decreased vascular flow, left ventricle, Prolonged QT interval, Torsades de pointes<br>Endocrine metabolic: Hypoglycemia<br>Respiratory: Respiratory acidosis, Respiratory arrest, Respiratory depression<br>Other: Drug dependence |
| Oxycodone | Common<br>Dermatologic: Pruritus (Adults, controlled-release, 13%; immediate-release, 3% or greater; pediatrics, 6%), Sweating (controlled-release, 5%; immediate-release, less than 3%)<br>Gastrointestinal: Abdominal pain (up to 5%), Constipation (Adults, controlled-release, 23%; immediate-release, 3% or greater; pediatrics, 9%), Nausea (Adults, controlled-release, 23%; immediate-release, 3% or greater; pediatrics, 15%), Vomiting (Adults, controlled-release, 12%; immediate-release, 3% or greater; pediatrics, 21%), Xerostomia (controlled-release, 6%; immediate-release, less than 3%)<br>Neurologic: Asthenia (controlled-release, 6%; immediate-release, 3% or greater), Dizziness (Adults, controlled-release, 13%; immediate-release, 3% or greater; pediatrics, 9%), Headache (Adults, 3% or greater; pediatrics, 14%), Somnolence (controlled-release, 23%; immediate-release, 3% or greater)<br>Other: Fever (Adults, up to 5%; pediatrics, 11%)<br>Serious<br>Cardiovascular: Cardiac arrest, Chest pain (less than 1%), Heart failure (less than 3%), Hypotension (less than 3%), Shock, ST segment depression (less than 1%), Syncope (less than 1%)<br>Gastrointestinal: Bowel obstruction, Diverticulitis, Exacerbation<br>Immunologic: Hypersensitivity reaction (less than 3%)<br>Respiratory: Respiratory depression<br>Other: Drug withdrawal syndrome in neonate of dependent mother, Opioid withdrawal (1% to 5%) |
| Oxymorphone | Common<br>Cardiovascular: Hypotension (less than 10%)<br>Dermatologic: Pruritus (less than or equal to 15.2%), Sweating symptom (1% to less than 10%)<br>Gastrointestinal: Abdominal pain (1% to less than 10%), Constipation (4.1% to 27.6%), Nausea (2.9% to 33.1%), Vomiting (less than or equal to 15.6%), Xerostomia (1% to less than 10%)<br>Neurologic: Confusion (1% to less than 10%), Dizziness (5% to 17%), Headache (4% to 12%), Somnolence (2% to 19%)<br>Respiratory: Dyspnea (1% to less than 10%), Hypoxia (less than 10%)<br>Other: Fatigue (1% to less than 10%), Fever (1% to 14.2%)<br>Serious<br>Gastrointestinal: Bowel obstruction (less than 1%)<br>Neurologic: Coma<br>Respiratory: Respiratory depression<br>Other: Drug dependence, Drug withdrawal syndrome in neonate of dependent mother |
| Amytal (amobarbital) | Common<br>Neurologic: Confusion, Dizziness, Headache, Somnolence<br>Serious<br>Dermatologic: Stevens-Johnson syndrome (rare)<br>Hematologic: Agranulocytosis (rare), Megaloblastic anemia, With prolonged use (rare)<br>Hepatic: Injury of liver, With prolonged use (rare)<br>Respiratory: Apnea, Hypoventilation |
| Nembutal (pentobarbital) | Common<br>Neurologic: Confusion (less than 1%), Dizziness (less than 1%), Somnolence (1% to 3%)<br>Psychiatric: Agitation (less than 1%)<br>Serious<br>Dermatologic: Stevens-Johnson syndrome (less than 1%)<br>Hematologic: Megaloblastic anemia (less than 1%)<br>Hepatic: Injury of liver (less than 1%)<br>Respiratory: Apnea (less than 1%), Hypoventilation (less than 1%) |
| Seconal (secobarbital) | Common<br>Neurologic: Somnolence (1% to 3%)<br>Serious<br>Hematologic: Megaloblastic anemia, With prolonged use (less than 1%)<br>Hepatic: Liver damage (less than 1%)<br>Psychiatric: Complex mannerisms - behavior (Less than 1%.)<br>Other: Drug dependence, Withdrawal sign or symptom |
| Adderall (Amphetamine) | Common<br>Cardiovascular: Increased systolic arterial pressure (extended-release: pediatrics, 7% to 35%) |

TABLE 4-continued

SAMPLE DRUGS AND THEIR SIDE EFFECTS

|  |  |
|---|---|
|  | Endocrine metabolic: Weight loss (extended-release: adults, 10%; pediatrics, 4% to 9%)<br>Gastrointestinal: Abdominal pain (extended-release: pediatrics, 11% to 14%), Loss of appetite (extended-release capsules: adults, 33%; pediatrics, 22% to 36%), Xerostomia (extended-release: adults, 35%; pediatrics, 2% to 4%)<br>Neurologic: Dizziness, Headache (extended-release: adults, 26%), Insomnia (extended-release: adults, 27%; pediatrics, 12% to 17%)<br>Psychiatric: Feeling nervous (extended release: adults, 13%; pediatrics, 6%)<br>Serious<br>Cardiovascular: Cardiomyopathy, Myocardial infarction, Peripheral vascular disease, Raynaud's disease, Sudden cardiac death<br>Dermatologic: Stevens-Johnson syndrome, Toxic epidermal necrolysis<br>Immunologic: Hypersensitivity reaction<br>Neurologic: Cerebrovascular accident, Seizure<br>Psychiatric: Psychotic disorder |
| Methylphenidate | Common<br>Cardiovascular: Tachycardia (Adult, 4.8%)<br>Dermatologic: Diaphoresis (Adult, 5.1%)<br>Endocrine metabolic: Weight decreased (Adult, 6.5%)<br>Gastrointestinal: Abdominal pain (2% or greater), Decrease in appetite (Adult, 25.3%; pediatric, 2% to 9% or greater), Loss of appetite (Adult, 1.7%; pediatric, 3.1% to 9% or greater), Nausea (Adult, 12.8%), Vomiting (2% or greater), Xerostomia (Adult, 14%)<br>Neurologic: Dizziness (Adult, 6.7%; pediatric, 1.9%.), Headache (Adult, 22.2%; pediatric, up to 12%), Insomnia (Adult, 12.3%; pediatric, 2.8% to 5%)<br>Psychiatric: Anxiety (Adult, 8.2%), Depression (Adult, 1.7% to 3.9%), Irritability (Adult, 5.8%)<br>Serious<br>Cardiovascular: Myocardial infarction, Raynaud's phenomenon, Sudden cardiac death<br>Endocrine metabolic: Decreased body growth<br>Gastrointestinal: Gastrointestinal obstruction, With preexisting severe gastrointestinal narrowing and use of controlled-release formulations<br>Hepatic: Abnormal liver function<br>Neurologic: Cerebral artery occlusion, Cerebral hemorrhage, Cerebrovascular accident, Seizure<br>Ophthalmic: Blurred vision (1.7% to 2% or greater)<br>Psychiatric: Aggressive behavior (Adult, 1.7%), Mania, Psychotic disorder<br>Reproductive: Priapism |
| Daytrana | See Methylphenidate |
| Concerta | See Methylphenidate |
| Ritalin | See Methylphenidate |
| Klonopin (clonazepam) | Common<br>Neurologic: Ataxia (5% to 30%), Coordination problem (6%), Dizziness (8%), Somnolence (37% to 50%)<br>Psychiatric: Problem behavior (25%)<br>Respiratory: Upper respiratory infection (8%)<br>Other: Fatigue (7%)<br>Serious<br>Psychiatric: Depression (7%), Suicidal thoughts<br>Respiratory: Respiratory depression |
| Valium (diazepam) | Common<br>Cardiovascular: Hypotension<br>Dermatologic: Rash (3%, rectal gel)<br>Gastrointestinal: Diarrhea (4%, rectal gel)<br>Musculoskeletal: Muscle weakness<br>Neurologic: Ataxia, Incoordination (3%, rectal gel), Somnolence<br>Psychiatric: Euphoria (3%, rectal gel)<br>Respiratory: Respiratory depression<br>Other: Fatigue<br>Serious<br>Hematologic: Neutropenia |
| Xanax (alprazolam) | Common<br>Endocrine metabolic: Decrease in appetite (7.3% to 27.8%), Increased appetite (7% to 32.7%), Weight increase (2.7% to 27.2%)<br>Gastrointestinal: Constipation (8.1% to 26.2%), Reduced salivation (32.8%), Xerostomia (10.2% to 14.7%)<br>Neurologic: Cognitive disorder (28.8%), Confusion (1.5% to 10.4%), Dysarthria (10.9% to 23.3%), Incoordination (9.4% to 40.1%), Lightheadedness (20.8%), Memory impairment (15.4% to 33.1%), Sedated (45.2%), Somnolence (23% to 76.8%) |

TABLE 4-continued

SAMPLE DRUGS AND THEIR SIDE EFFECTS

| | |
|---|---|
| | Psychiatric: Irritability (immediate-release, 33.1%; extended-release 1% or more)<br>Reproductive: Reduced libido (6% to 14.4%)<br>Other: Fatigue (13.9% to 48.6%)<br>Serious<br>Dermatologic: Stevens-Johnson syndrome |
| Ambien (zolpidem) | Common<br>Gastrointestinal: Diarrhea (1% to 3%), Nausea (1% to 7%)<br>Immunologic: Allergic reaction (4%)<br>Neurologic: Dizziness (1% to 23.5%), Drugged state (3%), Headache (1% to 19%), Somnolence (2% to 15%)<br>Ophthalmic: Visual disturbance (3%)<br>Other: Fatigue (0.1% to 3%)<br>Serious<br>Cardiovascular: Chest pain (1%), Tachycardia (0.1% to 1%)<br>Immunologic: Anaphylaxis (rare)<br>Neurologic: Hepatic encephalopathy<br>Psychiatric: Complex mannerisms - behavior, Depression, worsening, Suicidal thoughts<br>Other: Angioedema (rare) |
| Lunesta (eszopiclone) | Common<br>Gastrointestinal: Disorder of taste (8% to 34%), Vomiting (3%)<br>Neurologic: Dizziness (1% to 7%), Headache (13% to 21%), Migraine (1% or greater)<br>Respiratory: Respiratory tract infection (5% to 10%)<br>Serious<br>Other: Angioedema (rare) |
| Sonata (zaleplon) | Common<br>Neurologic: Dizziness (7% to 9%), Headache (30% to 42%)<br>Serious<br>Immunologic: Anaphylaxis (rare)<br>Neurologic: Drug withdrawal seizure (rare)<br>Psychiatric: Abnormal behavior, Complex mannerisms - behavior, Depression (at least 1%), Suicidal behavior, Suicidal thoughts<br>Other: Angioedema (rare) |
| Chantix | Common<br>Gastrointestinal: Constipation (5% to 8%), Flatulence (6% to 9%), Nausea (30%), Vomiting (5% to 11%)<br>Neurologic: Dream disorder (9% to 13%), Headache (11% to 19%), Insomnia (10% to 19%)<br>Serious<br>Cardiovascular: Angina (2.3%), Myocardial infarction (2%)<br>Neurologic: Cerebrovascular accident<br>Ophthalmic: Acquired night blindness (rare), Blurred vision (infrequent), Retinal vascular disorder (rare), Subcapsular cataract (rare), Transient blindness (rare), Visual disturbance (infrequent)<br>Psychiatric: Abnormal behavior, Depression (3.5% to 11%), Hostile behavior (2%), Mood disorder (2.3%), Suicidal behavior, and/or ideation (6% to 11%) |
| Revlimid | Common<br>Cardiovascular: Peripheral edema (multiple myeloma, 26.3%; myelodysplastic syndrome, 20.3%; mantle cell lymphoma, 16%)<br>Dermatologic: Pruritus (Multiple myeloma, 7.6%; myelodysplastic syndrome, 41.9%; mantle cell lymphoma, 17%), Rash (Multiple myeloma, up to 26.1%; myelodysplastic syndrome, 35.8%; mantle cell lymphoma, 22%)<br>Endocrine metabolic: Hypokalemia (Multiple myeloma, 13.6% to 17.1%; myelodysplastic syndrome, 10.8%; mantle cell lymphoma, 13%), Weight decreased (13% to 19.5%)<br>Gastrointestinal: Constipation (Multiple myeloma, 40.5%; myelodysplastic syndrome, 23.6%; mantle cell lymphoma, 16%), Diarrhea (Multiple myeloma, 38.5% to 45.5%; myelodysplastic syndrome, 48.6%; mantle cell lymphoma, 31%), Nausea (23.6% to 30%')<br>Hematologic: Anemia, All grades (Multiple myeloma, 31.4% to 43.8%; myelodysplastic syndrome, 11.5%; mantle cell lymphoma, 31%), Leukopenia, All grades (7.9% to 15%), Neutropenia, All grades (Multiple myeloma, 35% to 42.2%; myelodysplastic syndrome, 58.8%; mantle cell lymphoma, 49%), Thrombocytopenia, All grades (Multiple myeloma, 19.5% to 21.5%; myelodysplastic syndrome, 61.5%; mantle cell lymphoma, 36%)<br>Musculoskeletal: Arthralgia (Multiple myeloma, 19%; myelodysplastic syndrome, 21.6%; mantle cell lymphoma, 8%), Backache (Multiple myeloma, 25.8% to 32%; myelodysplastic syndrome, 20.9%; mantle cell lymphoma, 13%), Cramp (Multiple myeloma, 33.4%; myelodysplastic syndrome, 18.2%) |

TABLE 4-continued

SAMPLE DRUGS AND THEIR SIDE EFFECTS

|  |  |
|---|---|
|  | Neurologic: Asthenia (Multiple myeloma, 28.2%; myelodysplastic syndrome, 14.9%; mantle cell lymphoma, 14%), Dizziness (19.6% to 23.2%), Headache (Myelodysplastic syndrome, 19.6%), Insomnia (Multiple myeloma, 27.6%; myelodysplastic syndrome, 10.1%), Tremor (Multiple myeloma, 21.2%) Ophthalmic: Blurred vision (Multiple myeloma, 17.3%) Respiratory: Cough (Multiple myeloma, 22.7%; myelodysplastic syndrome, 19.6%; mantle cell lymphoma, 28%), Dyspnea (Multiple myeloma, 22% to 23.5%; myelodysplastic syndrome, 6.8% to 16.9%; mantle cell lymphoma, 18%), Epistaxis (Myelodysplastic syndrome, 14.9%), Nasopharyngitis (Multiple myeloma, 15% to 17.6%; myelodysplastic syndrome, 23%), Pharyngitis (13.6% to 15.5%), Upper respiratory infection (Multiple myeloma, 24.6%; myelodysplastic syndrome, 14.9%; mantle cell lymphoma, 13%) Other: Fatigue (Multiple myeloma, 32.5% to 43.9%; myelodysplastic syndrome, 31.1%; mantle cell lymphoma, 34%), Fever (Multiple myeloma, 21.4% to 27.5%; myelodysplastic syndrome, 20.9%; mantle cell lymphoma, 23%), Infectious disease Serious Cardiovascular: Atrial fibrillation, Grade 3 or 4 (multiple myeloma, 3.7%), Cerebrovascular accident (1.4% to 2.3%), Congestive heart failure, Grade 3 or 4 (multiple myeloma, 1.4%), Myocardial infarction (Less than 5%), Syncope, Grade 3 or 4 (1.4% to 2.8%) Dermatologic: Stevens-Johnson syndrome, Toxic epidermal necrolysis Hematologic: Anemia, Grade 3 or 4 (Multiple myeloma, 9.9% to 18.2%; myelodysplastic syndrome, 6.1%; mantle cell lymphoma, 11%), Deep venous thrombosis, All grades (9.3% to 10.3%), Deep venous thrombosis, Grade 3 or 4 (4% to 8.2%), Febrile neutropenia, Grade 3 or 4 (2.3% to 6%), Leukopenia, Grade 3 or 4 (4% to 7%), Neutropenia, Grade 3 or 4 (Multiple myeloma, 16% to 33.4% myelodysplastic syndrome, 53.4%; mantle cell lymphoma, 43%.), Thrombocytopenia, Grade 3 or 4 (Multiple myeloma, 8.3% to 12.2%; myelodysplastic syndrome, 50%; mantle cell lymphoma, 28%), Thrombosis Hepatic: Hepatotoxicity (15%), Liver failure Ophthalmic: Cataract, Grade 3 or 4 (Multiple myeloma, 9.6%; 1.4% (grade 3.4)) Renal: Interstitial nephritis, acute Respiratory: Hypoxia (Mantle cell lymphoma, 2%), Pleural effusion (Mantle cell lymphoma, 7%), Pneumonia (Multiple myeloma, 13.6% to 17.5%; myelodysplastic syndrome, 11.5%; mantle cell lymphoma, 14%), Pneumonitis (Myelodysplastic syndrome, grade 3 or 4, 1.4%), Pulmonary embolism, Grade 3 or 4 (2% to 4%), Pulmonary hypertension (Myelodysplastic syndrome, grade 3 or 4, 1.4%), Respiratory distress (Grade 3 or 4, 1% to 2%) Other: Angioedema, Multiple organ failure (Myelodysplastic syndrome, grade 3 or 4, 1.4%), Secondary malignant neoplastic disease, Tumor flare (Mantle cell lymphoma, 10%), Tumor lysis syndrome |
| Tracleer | Common Cardiovascular: Edema of lower extremity (5% to 8%), Hypotension (7%), Palpitations (5%) Dermatologic: Flushing (7% to 14%) Hematologic: Decreased hemoglobin (6%) Neurologic: Headache (up to 24%) Serious Hematologic: Decreased hemoglobin (Severe) (3%) Hepatic: Cirrhosis of liver, Increased liver aminotransferase level (Up to 11%), Liver failure Other: Angioedema |
| Xeljanz (Jak Compounds) | Common Endocrine metabolic: Increased HDL level (10% to 12%), Raised low density lipoprotein cholesterol (15% to 19%) Neurologic: Headache (3.4% to 4.3%) Renal: Urinary tract infectious disease (2%) Respiratory: Nasopharyngitis (2.8% to 3.8%), Upper respiratory infection (3.8% to 4.5%) Serious Dermatologic: Skin cancer, Non-melanoma Gastrointestinal: Gastrointestinal perforation Hematologic: Anemia, Decreased lymphocyte count (0.04%), Neutropenia (0.07%) Hepatic: Injury of liver Immunologic: Infectious disease (20% to 22%), Opportunistic infection, Post-transplant lymphoproliferative disorder, Epstein Barr virus associated (2.3%), Tuberculosis Other: Cancer |

TABLE 4-continued

SAMPLE DRUGS AND THEIR SIDE EFFECTS

| | |
|---|---|
| Atomoxetine (Strattera) | Common<br>Cardiovascular: Increased diastolic arterial pressure (adult, 4.8% to 12.6%; pediatric, 9.3% to 21.5%), Increased systolic arterial pressure (adult, 4.2% to 12.4%; pediatric, 4.9% to 12.5%), Tachycardia (adult, 1.5% to 22.4%; pediatric, 0.3% to 23.4%)<br>Endocrine metabolic: Weight decreased (adults, 2%; pediatric, 3% to 29.1%)<br>Gastrointestinal: Abdominal pain (adult, 7%; pediatric, 17% to 18%), Constipation (adult, 8%; pediatric, 1% to 2%), Decrease in appetite (adult, 16%; pediatric, 16%), Nausea (adult, 26%; pediatric, 7% to 13%), Vomiting (adult, 4%; pediatric, 11%), Xerostomia (adult, 20%)<br>Neurologic: Headache (pediatric, 19%), Insomnia (adult, 15%; pediatric, at least 2%), Somnolence (adult, 8%; pediatric, 11%)<br>Renal: Delay when starting to pass urine (adult, 6%)<br>Reproductive: Dysmenorrhea (adult, 3%), Erectile dysfunction (adult, 8%)<br>Other: Menopausal flushing (adult, 3%)<br>Serious<br>Cardiovascular: Myocardial infarction, Sudden cardiac death<br>Hepatic: Injury of liver (Severe), Liver failure<br>Neurologic: Cerebrovascular accident, Dyskinesia, Seizure (adult, 0.1%; pediatric, 0.2%)<br>Psychiatric: Mania, Psychotic disorder, Suicidal thoughts (pediatric, 0.4%)<br>Reproductive: Priapism (rare) |
| Quetiapine (Seroquel) | See Seroquel above |
| Eszopiclone (Lunesta) | See Lunesta above |
| Gabapentin (Neurontin) | Common<br>Cardiovascular: Peripheral edema (1.7% to 8.3%)<br>Gastrointestinal: Nausea (greater than 1%), Vomiting (3.3%)<br>Immunologic: Viral disease (10.9%)<br>Neurologic: Ataxia (Adult, 3%; adult and adolescent, 13%), Nystagmus (Adult and adolescent, 8%)<br>Other: Fatigue (3% to 11%), Fever (Pediatric, 10%)<br>Serious<br>Dermatologic: Stevens-Johnson syndrome<br>Immunologic: Drug hypersensitivity syndrome<br>Neurologic: Dizziness (Adults, 28%; adults and adolescents, 17%; pediatrics, 3%), Somnolence (Adults, 21%; adults and adolescents, 19%; pediatrics, 8%)<br>Psychiatric: Disorder of form of thought (Pediatric, 1.7%), Disturbance in thinking (2% to 3%), Hostile behavior (Pediatric, 5.2%), Hyperactive behavior (Pediatric, 4.7%), Mood swings (Pediatric, 6%), Suicidal thoughts |
| Topiramate (Topamax) | Common<br>Dermatologic: Flushing (pediatrics, 5%)<br>Endocrine metabolic: Serum bicarbonate level abnormal (25% to 67%)<br>Gastrointestinal: Loss of appetite (10% to 24%), Weight decreased (4% to 21%)<br>Immunologic: Infectious disease (2% to 8%)<br>Neurologic: Confusion (3% to 11%), Dizziness (4% to 25%), Impaired cognition (2% to 7%), Impaired psychomotor performance (2% to 13%), Memory impairment (3% to 12%), Paresthesia (1% to 51%), Reduced concentration span (2% to 10%), Somnolence (6% to 29%)<br>Psychiatric: Feeling nervous (4% to 16%), Mood disorder (4% to 11%)<br>Other: Fatigue (6% to 16%), Fever (1% to 12%)<br>Serious<br>Dermatologic: Erythema multiforme, Stevens-Johnson syndrome, Toxic epidermal necrolysis<br>Endocrine metabolic: Hyperammonemia (Adolescents, 26%), Hypohidrosis, Increased body temperature, Metabolic acidosis<br>Hepatic: Liver failure<br>Neurologic: Drug-induced encephalopathy<br>Ophthalmic: Glaucoma, Myopia, Visual field defect (epilepsy, 0.1% to 1%)<br>Psychiatric: Suicidal thoughts<br>Renal: Nephrolithiasis (adults, 1% to 3%) |
| Lamotrigine (Lamictal) | Common<br>Dermatologic: Rash (7% to 14%)<br>Gastrointestinal: Abdominal pain (immediate-release, 5% to 10%), Diarrhea (immediate-release, 6% to 11%; extended-release, 5%), Indigestion (immediate-release, 2% to 7%), Nausea (immediate-release, 7% to 25%; extended-release, 7%), Vomiting (immediate-release, 5% to 20%; extended-release, 6%)) |

TABLE 4-continued

SAMPLE DRUGS AND THEIR SIDE EFFECTS

|  |  |
|---|---|
|  | Neurologic: Asthenia (immediate-release, 2% to 8%; extended-release, 6%), Ataxia (immediate-release, 2% to 11%), Coordination problem (immediate-release, 6% to 7%; extended-release, 3%), Dizziness (immediate-release, 7% to 54%; extended release, 14%), Headache (immediate-release, 29%), Insomnia (immediate-release, 5% to 10%), Somnolence (immediate-release, 9% to 17%; extended-release, 5%), Tremor (immediate-release, 4% to 10%; extended-release, 6%), Vertigo (immediate-release, 2%; extended-release, 3%)<br>Ophthalmic: Blurred vision (immediate-release, 11% to 25% (adults) and 4% (children); extended-release, 3%), Diplopia (immediate-release, 24% to 49% (adults) and 5% (children); extended-release, 5%)<br>Psychiatric: Anxiety (immediate-release, 4%; extended-release, 3%), Depression (immediate-release, 4%; extended-release, 3%)<br>Reproductive: Dysmenorrhea (immediate-release, 5% to 7%)<br>Respiratory: Rhinitis (immediate-release, 7% to 14%)<br>Other: Pain (immediate-release, 5%)<br>Serious<br>Dermatologic: Erythema multiforme (less than 0.1%), Rash, Serious (0.08% to 0.8%), Stevens-Johnson syndrome (0.08% to 0.8%.), Toxic epidermal necrolysis (0.08% to 0.8%)<br>Hematologic: Anemia (immediate release, less than 0.1%), Disseminated intravascular coagulation, Eosinophilia (immediate release, less than 0.1%), Leukopenia (immediate release, 0.1% to 1%), Thrombocytopenia (immediate release, less than 0.1%)<br>Hepatic: Liver failure<br>Immunologic: Drug hypersensitivity syndrome<br>Neurologic: Aseptic meningitis<br>Other: Angioedema (less than 0.1%), Neuroleptic malignant syndrome |
| Levetiracetam (Keppra) | Common<br>Gastrointestinal: Loss of appetite (3% to 8%), Vomiting (15%)<br>Immunologic: Infectious disease (13%)<br>Musculoskeletal: Decreased bone mineral density (70%), Neck pain (2% to 8%)<br>Neurologic: Asthenia (15%), Dizziness (5% to 9%), Headache (14% to 19%)<br>Psychiatric: Abnormal behavior (7% to 37.6%), Irritability (6% to 12%)<br>Respiratory: Cough (2% to 9%), Nasopharyngitis (7% to 15%)<br>Other: Fatigue (10% to 11%)<br>Serious<br>Dermatologic: Stevens-Johnson syndrome, Toxic epidermal necrolysis due to drug<br>Hematologic: Decreased erythrocyte production, Decreased white blood cell count (2.4% to 3.2%), Eosinophilia (8.6%), Neutropenia (partial onset seizures, adults, 2.4%), Pancytopenia, Thrombocytopenia<br>Hepatic: Liver failure<br>Neurologic: Somnolence (8% to 45%)<br>Psychiatric: Suicidal intent (0.5%), Suicide |
| Olanzapine (Zyprexa) | Common<br>Cardiovascular: Orthostatic hypotension (More than 5%), Peripheral edema (3% to 6%)<br>Endocrine metabolic: Hypercholesterolemia (Adult, up to 26%; adolescent, up to 53%), Hyperglycemia (Adult, up to 20%; adolescent, up to 14%), Hyperprolactinemia (30% to 61.1%), Increased appetite (Adult, 3% to 24%; adolescent, 17% to 29%), Serum triglycerides raised (20.8% to 40%), Weight increased, 7% or greater (Adult, 22.2% to 64%; adolescent, 40.6% to 89%)<br>Gastrointestinal: Constipation (4% to 11%), Xerostomia (Adult, up to 32%; adolescent, 4% to 7%)<br>Neurologic: Akathisia (5% to 27%), Asthenia (2% to 20%), Dizziness (Adult, 1.6% to 18%; adolescent, 7% to 8%), Somnolence (IM, 6%; oral, 20% to 52%), Tremor (1% to 23%)<br>Psychiatric: Personality disorder (8%)<br>Serious<br>Cardiovascular: Sudden cardiac death<br>Endocrine metabolic: Diabetes mellitus, Diabetic coma with ketoacidosis, Diabetic ketoacidosis, Hyperglycemic hyperosmolar state<br>Gastrointestinal: Acute hemorrhagic pancreatitis<br>Hematologic: Leukopenia, Venous thromboembolism<br>Immunologic: Hypersensitivity reaction |
| Risperidone (Risperdal) | Common<br>Dermatologic: Rash (oral, adults, 1% to 4%; pediatrics, up to 11%; IM, less than 4%) |

TABLE 4-continued

SAMPLE DRUGS AND THEIR SIDE EFFECTS

|  |  |
|---|---|
|  | Endocrine metabolic: Hyperprolactinemia (oral, adults, less than 1%; pediatrics, 49% to 87%; IM, less than 4%), Weight increased (oral, adult, 8.7% to 20.9%; pediatric, 14% to 32.6%; IM, adult, 8% to 10%)<br>Gastrointestinal: Constipation (oral, 8% to 21%; IM, 5% to 7%), Diarrhea (oral, 1% to 8%; IM, less than 4%), Excessive salivation (oral, 1% to 10%; IM, 1% to 4%), Increased appetite (oral, adult, more than 5%; pediatric, 4% to 47%; IM, 4%), Indigestion (oral, 2% to 10%; IM, 6%), Nausea (oral, 4% to 16%; IM, 3% to 4%), Upper abdominal pain (oral, adult, more than 5%; pediatric, 13% to 16%), Vomiting (oral, 10% to 25%; IM, less than 4%), Xerostomia (oral, 4% to 15%; IM, up to 7%)<br>Neurologic: Akathisia (oral, up to 10%; IM, 4% to 11%), Dizziness (oral, 4% to 16%; IM, 3% to 11%), Dystonia (oral, adult, 3% to 5%; pediatric, 2% to 6%; IM, adult, less than 4%), Parkinsonism (oral, 6% to 28%; IM, 8% to 15%), Sedated (oral, adult, 3% to 6%; pediatric, 8% to 29%), Tremor (oral, 2% to 12%; IM, 3% to 24%)<br>Ophthalmic: Blurred vision (oral, 1% to 7%; IM, 2% to 3%)<br>Psychiatric: Anxiety (oral, up to 16% IM, less than 4%)<br>Respiratory: Cough (oral, adults, 2%; pediatrics, 24%; IM, 2% to 4%), Nasal congestion (oral, adult, 4% to 6%; pediatric, 13%), Nasopharyngitis (oral, adult, 3% to 4%; pediatric, 21%), Pain in throat (oral, adult, more than 5%; pediatric, 3% to 10%), Upper respiratory infection (oral, 2% to 8%; IM, 2% and 6%)<br>Other: Fatigue (oral, adult, 1% to 3%; pediatric, 18% to 42%; IM, 3% to 9%), Pain, General (IM, 1% to 4%)<br>Serious<br>Cardiovascular: Prolonged QT interval, Sudden cardiac death, Syncope (oral, up to 1%; IM, up to 2%)<br>Endocrine metabolic: Diabetic ketoacidosis, Hypothermia<br>Gastrointestinal: Pancreatitis<br>Hematologic: Agranulocytosis, Leukopenia, Neutropenia, Thrombocytopenia, Thrombotic thrombocytopenic purpura<br>Neurologic: Cerebrovascular accident (oral, less than 5%; IM, less than 4%), Seizure (oral, 0.3%; IM, 0.3%), Tardive dyskinesia (oral, less than 5%; IM, less than 4%)<br>Reproductive: Priapism<br>Respiratory: Pulmonary embolism<br>Other: Neuroleptic malignant syndrome (oral, adults, less than 1%; pediatrics, less than 5%) |
| Hydrocodone/<br>APAP (Generics) | Common<br>Gastrointestinal: Nausea and vomiting<br>Neurologic: Dizziness, Lightheadedness, Sedated<br>Serious<br>Dermatologic: Acute generalized exanthematous pustulosis, Stevens-Johnson syndrome, Toxic epidermal necrolysis<br>Hematologic: Agranulocytosis, Thrombocytopenia<br>Hepatic: Hepatotoxicity, Liver failure<br>Respiratory: Respiratory depression |
| Tramadol (Ultram) | Common<br>Dermatologic: Flushing (7.7% to 15.8%), Pruritus (3% to 11.9%)<br>Gastrointestinal: Constipation (10% to 46%), Nausea (13% to 40%), Vomiting (3% to 17%), Xerostomia (1% to 10%)<br>Neurologic: Dizziness (7% to 33%), Headache (3% to 32%), Insomnia (1% to 10.9%), Somnolence (4% to 25%)<br>Serious<br>Cardiovascular: Myocardial infarction (0.5% to less than 1%)<br>Endocrine metabolic: Hypoglycemia (Very rare)<br>Gastrointestinal: Pancreatitis (0.5% to less than 1%)<br>Immunologic: Anaphylactoid reaction (less than 1%)<br>Neurologic: Seizure<br>Respiratory: Dyspnea (less than 5%), Respiratory depression<br>Other: Serotonin syndrome (less than 1%) |
| Oxycodone/APAP (Percocet) | Common<br>Gastrointestinal: Constipation (extended-release, 4%), Nausea (extended-release, 31%), Vomiting (extended-release, 9%)<br>Neurologic: Dizziness (extended-release, 13%), Headache (extended-release, 10%), Lightheadedness, Sedated, Somnolence (extended-release, 4%)<br>Serious<br>Cardiovascular: Disorder of pulmonary circulation, Hypotension, Shock<br>Dermatologic: Acute generalized exanthematous pustulosis, Stevens-Johnson syndrome, Toxic epidermal necrolysis<br>Hematologic: Agranulocytosis, Neutropenia<br>Hepatic: Hepatic necrosis, Hepatotoxicity, Liver failure<br>Immunologic: Anaphylaxis, Hypersensitivity reaction |

TABLE 4-continued

SAMPLE DRUGS AND THEIR SIDE EFFECTS

| | |
|---|---|
| | Respiratory: Apnea, Respiratory arrest, Respiratory depression |
| | Other: Neonatal Abstinence Syndrome |
| Oxycodone (OxyContin) | See Oxycodone above |
| Codeine/APAP (Tylenol #2) | Common |
| | Gastrointestinal: Nausea, Vomiting |
| | Neurologic: Dizziness, Lightheadedness, Sedated, Somnolence |
| | Serious |
| | Dermatologic: Acute generalized exanthematous pustulosis, Stevens-Johnson syndrome, Toxic epidermal necrolysis |
| | Hematologic: Agranulocytosis, Thrombocytopenia |
| | Hepatic: Liver failure |
| | Immunologic: Hypersensitivity reaction |
| | Respiratory: Respiratory depression |
| Alprazolam (Xanax) | See Alprazolam above |
| Clonazepam (Klonopin) | See Clonazepam above |
| Diazepam (Valium) | See Diazepam above |
| Lorazepam (Ativan) | Common |
| | Neurologic: Asthenia (4.2%), Dizziness (6.9%), Sedated (15.9%), Unsteadiness present (3.4%) |
| | Psychiatric: Depression |
| | Serious |
| | Endocrine metabolic: Acidosis (less than 1%) |
| | Psychiatric: Delirium |
| Buspirone (Buspar) | Common |
| | Gastrointestinal: Nausea (8%) |
| | Neurologic: Dizziness (12%), Headache (6%), Somnolence (10%) |
| | Psychiatric: Feeling nervous (5%) |
| | Serious |
| | Cardiovascular: Congestive heart failure (less than 0.1%), Myocardial infarction (less than 0.1%) |
| | Neurologic: Cerebrovascular accident (less than 0.1%) |
| Hydroxyzine (Vistaril) | Common |
| | Gastrointestinal: Xerostomia |
| | Neurologic: Headache, Somnolence |
| Escitalopram (Lexapro) | Common |
| | Dermatologic: Diaphoresis (3% to 8%) |
| | Gastrointestinal: Abdominal pain (2%), Constipation (3% to 6%), Diarrhea (6% to 14%), Indigestion (2% to 6%), Nausea (15% to 18%), Vomiting (up to 3%), Xerostomia (4% to 9%) |
| | Neurologic: Dizziness (4% to 7%), Headache (24%), Insomnia (7% to 14%), Somnolence (4% to 13%) |
| | Reproductive: Disorder of ejaculation (9% to 14%), Erectile dysfunction (3%), Orgasm incapacity (females, 2% to 6%), Reduced libido (3% to 7%) |
| | Other: Fatigue (5% to 8%) |
| | Serious |
| | Psychiatric: Depression, worsening, Suicidal thoughts, Suicide |
| | Other: Serotonin syndrome |
| Sertraline (Zoloft) | Common |
| | Gastrointestinal: Constipation (3% to 8%), Diarrhea (13% to 24%), Indigestion (6% to 13%), Nausea (13% to 30%), Nausea and vomiting (2% to 30%) |
| | Neurologic: Dizziness (6% to 17%), Headache (25%), Insomnia (12% to 28%), Somnolence (2% to 15%), Tremor (5% to 11%) |
| | Reproductive: Abnormal ejaculation (7% to 19%), Reduced libido (up to 11%) |
| | Other: Fatigue (10% to 16%) |
| | Serious |
| | Dermatologic: Stevens-Johnson syndrome |
| | Endocrine metabolic: Hyponatremia |
| | Gastrointestinal: Gastrointestinal hemorrhage |
| | Immunologic: Anaphylaxis |
| | Musculoskeletal: Rhabdomyolysis |
| | Neurologic: Seizure (rare) |
| | Psychiatric: Depression, Exacerbation, Mania (rare), Suicidal thoughts (rare), Suicide (rare) |
| | Other: Serotonin syndrome |
| Trazodone (Desyrel) | Common |
| | Gastrointestinal: Constipation (7% to 8%), Diarrhea (up to 9%), Nausea (21%), Vomiting (at least 1%), Xerostomia (14% to 33.8%) |
| | Musculoskeletal: Backache (5%) |
| | Neurologic: Confusion (up to 5.7%), Dizziness (25%), Headache (9.9% to 33%), Insomnia (6.4% to 9.9%), Somnolence (23.9% to 46%) |
| | Ophthalmic: Blurred vision (5% to 14.7%) |
| | Psychiatric: Dream disorder (up to 5.1%), Feeling nervous (6.4% to 14.8%) |
| | Other: Fatigue (5.7% to 15%) |

TABLE 4-continued

SAMPLE DRUGS AND THEIR SIDE EFFECTS

| | |
|---|---|
| | Serious<br>Cardiovascular: Cardiac dysrhythmia, Hypotension (3.8% to 7%), Prolonged QT interval, Torsades de pointes<br>Immunologic: Hypersensitivity reaction (less than 1%)<br>Neurologic: Seizure (rare), Serotonin syndrome<br>Psychiatric: Suicidal thoughts (rare), Suicide<br>Reproductive: Priapism |
| Duloxetine (Cymbalta) | Common<br>Cardiovascular: Hypertension (2%)<br>Dermatologic: Diaphoresis (Adult, 6%; pediatric, less than 2%)<br>Gastrointestinal: Constipation (9% to 10%), Decrease in appetite (6% to 10%), Diarrhea (Adult, 9%; pediatric, 6%), Nausea (18% to 23%), Xerostomia (Adult, 11% to 14%; pediatric, 2%)<br>Neurologic: Asthenia, Dizziness (Adult, 9%; pediatric, 8%), Headache (Adult, 13% to 14%; pediatric, 18%), Hypersomnia, Insomnia (7% to 10%), Sedated, Somnolence<br>Other: Fatigue<br>Serious<br>Cardiovascular: Hypertensive crisis, Myocardial infarction (0.01% to 0.001%), Orthostatic hypotension<br>Dermatologic: Stevens-Johnson syndrome<br>Gastrointestinal: Gastrointestinal hemorrhage<br>Hematologic: Bleeding, Abnormal<br>Hepatic: Liver failure<br>Psychiatric: Suicidal thoughts<br>Other: Serotonin syndrome, Withdrawal sign or symptom (1% or greater) |
| Citalopram (Celexa) | Common<br>Dermatologic: Diaphoresis (5% to 18%)<br>Gastrointestinal: Constipation (13%), Diarrhea (8%), Nausea (20% to 21%), Vomiting (4% to 20%), Xerostomia (17% to 20%)<br>Neurologic: Dizziness (14%), Headache (18%), Insomnia (15%), Sedated (15%), Somnolence (18%), Tremor (8% to 16%)<br>Psychiatric: Agitation (3% to 10%)<br>Reproductive: Disorder of ejaculation (6.1%)<br>Other: Fatigue (5%)<br>Serious<br>Cardiovascular: Myocardial infarction (0.1% to 1%), Prolonged QT interval (0.5% to 1.9%), Torsades de pointes<br>Neurologic: Cerebrovascular accident (0.1% to less than 1%)<br>Psychiatric: Suicidal thoughts, Suicide<br>Other: Serotonin syndrome |
| Aripiprazole (Abilify) | Common<br>Endocrine metabolic: Weight increased, 7% or greater (2.5% to 21.5%)<br>Gastrointestinal: Constipation (5% to 11%), Nausea (8% to 15%), Vomiting (3% to 11%)<br>Neurologic: Akathisia (2% to 25%), Dizziness (4% to 10%), Extrapyramidal sign (2% to 27.3%), Headache (10% to 27%), Insomnia (8% to 18%), Sedated (3% to 21%), Somnolence (6% to 26.3%), Tremor (2% to 11.8%)<br>Ophthalmic: Blurred vision (3% to 8%)<br>Psychiatric: Anxiety (4% to 17%), Restlessness (2% to 12%)<br>Other: Fatigue (2% to 17%)<br>Serious<br>Cardiovascular: Cardiorespiratory arrest (0.1% to 1%), Cardiorespiratory failure (0.1% to 1%), Myocardial infarction (0.1% to 1%), Prolonged QT interval (0.1% to 1%)<br>Endocrine metabolic: Diabetic ketoacidosis (Less than 0.1%)<br>Gastrointestinal: Pancreatitis (Lss than 0.1%)<br>Hematologic: Agranulocytosis, Leukopenia (Less than 1%), Neutropenia (Less than 1%)<br>Musculoskeletal: Rhabdomyolysis (Less than 0.1%)<br>Neurologic: Cerebrovascular accident, Seizure (Up to 0.3%), Tardive dyskinesia, Transient ischemic attack<br>Psychiatric: At risk for suicide, Suicidal behavior<br>Other: Angioedema (0.1% to less than 1%), Increased body temperature, Neuroleptic malignant syndrome |
| Paroxetine (Paxil) | Common<br>Cardiovascular: Palpitations (up to 3%), Vasodilatation (2% to 4%)<br>Dermatologic: Diaphoresis (5% to 14%)<br>Gastrointestinal: Constipation (up to 16%), Diarrhea (up to 18%), Loss of appetite (up to 9%), Nausea (up to 26%), Xerostomia (9% to 18%)<br>Neurologic: Asthenia (up to 22%), Dizziness (6% to 14%), Headache (17% to 27%), Insomnia (up to 24%), Somnolence (up to 24%), Tremor (4% to 11%)<br>Ophthalmic: Blurred vision (up to 5%) |

TABLE 4-continued

SAMPLE DRUGS AND THEIR SIDE EFFECTS

|  |  |
|---|---|
|  | Reproductive: Abnormal ejaculation (13% to 28%), Erectile dysfunction (2% to 9%), Orgasm disorder (females; 2% to 9%), Reduced libido (males: 6% to 15%; females: 0% to 9%)<br>Respiratory: Yawning (4%)<br>Serious<br>Dermatologic: Stevens-Johnson syndrome, Toxic epidermal necrolysis<br>Hepatic: Acute hepatitis (rare)<br>Neurologic: Seizure (0.1%)<br>Psychiatric: Depression, exacerbation, Suicidal thoughts (rare), Suicide (rare)<br>Other: Serotonin syndrome |
| Fluoxetine (Prozac) | Common<br>Gastrointestinal: Diarrhea (8% to 18%), Indigestion (6% to 10%), Loss of appetite (3.8% to 17%), Nausea (12% to 29%), Xerostomia (4% to 12%)<br>Neurologic: Asthenia (7% to 21%), Dizziness (2% to 11%), Insomnia (9% to 33%), Somnolence (5% to 17%), Tremor (3% to 13%)<br>Psychiatric: Anxiety (3% to 15%), Feeling nervous (3% to 14%)<br>Respiratory: Pharyngitis (3% to 11%), Rhinitis (16% to 23%)<br>Other: Influenza-like symptoms (3% to 12%)<br>Serious<br>Cardiovascular: Prolonged QT interval<br>Dermatologic: Erythema multiforme<br>Endocrine metabolic: Hyponatremia<br>Hematologic: Bleeding<br>Immunologic: Anaphylactoid reaction<br>Neurologic: Seizure (0.2%)<br>Psychiatric: Depression, worsening, Mania, Suicidal thoughts, Suicide<br>Other: Serotonin syndrome |
| Venlafaxine (Effexor) | Common<br>Cardiovascular: Hypertension (3% to 13%)<br>Dermatologic: Sweating symptom (6.7% to 25%)<br>Endocrine metabolic: Weight loss (3% to 47%)<br>Gastrointestinal: Constipation (8% to 15%), Loss of appetite (8% to 22%), Nausea (21% to 58%), Xerostomia (12% to 22%)<br>Neurologic: Asthenia (8% to 19%), Dizziness (11% to 23.9%), Dream disorder (3% to 7%), Headache (25% to 38%), Insomnia (14% to 24%), Somnolence (14% to 26%), Tremor (1.1% to 10.2%)<br>Ophthalmic: Blurred vision (4% to 6%)<br>Psychiatric: Feeling nervous (4% to 21.3%)<br>Reproductive: Abnormal ejaculation (2.2% to 19%), Erectile dysfunction (2.1% to 6%), Orgasm disorder (2% to 5%)<br>Serious<br>Endocrine metabolic: Hyponatremia<br>Gastrointestinal: Gastrointestinal hemorrhage (rare)<br>Hematologic: Bleeding, Abnormal<br>Hepatic: Hepatitis<br>Neurologic: Seizure (0.3%)<br>Psychiatric: Depression, exacerbation (rare), Hypomania, Mania, Suicidal thoughts (rare), Suicide<br>Other: Neuroleptic malignant syndrome, Serotonin syndrome |
| Amitriptyline (Elavil) | Common<br>Endocrine metabolic: Weight gain<br>Gastrointestinal: Constipation, Xerostomia<br>Neurologic: Dizziness, Headache, Somnolence<br>Ophthalmic: Blurred vision<br>Serious<br>Cardiovascular: Cardiac dysrhythmia, Electrocardiogram abnormal, Myocardial infarction, Prolonged QT interval, Sudden cardiac death<br>Hematologic: Agranulocytosis<br>Hepatic: Hepatotoxicity, Jaundice (rare)<br>Neurologic: Neuroleptic malignant syndrome, Seizure<br>Psychiatric: Depression, worsening, Suicidal thoughts, Suicide |
| Bupropion (Wellbutrin) | Common<br>Cardiovascular: Tachycardia (major depressive disorder, 11%)<br>Endocrine metabolic: Weight gain (2% to 9%), Weight loss (major depressive disorder, 14% to 19%)<br>Gastrointestinal: Abdominal pain (2% to 9%), Constipation (5% to 10%), Nausea (13% to 18%), Xerostomia (17% to 26%)<br>Neurologic: Confusion (major depressive disorder, 8%), Dizziness (6% to 11%), Headache (25% to 34%), Insomnia (11% to 20%)<br>Psychiatric: Agitation (2% to 9%)<br>Respiratory: Nasopharyngitis (seasonal affective disorder, 13%), |

TABLE 4-continued

SAMPLE DRUGS AND THEIR SIDE EFFECTS

|  |  |
|---|---|
|  | Pharyngitis (major depressive disorder, 3% to 11%), Upper respiratory infection (seasonal affective disorder, 9%)<br>Serious<br>Cardiovascular: Complete atrioventricular block, Myocardial infarction<br>Gastrointestinal: Colitis, Pancreatitis<br>Hematologic: Pancytopenia<br>Hepatic: Abnormal liver function, Hepatitis, Jaundice, Liver damage<br>Immunologic: Anaphylactoid reaction, Anaphylaxis, Delayed hypersensitivity disorder<br>Musculoskeletal: Rhabdomyolysis<br>Neurologic: Seizure (major depressive disorder, 0.1% to 0.4%)<br>Psychiatric: Delusional disorder, Depression, Worsening, Hallucinations, Hostile behavior (major depressive disorder, 6%), Hypomania, Mania, Precipitation of episode, Paranoid ideation, Psychotic disorder, Activation, Suicidal behavior, Suicidal thoughts<br>Respiratory: Pulmonary embolism<br>Other: Angioedema |
| Nortriptyline (Pamelor) | Common<br>Gastrointestinal: Constipation<br>Serious<br>Cardiovascular: Cardiac dysrhythmia, Heart block, Myocardial infarction, Prolonged QT interval, Sudden cardiac death<br>Endocrine metabolic: Syndrome of inappropriate antidiuretic hormone secretion<br>Gastrointestinal: Paralytic ileus<br>Hematologic: Bone marrow depression<br>Hepatic: Fulminant hepatic failure, Jaundice (rare)<br>Neurologic: Cerebrovascular accident, Myoclonus, Seizure<br>Psychiatric: Depression, worsening, Mania, Psychotic disorder, exacerbation, Suicidal thoughts, Suicide<br>Other: Angioedema |
| Mirtazepine (Remeron) | Common<br>Endocrine metabolic: Increased appetite (17%), Serum triglycerides raised (increases to 500 mg/dL or greater: 6%), Weight gain (body weight increase of 7% or greater: adults 7.5%; pediatrics 49%)<br>Gastrointestinal: Constipation (13%), Xerostomia (25%)<br>Hepatic: ALT/SGPT level raised (2%)<br>Neurologic: Asthenia (8%), Dizziness (7%), Somnolence (54%)<br>Psychiatric: Disturbance in thinking (3%)<br>Serious<br>Hematologic: Agranulocytosis, Neutropenia<br>Hepatic: Cirrhosis of liver (less than 0.1%)<br>Neurologic: Grand mal seizure (less than 0.1%), Status epilepticus<br>Psychiatric: Depression, exacerbation, Suicidal thoughts, Suicide<br>Other: Neuroleptic malignant syndrome, Serotonin syndrome (less than 0.1%) |
| Olanzapine (Zyprexa) | See Olanzapine above |
| Risperidone (Risperdal) | See Resperidone above |
| Antiepileptics |  |
| Divalproex (Depakote) | Common<br>Gastrointestinal: Abdominal pain (9% to 23%), Diarrhea (13% to 23%), Indigestion (8% to 11%), Loss of appetite (4% to 12%), Nausea (26% to 48%), Vomiting (15% to 27%)<br>Musculoskeletal: Backache (Complex partial seizures, greater than 1% to less than 5%; migraine, 8%)<br>Neurologic: Asthenia (6% to 27%), Dizziness (up to 25%), Feeling nervous (up to 11%), Headache (31%), Insomnia (up to 15%), Somnolence (Adult, 7% to 30%; pediatric, greater than 5%), Tremor (1% to 57%)<br>Ophthalmic: Amblyopia, Blurred vision, Diplopia (16%)<br>Other: Infectious disease (12% to 20%), Influenza (12%)<br>Serious<br>Cardiovascular: Palpitations (greater than 1% to less than 5%), Tachycardia (greater than 1% to less than 5%)<br>Endocrine metabolic: Hyperammonemia<br>Gastrointestinal: Pancreatitis (greater than 1% to less than 5%)<br>Hematologic: Myelodysplastic syndrome, Thrombocytopenia, Dose-related (1% to 27%)<br>Hepatic: Liver failure<br>Immunologic: Drug hypersensitivity syndrome (rare)<br>Neurologic: Hyperammonemic encephalopathy<br>Otic: Ototoxicity - deafness (greater than 1% to less than 5%) |
| Ropinirole (Requip) | Common<br>Cardiovascular: Hypotension (2% to 25%), Orthostatic hypotension (Up to 23%) |

TABLE 4-continued

SAMPLE DRUGS AND THEIR SIDE EFFECTS

| | |
|---|---|
| | Gastrointestinal: Abdominal pain (6% to 7%), Constipation (4% to 5%), Nausea (11% to 60%), Vomiting (7% to 12%)<br>Neurologic: Dizziness (Parkinson disease, 6% to 40%; restless legs syndrome, 11%), Dyskinesia (13% to 34%), Headache (6%), Somnolence (Parkinson disease, 7% to 40%; restless leg syndrome, 12%)<br>Other: Fatigue (8% to 11%)<br>Serious<br>Cardiovascular: Sinus node dysfunction, Syncope (Parkinson disease, 1% to 12%; restless leg syndrome, 1%)<br>Neurologic: Sleep attack<br>Psychiatric: Hallucinations (5% to 10%) |
| Pramipexole (Mirapex) | Common<br>Cardiovascular: Orthostatic hypotension (Immediate release, 53%; extended-release, 3%)<br>Gastrointestinal: Constipation (immediate-release, 4% to 14%; extended-release, 7% to 14%), Nausea (immediate-release, 11% to 28%; extended-release, 11% to 22%)<br>Neurologic: Amnesia (4% to 6%), Asthenia (Immediate-release, 10% to 14%; extended-release, 3%), Confusion (4% to 10%), Dizziness (Immediate-release, 3% to 26%; extended-release, 2% to 12%), Dream disorder (Up to 11%), Dyskinesia (Immediate-release, 18% to 47%; extended-release, 17%), Extrapyramidal movements (28%), Headache (Immediate-release, 4% to 16%; extended-release, 7%), Insomnia (Immediate-release, 4% to 27%; extended-release, 4%)<br>Psychiatric: Hallucinations (5% to 17%)<br>Serious<br>Cardiovascular: Heart failure<br>Dermatologic: Malignant melanoma<br>Neurologic: Sleep attack (2% to 6%), Somnolence (Immediate-release, 6% to 33%;; extended-release, 15% to 36%)<br>Psychiatric: Disturbance in thinking, Psychotic disorder<br>Other: Malignant melanoma, Neuroleptic malignant syndrome |
| Methylphenidate (Concerta) | See Methylphenidate above |
| Lisdexamfetamine (Vyvanse) | Common<br>Dermatologic: Rash (pediatrics, 3%)<br>Endocrine metabolic: Decreased body growth, Weight decreased (pediatrics, 9%)<br>Gastrointestinal: Diarrhea (adults, 7%), Loss of appetite (adults, 8% to 27%; pediatrics, 34% to 39%), Nausea (adults, 7%; pediatrics, 6%), Upper abdominal pain (pediatrics, 12%), Vomiting (pediatrics, 9%), Xerostomia (Adults, 26% to 36%; pediatrics, 4% to 5%)<br>Neurologic: Dizziness (pediatrics, 5%), Insomnia (Adults, 20% to 27%; pediatrics, 13% to 23%)<br>Psychiatric: Anxiety (Adults, 5% to 6%), Irritability (pediatrics, 10%)<br>Serious<br>Cardiovascular: Chest pain, Myocardial infarction, Peripheral vascular disease, Raynaud's disease, Sudden cardiac death, Tachycardia, Ventricular hypertrophy<br>Immunologic: Anaphylaxis<br>Neurologic: Cerebrovascular accident, Seizure |
| Amphetamine/Dextro-amphetamine (Adderall) | See Adderall above |
| Dalteparin (Fragmin), Danaparoid (Orgaran) | Common<br>Dermatologic: Hematoma, Injection site (7% to 35%), Injection site pain (4.5% to 12%)<br>Other: Irritation symptom, Local<br>Serious<br>Hematologic: Epidural hematoma, Hematoma, Spinal, Hemorrhage, Major (up to 13.6%), Hemorrhagic cerebral infarction (8%), Intracranial hemorrhage, Subdural hemorrhage, Intrauterine, Thrombocytopenia (Non-cancer indications, less than 1%; patients with cancer, 10.9% to 13.6%)<br>Hepatic: Increased liver function test (up to 4.3%)<br>Immunologic: Anaphylactoid reaction (rare)<br>Neurologic: Paralysis |
| Enoxaparin (Lovenox) | Common<br>Gastrointestinal: Diarrhea (2.2%), Nausea (2.5% to 3%)<br>Hematologic: Anemia (up to 16%), Bleeding, Major (up to 4%), Thrombocytopenia (less than 3%)<br>Hepatic: Increased liver function test (5.9% to 6.1%)<br>Other: Fever (up to 8%)<br>Serious<br>Cardiovascular: Atrial fibrillation (0.7%), Heart failure (0.95%)<br>Dermatologic: Eczematous drug eruption, Skin necrosis |

TABLE 4-continued

SAMPLE DRUGS AND THEIR SIDE EFFECTS

| | |
|---|---|
| Heparin (various) | Hematologic: Hematoma, Hemorrhage (4% to 13%)<br>Neurologic: Intracranial hemorrhage (0.8%), Paraplegia<br>Respiratory: Pneumonia (0.82%)<br>Common<br>Hematologic: Thrombocytopenia (up to 30%)<br>Hepatic: Increased liver aminotransferase level<br>Serious<br>Hematologic: Hemorrhage (5% to 10%), Heparin-induced thrombocytopenia (1% to 10%), Heparin-induced thrombocytopenia with thrombosis (less than 1%)<br>Immunologic: Hypersensitivity reaction<br>Neurologic: Non-traumatic spinal subdural hematoma |
| Tinzaparin (Innohep) | Common<br>Dermatologic: Erythema (16%)<br>Hepatic: Increased liver function test, Asymptomatic (9% to 13%)<br>Neurologic: Pain, Local (16%)<br>Other: Irritation symptom, Local (16%)<br>Serious<br>Hematologic: Bleeding, Major (0.8%), Granulocytopenic disorder (rare), Hematoma, spinal/epidural, Pancytopenia (rare), Thrombocytopenia (1%), Thrombocytopenia (Severe) (0.13%)<br>Immunologic: Anaphylaxis (rare)<br>Neurologic: Paralysis<br>Reproductive: Priapism (rare) |
| Warfarin (Coumadin) | Common<br>Dermatologic: Alopecia<br>Serious<br>Cardiovascular: Cholesterol embolus syndrome, Gangrenous disorder (less than 0.1%)<br>Dermatologic: Tissue necrosis (less than 0.1%)<br>Hematologic: Bleeding, Hemorrhage<br>Immunologic: Hypersensitivity reaction<br>Musculoskeletal: Compartment syndrome<br>Neurologic: Intracranial hemorrhage<br>Ophthalmic: Intraocular hemorrhage |
| Dabigatran (Pradaxa) | Common<br>Gastrointestinal: Esophagitis, Gastritis, Gastroesophageal reflux disease (Atrial fibrillation, 5.5%), Gastrointestinal hemorrhage (DVT and pulmonary embolism, 0.7% to 3.1%; nonvalvular atrial fibrillation, 6.1%), Gastrointestinal ulcer, Indigestion (DVT and pulmonary embolism, 7.5%)<br>Hematologic: Bleeding (DVT and pulmonary embolism prophylaxis, 10.5%; nonvalvular atrial fibrillation, 16.6%)<br>Serious<br>Cardiovascular: Myocardial infarction (DVT and pulmonary embolism, 0.32% to 0.66%; nonvalvular atrial fibrillation, 0.7%)<br>Gastrointestinal: Gastrointestinal hemorrhage, Major (DVT and pulmonary embolism, 0.3% to 0.6%; nonvalvular atrial fibrillation, 1.6%)<br>Hematologic: Bleeding, Major (DVT and pulmonary embolism, 0.3% to 1.4%; nonvalvular atrial fibrillation, 3.3%), Thrombosis<br>Immunologic: Anaphylaxis<br>Neurologic: Epidural hematoma, Intracranial hemorrhage (nonvalvular atrial fibrillation, 0.3%; DVT and pulmonary embolism, 0.1%), Traumatic spinal subdural hematoma<br>Respiratory: Bleeding, Alveolar |
| Rivaroxaban (Xarelto) | Common<br>Hematologic: Bleeding (Hip/knee replacement, 5.8%; DVT/pulmonary embolism, 17.4% to 28.3%)<br>Serious<br>Cardiovascular: Syncope (1.2%)<br>Gastrointestinal: Gastrointestinal hemorrhage (nonvalvular atrial fibrillation, 3.1%)<br>Hematologic: Bleeding, Major (Nonvalvular atrial fibrillation, 5.6%; hip/knee replacement, 0.3%; DVT/pulmonary embolism, 1%), Epidural hematoma, Hematoma, Spinal<br>Immunologic: Anaphylaxis, Hypersensitivity reaction<br>Other: Drug withdrawal, Stroke and non-CNS embolism |
| Apixaban (Eliquis) | Common<br>Dermatologic: Contusion (1.4% to 2.2%)<br>Gastrointestinal: Bleeding gums (Less than 0.1% to 1.4%)<br>Hematologic: Hematoma (DVT, 1.3% to 1.5%)<br>Reproductive: Menorrhagia (1.4%)<br>Respiratory: Epistaxis (DVT and pulmonary embolism, 1.5% to 3.6%; DVT prophylaxis, 0.1% to less than 1%), Hemoptysis (Less than 0.1% to 1.2%)<br>Serious |

TABLE 4-continued

SAMPLE DRUGS AND THEIR SIDE EFFECTS

|  |  |
|---|---|
|  | Gastrointestinal: Gastrointestinal hemorrhage (atrial fibrillation, 0.83%/year; DVT prophylaxis, 0.1% to less than 1%; DVT and pulmonary embolism, 0.1% to less than 1%), Hematochezia (0.1% to less than 1%), Rectal hemorrhage (Less than 0.1% to 1%) Hematologic: Bleeding (atrial fibrillation, 2.08%/year; DVT prophylaxis, 2.88% to 4.83%), Bleeding, Major (0.1% to 2.13%), Hemorrhage (0.1% to 1.4%), Hemorrhage, Operative (DVT prophylaxis, 0.1% to less than 1%) Hepatic: Alkaline phosphatase raised (DVT prophylaxis, 0.1% to less than 1%), Liver function tests abnormal (DVT prophylaxis, 0.1% to less than 1%), Serum bilirubin raised (DVT prophylaxis, 0.1% to less than 1%) Immunologic: Hypersensitivity reaction (atrial fibrillation, less than 1%) Musculoskeletal: Hemorrhage of muscle (Less than 0.1% to less than 1%) Neurologic: Epidural hematoma, Intracranial hemorrhage (atrial fibrillation, 0.33% to 0.34%/year), Non-traumatic spinal subdural hematoma, Traumatic spinal subdural hematoma Ophthalmic: Conjunctival hemorrhage (0.1% to less than 1%), Intraocular hemorrhage (Less than 0.1% to less than 1%), Retinal hemorrhage (0.1% to less than 1%) Renal: Hematuria (DVT, 1.4% to 2.1%; DVT prophylaxis, 0.1% to less than 1%) |
| Edoxaban (Savaysa) | Common Dermatologic: Rash (3.6% to 4.2%) Hematologic: Anemia (Nonvalvular atrial fibrillation, 9.6%; DVT or pulmonary embolism, 1.7%), Bleeding, Clinically Relevant, Nonmajor (Nonvalvular atrial fibrillation, 9.4%; DVT or pulmonary embolism, 7.2%) Hepatic: Liver function tests abnormal (Nonvalvular atrial fibrillation, 4.8%; DVT or pulmonary embolism, 7.8%) Serious Hematologic: Bleeding, Major (Nonvalvular atrial fibrillation, 3.1%; DVT or pulmonary embolism, 1.4%) Neurologic: Hemorrhagic cerebral infarction (Nonvalvular atrial fibrillation, 0.3%), Intracranial hemorrhage (Nonvalvular atrial fibrillation, 0.5%; DVT or pulmonary embolism, 0.1%) Respiratory: Interstitial lung disease (Nonvalvular atrial fibrillation, 0.2%) |
| Aspirin | Serious Gastrointestinal: Gastrointestinal ulcer Hematologic: Bleeding Ophthalmic: Exudative age-related macular degeneration Otic: Tinnitus Respiratory: Bronchospasm Other: Angioedema, Reye's syndrome |
| Ticlopidine | Common Dermatologic: Rash (1% to 11.8%) Gastrointestinal: Abdominal pain, Diarrhea, Indigestion, Loss of appetite, Nausea Hematologic: Hemorrhage, Leukopenia Hepatic: Liver function tests abnormal Neurologic: Dizziness Serious Hematologic: Agranulocytosis, Aplastic anemia (rare), Granulocytopenic disorder, Neutropenia (2.4%), Pancytopenia, Thrombocytopenia, Thrombotic thrombocytopenic purpura (rare) |
| Clopidogrel (Plavix ®) | Common Hematologic: Bleeding, Non-major (3.6% to 5.1%) Serious Cardiovascular: Coronary artery stent thrombosis Dermatologic: Fixed drug eruption Gastrointestinal: Colitis, Gastrointestinal hemorrhage (2%; 2.7% with aspirin) Hematologic: Agranulocytosis (Less than 1%), Aplastic anemia (less then 1%), Bleeding, Major (0.8% to 3.7%), Pancytopenia (Severe), Thrombotic thrombocytopenic purpura Hepatic: Hepatitis, Hepatotoxicity, Liver failure Immunologic: Hypersensitivity reaction Neurologic: Epidural hematoma, Intracranial hemorrhage Ophthalmic: Intraocular hemorrhage (0.05%) Other: Drug withdrawal, Rebound effect |
| Dipyridamole | Common Cardiovascular: Chest pain (IV, up to 30%), Electrocardiogram abnormal (IV, 0.8% to 7.5%) Dermatologic: Flushing (IV, 3.4%), Rash (oral, 2.3%) Gastrointestinal: Abdominal discomfort (oral, 6.1%) |

TABLE 4-continued

SAMPLE DRUGS AND THEIR SIDE EFFECTS

| | |
|---|---|
| | Neurologic: Dizziness (oral, 13.6%; IV, 11.8%), Headache (oral, 2.3%; IV, 12.2% to 20%) |
| | Respiratory: Dyspnea (IV, 2.6% to 25%) |
| | Serious |
| | Cardiovascular: Angina, Cardiac arrest, Myocardial infarction (IV, 0.1%), Myocardial ischemia, Ventricular fibrillation, Ventricular tachycardia (IV, 0.2%) |
| | Hepatic: Liver failure |
| | Immunologic: Hypersensitivity reaction |
| | Neurologic: Cerebrovascular accident, Seizure |
| | Respiratory: Bronchospasm (IV, 0.2%) |
| Benazepril (Lotensin) | Common |
| | Neurologic: Dizziness (3.6%), Headache (6.2%) |
| | Respiratory: Cough (1.2%) |
| | Other: Fatigue (2.4%) |
| | Serious |
| | Dermatologic: Stevens-Johnson syndrome (less than 1%) |
| | Gastrointestinal: Intestinal angioedema |
| | Hematologic: Agranulocytosis, Neutropenia |
| | Hepatic: Hepatic necrosis (rare), Increased liver enzymes (rare), Jaundice (rare) |
| | Immunologic: Anaphylactoid reaction |
| | Renal: Renal impairment |
| | Other: Angioedema, head and neck (0.5%) |
| Captopril (Capoten) | Common |
| | Cardiovascular: Hypotension |
| | Dermatologic: Rash |
| | Endocrine metabolic: Hyperkalemia (11%) |
| | Gastrointestinal: Disorder of taste |
| | Respiratory: Cough (0.5% to 2%) |
| | Serious |
| | Dermatologic: Stevens-Johnson syndrome |
| | Gastrointestinal: Intestinal angioedema |
| | Hematologic: Agranulocytosis (0.1% to 0.2%), Neutropenia (0.1% to 0.2%) |
| | Immunologic: Anaphylactoid reaction |
| | Other: Angioedema (0.1%) |
| Enalapril (Vasotec) | Common |
| | Endocrine metabolic: Hyperkalemia (1% to 3.8%) |
| | Neurologic: Dizziness (4.3% to 7.9%) |
| | Renal: Serum blood urea nitrogen raised (0.2% (hypertension) to 20% (hypertension with renal artery stenosis)), Serum creatinine raised (0.2% (hypertension) to 20% (hypertension with renal artery stenosis)) |
| | Other: Fatigue (3%) |
| | Serious |
| | Cardiovascular: Hypotension (0.9% to 6.7%) |
| | Gastrointestinal: Intestinal angioedema |
| | Hematologic: Agranulocytosis |
| | Hepatic: Hepatotoxicity, Liver failure |
| | Immunologic: Anaphylactoid reaction, during desensitization |
| | Renal: Acute renal failure, Renal impairment |
| | Other: Angioedema (0.1% to 1%) |
| Fosinopril (Monopril) | Common |
| | Cardiovascular: Hypotension (2.4% to 4.4%) |
| | Endocrine metabolic: Hyperkalemia (2.6%) |
| | Gastrointestinal: Nausea and vomiting (1.2% to 2.2%) |
| | Neurologic: Dizziness (1.6% to 11.9%) |
| | Respiratory: Cough (2.2% to 9.7%) |
| | Serious |
| | Gastrointestinal: Intestinal angioedema |
| | Hematologic: Agranulocytosis |
| | Immunologic: Anaphylactoid reaction |
| | Renal: Acute renal failure, Azotemia, Oliguria |
| | Other: Angioedema, Head and Neck |
| Lisinopril (Prinivil, Zestril) | Common |
| | Cardiovascular: Chest pain, Hypotension (up to 11%), Syncope (5% to 7%) |
| | Neurologic: Dizziness (12% to 19%), Headache |
| | Respiratory: Cough |
| | Serious |
| | Cardiovascular: Hypotension (Severe) (9%) |
| | Dermatologic: Stevens-Johnson syndrome (1% or more), Toxic epidermal necrolysis (1% or more) |
| | Endocrine metabolic: Hyperkalemia (2.2% to 6%) |
| | Gastrointestinal: Intestinal angioedema |
| | Immunologic: Anaphylaxis due to hymenoptera venom, Dialysis membrane-induced anaphylactoid reaction |

TABLE 4-continued

SAMPLE DRUGS AND THEIR SIDE EFFECTS

| | |
|---|---|
| | Renal: Acute renal failure, Renal impairment (2.4%) |
| | Other: Angioedema, Head and Neck |
| Moexipril (Univasc) | Common |
| | Gastrointestinal: Diarrhea (3.1%) |
| | Neurologic: Dizziness (4.3%) |
| | Respiratory: Cough (6.1%) |
| | Other: Influenza-like symptoms |
| | Serious |
| | Gastrointestinal: Intestinal angioedema |
| | Hematologic: Agranulocytosis |
| | Immunologic: Anaphylaxis due to hymenoptera venom, Dialysis membrane-induced anaphylactoid reaction |
| | Renal: Abnormal renal function |
| | Other: Angioedema, Head and Neck |
| Perindopril (Aceon) | Common |
| | Endocrine metabolic: Hyperkalemia |
| | Musculoskeletal: Backache (5.8%) |
| | Neurologic: Asthenia, Dizziness (8.2%), Headache |
| | Respiratory: Cough (12%) |
| | Serious |
| | Cardiovascular: Cardiac arrest, Orthostatic hypotension (0.8%) |
| | Gastrointestinal: Intestinal angioedema, Pancreatitis |
| | Hematologic: Agranulocytosis, Bone marrow depression, Neutropenia |
| | Hepatic: Liver failure |
| | Renal: Acute renal failure |
| | Other: Angioedema (0.1% to 0.5%) |
| Quinapril (Accupril) | Common |
| | Cardiovascular: Chest pain (2.4%), Hypotension (2.9%) |
| | Gastrointestinal: Nausea and vomiting (1.4% to 2.4%) |
| | Neurologic: Dizziness (3.9% to 7.7%), Headache (1.7% to 6.9%) |
| | Respiratory: Cough (2% to 4.3%) |
| | Other: Fatigue (2.6%) |
| | Serious |
| | Gastrointestinal: Intestinal angioedema |
| | Hematologic: Agranulocytosis |
| | Immunologic: Anaphylactoid reaction (rare), Anaphylaxis due to hymenoptera venom, Dialysis membrane-induced anaphylactoid reaction |
| | Renal: Serum blood urea nitrogen raised (2% to 8%), Serum creatinine raised (2% to 11%) |
| | Other: Angioedema |
| Ramipril (Altace) | Common |
| | Cardiovascular: Hypotension (11%) |
| | Neurologic: Asthenia, Dizziness (2.2% to 4%), Headache (5.4%) |
| | Respiratory: Cough (8% to 12%) |
| | Other: Fatigue |
| | Serious |
| | Dermatologic: Stevens-Johnson syndrome |
| | Gastrointestinal: Intestinal angioedema, Pancreatitis |
| | Hepatic: Hepatic necrosis, Hepatotoxicity |
| | Immunologic: Anaphylactoid reaction |
| | Other: Angioedema, Head and Neck |
| Trandolapril (Mavik) | Common |
| | Cardiovascular: Hypotension (0.6% to 11%), Syncope (5.9%) |
| | Endocrine metabolic: Hyperkalemia (0.3% to 5.3%) |
| | Gastrointestinal: Indigestion (0.3% to 6.4%) |
| | Neurologic: Dizziness (1.3% to 23%) |
| | Renal: Serum blood urea nitrogen raised (9%) |
| | Respiratory: Cough (1.9% to 35%) |
| | Serious |
| | Cardiovascular: Cardiogenic shock (3.8%), Intermittent claudication (3.8%) |
| | Gastrointestinal: Intestinal angioedema |
| | Hematologic: Agranulocytosis |
| | Immunologic: Anaphylaxis due to hymenoptera venom, Dialysis membrane-induced anaphylactoid reaction |
| | Other: Angioedema |
| Candesartan (Atacand) | Common |
| | Cardiovascular: Hypotension (18.8%) |
| | Musculoskeletal: Backache (3%.) |
| | Neurologic: Dizziness (less than 5%) |
| | Respiratory: Pharyngitis (2%), Rhinitis (2%), Upper respiratory infection (6%) |
| Eprosartan (Teveten) | Common |
| | Gastrointestinal: Abdominal pain |
| | Musculoskeletal: Myalgia (1.9%) |
| | Neurologic: Dizziness (3.8%) |

TABLE 4-continued

SAMPLE DRUGS AND THEIR SIDE EFFECTS

| | |
|---|---|
| | Respiratory: Upper respiratory infection |
| | Other: Fatigue (1.4%) |
| | Serious |
| | Dermatologic: Edema of face (rare) |
| | Hematologic: Neutropenia (1.3%) |
| Irbesartan (Avapro) | Common |
| | Gastrointestinal: Diarrhea, Heartburn |
| | Neurologic: Headache |
| | Respiratory: Upper respiratory infection |
| | Other: Fatigue |
| | Serious |
| | Hematologic: Thrombocytopenia |
| | Hepatic: Cholestasis, Hepatitis |
| | Musculoskeletal: Rhabdomyolysis |
| | Renal: Renal failure |
| | Other: Angioedema, face, lips, throat |
| Losartan (Cozaar) | Common |
| | Cardiovascular: Chest pain (12%), Hypotension (7%) |
| | Endocrine metabolic: Hyperkalemia (7%), Hypoglycemia (14%) |
| | Gastrointestinal: Diarrhea (15%) |
| | Hematologic: Anemia (14%) |
| | Neurologic: Asthenia, Dizziness (3%) |
| | Respiratory: Cough (10%) |
| | Other: Fatigue |
| | Serious |
| | Hepatic: Hepatotoxicity |
| | Musculoskeletal: Rhabdomyolysis |
| | Renal: Acute renal failure |
| | Other: Angioedema |
| Telmisartan (Micardis)) | Common |
| | Respiratory: Cough (1.6% to 15.6%), Upper respiratory infection (7%) |
| | Serious |
| | Musculoskeletal: Rhabdomyolysis (rare) |
| Valsartan (Diovan) | Common |
| | Cardiovascular: Hypotension (5.5% to 6.9%) |
| | Neurologic: Dizziness (2% to 17%), Headache (greater than 1%) |
| | Renal: Serum blood urea nitrogen raised (heart failure, 16.6%), Serum creatinine raised (hypertension, 0.8%; heart failure, 3.9%; post-myocardial infarction, 4.2%) |
| | Respiratory: Cough |
| | Serious |
| | Renal: Acute renal failure |
| | Other: Angioedema, Face, lips, throat |
| Sacubitril/valsartan (Entresto) | Common |
| | Cardiovascular: Hypotension (18%) |
| | Endocrine metabolic: Hyperkalemia (12%) |
| | Neurologic: Dizziness (6%) |
| | Serious |
| | Renal: Renal failure (5%) |
| | Other: Angioedema (0.5%) |
| Acebutolol (Sectral) | Common |
| | Neurologic: Dizziness (6%), Headache (6%) |
| | Other: Fatigue (11%) |
| | Serious |
| | Cardiovascular: Angina (2%), Bradyarrhythmia (2%), Heart failure (2%) |
| | Hepatic: Hepatotoxicity (rare) |
| | Immunologic: Anaphylaxis, Systemic lupus erythematosus (rare.) |
| Atenolol (Tenormin) | Common |
| | Cardiovascular: Bradyarrhythmia (3% to 18%), Cold extremities (12%), Hypotension (4% to 25%) |
| | Neurologic: Dizziness (13%) |
| | Psychiatric: Depression (up to 12%) |
| | Other: Fatigue (up to 26%) |
| | Serious |
| | Cardiovascular: Heart failure, Myocardial infarction, Ventricular arrhythmia |
| | Endocrine metabolic: Thyrotoxicosis |
| | Immunologic: Anaphylaxis, Systemic lupus erythematosus |
| | Respiratory: Pulmonary embolism (1.2%) |
| | Other: Withdrawal sign or sy |
| Betaxolol (Kerlone) | Common |
| | Cardiovascular: Bradyarrhythmia (5.8% to 8.1%) |
| | Gastrointestinal: Indigestion (3.9% to 4.7%), Nausea (1.6% to 5.8%) |
| | Musculoskeletal: Arthralgia (3.1% to 5.2%), Chest pain (2.4% to 7.1%) |

TABLE 4-continued

SAMPLE DRUGS AND THEIR SIDE EFFECTS

| | |
|---|---|
| | Ophthalmic: Burning sensation in eye (30%, ophthalmic) |
| | Other: Fatigue (2.9% to 9.7%) |
| | Serious |
| | Cardiovascular: Atrioventricular block, Myocardial infarction |
| Bisoprolol/hydrochlorothiazide (Ziac) | Common |
| | Gastrointestinal: Diarrhea (4.3%) |
| | Neurologic: Dizziness (5.1%), Headache (4.5%) |
| | Other: Fatigue (4.6%) |
| | Serious |
| | Cardiovascular: Heart failure |
| | Ophthalmic: Angle-closure glaucoma, acute, Myopia, Acute transient |
| | Respiratory: Bronchospasm |
| Bisoprolol (Zebeta) | Common |
| | Gastrointestinal: Diarrhea (2.6% to 3.5%) |
| | Neurologic: Headache (8.8% to 10.9%) |
| | Respiratory: Rhinitis (2.9% to 4%), Upper respiratory infection (4.8% to 5%.) |
| | Other: Fatigue (6.6% to 8.2%) |
| Carteolol (Cartrol) | Common |
| | Cardiovascular: Angina |
| | Neurologic: Asthenia (7%.), Dizziness (4% to 15%.), Headache (4% to 17%.), Insomnia (2% to 12%.) |
| | Ophthalmic: Blurred vision, Burning sensation in eye (25%), Conjunctival edema (25%), Conjunctival hyperemia (25%), Epiphora (25%), Eye irritation (25%) |
| | Serious |
| | Cardiovascular: Cardiac dysrhythmia, Heart failure |
| | Respiratory: Bronchospasm |
| Metoprolol (Lopressor, Toprol XL) | Common |
| | Cardiovascular: Bradyarrhythmia (3%), Cold extremities (1%), Heart failure (1%), Hypotension (1%) |
| | Dermatologic: Pruritus (5%), Rash (5%) |
| | Gastrointestinal: Constipation (1%), Diarrhea (5%), Indigestion (1%), Nausea (1%) |
| | Neurologic: Dizziness (10%), Fatigue (10%), Headache |
| | Psychiatric: Depression (5%) |
| | Respiratory: Dyspnea (3%), Wheezing (1%) |
| | Serious |
| | Respiratory: Bronchospasm (1%) |
| Nadolol (Corgard) | Common |
| | Cardiovascular: Bradyarrhythmia (2%) |
| | Neurologic: Dizziness (2%) |
| | Other: Fatigue (2%) |
| | Serious |
| | Cardiovascular: Atrioventricular block, Cardiac dysrhythmia (1%), Heart failure (1%) |
| Propranolol (Inderal) | Common |
| | Gastrointestinal: Diarrhea, Vomiting |
| | Neurologic: Dizziness (Hypertension, 4% to 7%), Sleep disorder |
| | Other: Fatigue (5% to 7%) |
| | Serious |
| | Cardiovascular: Bradyarrhythmia, Cardiogenic shock, Congestive heart failure, Heart block, Heart failure, Hypotension, Prolonged PR interval, Shortened QT interval |
| | Dermatologic: Erythroderma, Stevens-Johnson syndrome, Toxic epidermal necrolysis |
| | Endocrine metabolic: Hypoglycemia |
| | Immunologic: Anaphylaxis |
| | Neurologic: Cerebrovascular accident |
| | Respiratory: Bronchospasm |
| | Other: Withdrawal sign or symptom |
| Sotalol (Betapace) | Common |
| | Cardiovascular: Chest pain (Adult, 16%; pediatric, 4%), Lightheadedness (12%) |
| | Dermatologic: Rash (5%) |
| | Neurologic: Disturbance of consciousness (4%), Dizziness (13.1% to 20%), Headache (3.3% to 11.5%) |
| | Respiratory: Dyspnea (9.2% to 21%) |
| | Other: Fatigue (18.9% to 20%) |
| | Serious |
| | Cardiovascular: Atrioventricular block, Bradyarrhythmia (Adult, 12.3% to 16%; pediatric, 4%), Cardiac dysrhythmia (5%), Congestive heart failure (1.2% to 3.3%), Heart failure (5%), Prolonged QT interval, Torsades de pointes (0.5% to 4%) |
| | Neurologic: Cerebrovascular accident (1%) |

TABLE 4-continued

SAMPLE DRUGS AND THEIR SIDE EFFECTS

| | |
|---|---|
| Timolol (Blocadren) | Common |
| | Cardiovascular: Angina, Bradyarrhythmia (5% to 9.1%, oral), |
| | Heart failure (8%, oral), Hypotension |
| | Dermatologic: Pruritus, Rash, Urticaria |
| | Gastrointestinal: Abdominal pain, Diarrhea, Indigestion, Nausea, |
| | Vomiting |
| | Musculoskeletal: Cramp |
| | Neurologic: Confusion (13%), Dizziness (2.3% to 6%, oral), |
| | Headache (1.7%, oral; 1% to 5%, ophthalmic) |
| | Ophthalmic: Blurred vision (Ophthalmic, 15% to 33%), Burning |
| | sensation in eye (Ophthalmic, 12.5% to 20%), Dry eyes |
| | Psychiatric: Depression (9.2%, ophthalmic), Hallucinations (11%), |
| | Psychotic disorder (3%) |
| | Respiratory: Cough, Dyspnea (1.7%, oral) |
| | Other: Fatigue (3.4% to 5%, oral), Infectious disease |
| | Serious |
| | Cardiovascular: Cardiac dysrhythmia (1%), Myocardial infarction |
| | (rare) |
| | Respiratory: Bronchospasm (0.6%, oral) |
| carvedilol, Common brand | Common |
| names - Coreg* | Cardiovascular: Bradyarrhythmia (3% to 10%), Hypotension (1.8% |
| | to 20.2%), Peripheral edema (1% to 7%) |
| | Endocrine metabolic: Abnormal weight gain (10% to 12%), |
| | Hyperglycemia (5% to 12%) |
| | Gastrointestinal: Diarrhea (2% to 12%) |
| | Neurologic: Dizziness (6% to 33%) |
| | Reproductive: Erectile dysfunction (13.5%) |
| | Other: Fatigue (24%) |
| | Serious |
| | Cardiovascular: Atrioventricular block (greater than 1% to 3%) |
| | Dermatologic: Erythema multiforme, Stevens-Johnson syndrome, |
| | Toxic epidermal necrolysis |
| | Hematologic: Aplastic anemia |
| | Ophthalmic: Intraoperative floppy iris syndrome |
| | Respiratory: Asthma with status asthmaticus (rare) |
| labetolol hydrochloride, | Common |
| Common brand names - | Cardiovascular: Orthostatic hypotension (1%, oral; 58%, IV) |
| Normodyne*, Trandate* | Dermatologic: Has tingling sensation (7%.) |
| | Gastrointestinal: Nausea (14%) |
| | Neurologic: Dizziness (9% to 20%) |
| | Respiratory: Nasal congestion (3%) |
| | Other: Fatigue (11%) |
| | Serious |
| | Cardiovascular: Heart failure |
| | Endocrine metabolic: Hyperkalemia |
| | Hepatic: Hepatotoxicity |
| | Respiratory: Bronchospasm |
| Amlodipine (Norvasc, Lotrel) | Common |
| | Cardiovascular: Flushing (0.7% to 2.6%), Palpitations (Up to |
| | 4.5%), Peripheral edema (Up to 10.8%) |
| | Gastrointestinal: Abdominal pain (1.6%), Nausea (2.9%.) |
| | Neurologic: Dizziness (Up to 3.4%), Headache (7.3%), |
| | Somnolence (1.4%) |
| | Other: Fatigue (4.5%) |
| | Serious |
| | Cardiovascular: Acute myocardial infarction, Angina |
| | Other: Angioedema |
| Bepridil (Vascor) | Common |
| | Diarrhea |
| | Dizzy |
| | Feel Like Throwing Up |
| | Infrequent side effects of Vascor: |
| | Abnormal Heart Rhythm |
| | Chronic Heart Failure |
| | Fluid in the Lungs |
| | Prolonged Q-T Interval on EKG |
| | Slow Heartbeat |
| | Very Rapid Heartbeat - Torsades de Pointes |
| | Head Pain |
| | Incomplete or Infrequent Bowel Movements |
| | Low Energy |
| | Rare side effects of Vascor: |
| | Deficiency of Granulocytes a Type of White Blood Cell |
| | Fluid Retention in the Legs, Feet, Arms or Hands |
| | Inflammation of Skin caused by an Allergy |
| | Rash |
| | Reaction due to an Allergy |
| | Low Blood Pressure |

TABLE 4-continued

SAMPLE DRUGS AND THEIR SIDE EFFECTS

| | |
|---|---|
| Diltiazem (Cardizem, Tiazac) | Common |
| | Cardiovascular: Bradyarrhythmia (1.7% to 3.6%), Peripheral edema (4.6% to 8%) |
| | Neurologic: Dizziness (3.5% to 6.4%), Headache (4.6%) |
| | Respiratory: Cough (2%) |
| | Other: Fatigue (4.8%) |
| | Serious |
| | Cardiovascular: Congestive heart failure (less than 2%), Heart block, Myocardial infarction |
| | Hepatic: Hepatotoxicity |
| Felodipine (Plendil) | Common |
| | Cardiovascular: Peripheral edema (2% to 17.4%) |
| | Dermatologic: Flushing (3.9% to 6.9%) |
| | Gastrointestinal: Indigestion (0.5% to 3.9%) |
| | Neurologic: Headache (10.6% to 14.7%) |
| | Respiratory: Upper respiratory infection (0.7% to 3.9%) |
| | Serious |
| | Cardiovascular: Angina, Hypotension (less than 0.5%), Myocardial infarction, Tachycardia |
| | Neurologic: Cerebrovascular accident |
| Nifedipine (Adalat, Procardia) | Common |
| | Cardiovascular: Hypotension (up to 5%), Palpitations (up to 7%), Peripheral edema (7% to 29%) |
| | Dermatologic: Flushing (4% to 25%) |
| | Gastrointestinal: Nausea (up to 10%) |
| | Neurologic: Dizziness (4% to 10%), Headache (19% to 23%) |
| | Psychiatric: Feeling nervous |
| | Respiratory: Cough, Dyspnea |
| | Serious |
| | Cardiovascular: Myocardial infarction (up to 4%), Ventricular arrhythmia (less than 0.5%) |
| | Gastrointestinal: Gastrointestinal obstruction, Gastrointestinal ulcer |
| | Hematologic: Aplastic anemia |
| Nimodipine (Nimotop) | Common |
| | Cardiovascular: Hypotension (up to 8.1%) |
| | Gastrointestinal: Diarrhea (up to 4.2%), Nausea (0.6% to 1.4%) |
| | Neurologic: Headache (up to 4.1%) |
| | Serious |
| | Cardiovascular: Congestive heart failure (less than 1%) |
| | Gastrointestinal: Gastrointestinal hemorrhage (less than 1%) |
| | Hematologic: Bleeding, Disseminated intravascular coagulation (less than 1%), Hematoma (less than 1%) |
| Nisoldipine (Sular) | Common |
| | Cardiovascular: Palpitations (3%), Peripheral edema (22%), Vasodilatation (4%) |
| | Dermatologic: Flushing |
| | Neurologic: Dizziness (5%), Headache (22%) |
| | Respiratory: Pharyngitis (5%), Sinusitis |
| | Serious |
| | Cardiovascular: Myocardial infarction |
| Verapamil (Calan, Isoptin, Verelan) | Common |
| | Cardiovascular: Edema (up to 3.7%), Hypotension (1.5% to 3%) |
| | Gastrointestinal: Constipation (7.3% to 13%) |
| | Neurologic: Dizziness (3% to 5.9%), Headache (2.2% to 12.1%) |
| | Respiratory: Pharyngitis (3%), Sinusitis (3%) |
| | Other: Influenza-like symptoms (3.7%) |
| | Serious |
| | Cardiovascular: Atrioventricular block, Myocardial infarction |
| | Respiratory: Pulmonary edema |
| Digoxin | Common |
| | Gastrointestinal: Nausea and vomiting |
| | Neurologic: Dizziness, Headache |
| | Psychiatric: Mental disorder |
| | Serious |
| | Cardiovascular: Cardiac dysrhythmia, Ischemia, Sinoatrial block, Sinus bradycardia, Vasoconstriction |
| | Hematologic: Thrombocytopenia |
| Digitoxin | Common |
| | Enlarged BreastsLCommon side effects of digitoxin: |
| | Enlarged Breasts |
| | Infrequent side effects of digitoxin: |
| | Sinus Bradycardia |
| | Rare side effects of digitoxin: |
| | Abnormal Heart Electrical Signals |
| | Atrioventricular Heart Block |
| | Decreased Blood Platelets |
| | Delirium |
| | Diarrhea |

TABLE 4-continued

SAMPLE DRUGS AND THEIR SIDE EFFECTS

|  |  |
|---|---|
|  | Fast Heartbeat |
|  | Gangrene of Intestine caused by Blood Supply ProblemSevere |
|  | Heart Block |
|  | Inflammation of Skin caused by an Allergy |
|  | Loss of Appetite |
|  | Rapid Ventricular Heartbeat |
|  | Rash |
|  | Reaction due to an Allergy |
|  | Throwing Up |
|  | Ventricular Fibrillation |
|  | Ventricular Premature Beats |
|  | Visual Halos Around Lights |
|  | Anxious |
|  | Blurred Vision |
|  | Confused |
|  | Depression E194 |
|  | Discolored Spots and Small Elevations of the SkinLess |
|  | DizzyLess |
|  | Feel Like Throwing Up |
|  | Feeling Weak |
|  | Hallucination |
|  | Head Pain |
| Lanoxin | See Digoxin above |
| Amiloride (Midamor) | Common |
|  | Dermatologic: Rash (1% or less) |
|  | Gastrointestinal: Diarrhea (3% to 8%), Loss of appetite (3% to 8%), |
|  | Nausea (3% to 8%), Vomiting (3% to 8%) |
|  | Musculoskeletal: Asthenia (greater than 1% to less than 3%), |
|  | Cramp (greater than 1% to less than 3%) |
|  | Neurologic: Dizziness (greater than 1% to less than 3%), Headache |
|  | (3% to 8%) |
|  | Respiratory: Cough (greater than 1% to less than 3%), Dyspnea |
|  | (greater than 1% to less than 3%) |
|  | Serious |
|  | Cardiovascular: Cardiac dysrhythmia (1% or less), Palpitations (1% |
|  | or less) |
|  | Endocrine metabolic: Hyperkalemia (10%) |
|  | Hematologic: Aplastic anemia, Neutropenia |
|  | Neurologic: Encephalopathy (greater than 1% to less than 3%) |
|  | Ophthalmic: Raised intraocular pressure (1% or less) |
| Bumetanide (Bumex) | Common |
|  | Cardiovascular: Hypotension (0.8%) |
|  | Endocrine metabolic: Hyperuricemia (18.4%), Hypochloremia |
|  | (14.9%), Hypokalemia (14.7%) |
|  | Gastrointestinal: Nausea (0.6%) |
|  | Musculoskeletal: Cramp (1.1%) |
|  | Neurologic: Dizziness (1.1%), Headache (0.6%) |
|  | Renal: Azotemia (10.6%) |
|  | Serious |
|  | Dermatologic: Stevens-Johnson syndrome |
|  | Hematologic: Thrombocytopenia (0.2%) |
|  | Neurologic: Encephalopathy (0.6%) |
| Chlorothiazide (Diuril) | Common |
|  | Dermatologic: Photosensitivity |
|  | Endocrine metabolic: Hyperglycemia, Hyperuricemia |
|  | Gastrointestinal: Diarrhea, Loss of appetite, Nausea, Vomiting |
|  | Neurologic: Dizziness |
|  | Serious |
|  | Dermatologic: Cutaneous lupus erythematosus, Stevens-Johnson |
|  | syndrome, Toxic epidermal necrolysis |
|  | Endocrine metabolic: Electrolytes abnormal |
|  | Gastrointestinal: Pancreatitis |
|  | Hematologic: Agranulocytosis, Aplastic anemia, Hemolytic anemia |
|  | Hepatic: Hepatotoxicity, Jaundice |
|  | Immunologic: Anaphylaxis, Systemic lupus erythematosus |
|  | Neurologic: Coma |
|  | Renal: Renal failure |
|  | Respiratory: Pulmonary edema, Noncardiogenic |
| Chlorthalidone (Hygroton) | Common |
|  | Endocrine metabolic: Hyperuricemia |
|  | Serious |
|  | Cardiovascular: Cardiac dysrhythmia |
|  | Dermatologic: Toxic epidermal necrolysis |
|  | Gastrointestinal: Pancreatitis (rare) |
|  | Hepatic: Cholestatic jaundice syndrome |
|  | Respiratory: Pulmonary edema (rare) |

TABLE 4-continued

SAMPLE DRUGS AND THEIR SIDE EFFECTS

| | |
|---|---|
| Furosemide (Lasix) | Common |
| | Endocrine metabolic: Hyperuricemia (40%), Hypomagnesemia |
| | Gastrointestinal: Loss of appetite |
| | Renal: Spasm of bladder |
| | Serious |
| | Cardiovascular: Orthostatic hypotension |
| | Dermatologic: Drug hypersensitivity syndrome, Erythema multiforme, Erythroderma, Stevens-Johnson syndrome, Toxic epidermal necrolysis due to drug |
| | Gastrointestinal: Pancreatitis |
| | Hematologic: Agranulocytosis, Aplastic anemia, Thrombocytopenia |
| | Immunologic: Anaphylactoid reaction, Anaphylaxis |
| Hydro-chlorothiazide (Esidrix, Hydrodiuril) | Common |
| | Cardiovascular: Hypotension |
| | Dermatologic: Phototoxicity |
| | Neurologic: Vertigo |
| | Serious |
| | Cardiovascular: Cardiac dysrhythmia |
| | Dermatologic: Stevens-Johnson syndrome, Toxic epidermal necrolysis |
| | Endocrine metabolic: Dilutional hyponatremia, Hypercalcemia, Hyperglycemia, Hypokalemia, Hypomagnesemia, Hyponatremia, Hypophosphatemia |
| | Gastrointestinal: Cholecystitis, Pancreatitis |
| | Hepatic: Cholestatic jaundice syndrome |
| | Ophthalmic: Angle-closure glaucoma, acute, Myopia, Acute transient |
| | Renal: Renal failure, Renal impairment |
| Indapamide (Lozol) | Common |
| | Endocrine metabolic: Hypokalemia (3% to 7%) |
| | Musculoskeletal: Cramp |
| | Neurologic: Asthenia, Dizziness (Greater than or equal to 5%), Headache (Greater than or equal to 5%), Lethargy, Numbness |
| | Other: Fatigue, Malaise |
| | Serious |
| | Dermatologic: Stevens-Johnson syndrome, Toxic epidermal necrolysis |
| | Hematologic: Agranulocytosis, Aplastic anemia |
| | Hepatic: Hepatitis |
| | Immunologic: Anaphylaxis |
| Spironolactone (Aldactone) | Common |
| | Endocrine metabolic: Gynecomastia |
| | Gastrointestinal: Diarrhea, Nausea and vomiting |
| | Neurologic: Somnolence |
| | Reproductive: Disorder of menstruation, Erectile dysfunction |
| | Serious |
| | Dermatologic: Stevens-Johnson syndrome, Toxic epidermal necrolysis |
| | Endocrine metabolic: Breast cancer, Disorder of electrolytes, Hyperkalemia, Metabolic acidosis |
| | Gastrointestinal: Gastric hemorrhage, Gastritis |
| | Hematologic: Agranulocytosis |
| | Immunologic: Drug hypersensitivity syndrome, Systemic lupus erythematosus |
| | Other: Breast cancer |
| Isosorbide dinitrate (Isordil) | Common |
| | Cardiovascular: Hypotension, Lightheadedness |
| | Neurologic: Headache |
| | Serious |
| | Cardiovascular: Syncope |
| | Hematologic: Methemoglobinemia |
| Nesiritide (Natrecor) | Common |
| | Cardiovascular: Hypotension (4% to 17%) |
| | Gastrointestinal: Nausea (3%) |
| | Neurologic: Dizziness (2%), Headache (7%) |
| | Renal: Serum creatinine raised (17% to 31.4%) |
| | Serious |
| | Dermatologic: Injection site extravasation |
| | Immunologic: Hypersensitivity reaction |
| | Other: Death, Increased risk |
| Hydralazine (Apresoline) | Common |
| | Cardiovascular: Angina, Edema, Palpitations, Tachycardia |
| | Gastrointestinal: Diarrhea, Loss of appetite, Nausea, Vomiting |
| | Neurologic: Headache |
| | Serious |
| | Hematologic: Agranulocytosis, Leukopenia |
| | Hepatic: Hepatotoxicity |

TABLE 4-continued

SAMPLE DRUGS AND THEIR SIDE EFFECTS

| | |
|---|---|
| Nitrates (Nitroglycerin) | Immunologic: Lupus pneumonia (Acute), Systemic lupus erythematosus<br>Common<br>Cardiovascular: Hypotension (4%)<br>Dermatologic: Flushing<br>Neurologic: Dizziness (5%), Headache (63% to 64%), Lightheadedness (6%)<br>Serious<br>Dermatologic: Anaphylactoid reaction<br>Hematologic: Methemoglobinemia<br>Neurologic: Raised intracranial pressure |
| Minoxidil | Common<br>Cardiovascular: Hypotension<br>Dermatologic: Hirsutism, Hypertrichosis<br>Endocrine metabolic: Body fluid retention (7%), Hypernatremia<br>Serious<br>Cardiovascular: Angina, Cardiac tamponade, Electrocardiogram abnormal (60%), Pericardial effusion (3%), Pericarditis, Tachyarrhythmia<br>Dermatologic: Stevens-Johnson syndrome<br>Hematologic: Leukopenia, Thrombocytopenia |

Table 5 is included by reference as the drugs that are listed as in development in the following databases: Cortellis™ Competitive Intelligence by Thomson Reuters; Adis R&D; and Pharmaprojects by Citeline. The drugs in the development pipeline can utilize the Invention to capture required clinical trial information and control drug dispensing for regulatory drug approval as well as to control drug dispensing after regulatory approval. The drugs are encompassed in the embodiment of the invention by reference. The listing for each drug includes by definition each drug's respective indication(s), strength, dosage form, route of administration, side effect profile, drug interactions, etc.

Table 6 is included by reference as the mechanisms of action for marketed drugs, drugs in developed, and efficacious drugs whose development was stopped due to a side effect(s) that can be addressed by the embodiment and thereby made approvable. The listed drugs in the following databases are encompassed in the embodiment of the invention by reference: Cortellis™ Competitive Intelligence by Thomson Reuters; Adis R&D; and Pharmaprojects by Citeline. The listing for each includes by definition each respective drug's respective indication(s), strength, dosage form, route of administration, side effect profile, drug interactions, etc.

Table 7 is included by reference as the oral drugs listed in the following databases that (i) were in development but were discontinued due to dose related side effects whose safety concerns can be addressed by the Invention or (ii) drugs that were withdrawn from the market after approval due to dose related side effects whose safety concerns can be addressed by the Invention: Cortellis™ Competitive Intelligence by Thomson Reuters; Adis R&D; and Pharmaprojects by Citeline. These drugs are encompassed in the embodiment of the invention by reference. The listing for each drug includes by definition each drug's respective indication(s), strength, dosage form, route of administration, side effect profile, drug interactions, etc.

Table 8 is a sample list of diseases encompassed in the embodiment of the invention by reference. The listing for each encompasses drugs used to treat the disease and for each includes by definition each drug's respective indication(s), strength, dosage form, route of administration, side effect profile, drug interactions, etc.

TABLE 8

Diseases

Abdominal Aortic Aneurysm - see Aortic Aneurysm
ACE (Adverse Childhood Experiences)
Acinetobacter Infection
Acquired Immune Deficiency Syndrome (AIDS) - see HIV/AIDS
Acquired Immunodeficiency Syndrome (AIDS) - see HIV/AIDS
Adenovirus Infection
Adenovirus Vaccination
ADHD [Attention Deficit/Hyperactivity Disorder]
Adult Vaccinations
Adverse Childhood Experiences (ACE)
African Trypanosomiasis - see Sleeping Sickness
Agricultural Safety - see Farm Worker Injuries
AHF (Alkhurma hemorrhagic fever)
AIDS (Acquired Immune Deficiency Syndrome)
AIDS (Acquired Immunodeficiency Syndrome)
Alkhurma hemorrhagic fever (AHF)
ALS [Amyotrophic Lateral Sclerosis]
Alzheimer's Disease
Amebiasis, Intestinal [Entamoeba histolytica infection]
American Indian and Alaska Native Vaccination
American Trypanosomiasis - see Chagas Disease

TABLE 8-continued

Diseases

Amphibians and Fish, Infections from - see Fish and Amphibians, Infections from
Amyotrophic Lateral Sclerosis - see ALS
Anaplasmosis, Human
Ancylostoma duodenale Infection, Necator americanus Infection - see Human Hookworm
Anemia
*Angiostrongylus* Infection
Animal-Related Diseases
Anisakiasis - see *Anisakis* Infection
*Anisakis* Infection [Anisakiasis]
Anthrax [*Bacillus anthracis* Infection]
Anthrax Emergency Vaccination
Antibiotic and Antimicrobial Resistance
Antibiotic Use, Appropriate
Aortic Aneurysm
Aortic Dissection - see Aortic Aneurysm
Arenavirus Infection
Arthritis
Ascariasis - see Ascaris Infection
Ascaris Infection [Ascariasis]
ASDs (Autism and Genetics)
Aseptic Meningitis - see Viral Meningitis
Aspergillosis - see *Aspergillus* Infection
*Aspergillus* Infection [Aspergillosis]
Asthma
Attention Deficit/Hyperactivity Disorder - see ADHD
Autism
Autism and Genetics (ASDs) [autism spectrum disorders]
autism spectrum disorders - see Autism and Genetics
Avian Influenza
B virus Infection [Herpes B virus]
*B. cepacia* infection (*Burkholderia cepacia* Infection)
*Babesia* Infection - see Babesiosis
Babesiosis [*Babesia* Infection]
*Bacillus anthracis* - see Anthrax
*Bacillus anthracis* Infection - see Anthrax
Back Belts - see Ergonomic and Musculoskeletal Disorders
Bacterial Meningitis
Bacterial Vaginosis (BV)
*Balamuthia mandrillaris* Infection - see *Balamuthia* Infection
*Balamuthia* Infection [*Balamuthia mandrillaris* Infection]
Balantidiasis - see *Balantidium* Infection
*Balantidium* Infection [Balantidiasis]
*Bartonella bacilliformis* Infection - see Carrion's disease
*Bartonella quintana* Infection - see Trench fever
*Baylisascaris* Infection - see Raccoon Roundworm Infection
BCG (Tuberculosis Vaccine)
Bilharzia - see Schistosomiasis
Bioterrorism Agents/Diseases
Bird Flu - see Avian Influenza
Birth Defects
Black Lung [Coal Workers' Pneumoconioses]
Blast Injuries
*Blastocystis hominis* Infection - see *Blastocystis* Infection
*Blastocystis* Infection [*Blastocystis hominis* Infection]
Blastomycosis [*Blastomyces dermatitidis* Infection]
Bleeding Disorders
blood clot
Blood Disorders
Body Lice [*Pediculus humanus corporis*]
Bone Health
*Borrelia burgdorferi* Infection - see Lyme Disease
Botulism [*Clostridium botulinim* Infection]
Bovine Spongiform Encephalopathy (BSE)
Brainerd Diarrhea
Breast and Ovarian Cancer and Family Health History
Breast Cancer
Breastfeeding
Bronchiolitis - see Respiratory Syncytial Virus Infection
Bronchitis
*Brucella* Infection [Brucellosis]
Brucellosis - see *Brucella* Infection
BSE (Bovine Spongiform Encephalopathy)
BSE (Mad Cow Disease)
*Burkholderia cepacia* Infection (*B. cepacia* infection)
*Burkholderia mallei* - see Glanders
*Burkholderia pseudomallei* Infection - see Melioidosis
BV (Bacterial Vaginosis)
*C. diff.* Infection [*Clostridium difficile* Infection]

TABLE 8-continued

Diseases

*C. gattii* cryptococcosis
*C. neoformans* cryptococcosis
*Campylobacter* Infection [Campylobacteriosis]
Campylobacteriosis - see *Campylobacter* Infection
Cancer
Cancer and Flu
Cancer Health Disparities - see Health Disparities in Cancer
*Candida* Infection [Candidiasis]
Candidiasis - see *Candida* Infection
Canine Flu
*Capillaria* Infection [Capillariasis]
Capillariasis - see *Capillaria* Infection
Carbapenem resistant *Klebsiella pneumonia* (CRKP) - see *Klebsiella pneumoniae*
Carbapenem-resistant Enterobacteriaceae (CRE)
Cardiovascular Health - see Heart Disease
Carpal Tunnel Syndrome - see Ergonomic and Musculoskeletal Disorders
Carrion's disease [*Bartonella bacilliformis* Infection]
Cat Flea Tapeworm - see Tapeworm, Dog and Cat Flea
Cats, Infections from
CCHF (Crimean-Congo hemorrhagic fever)
Cercarial Dermatitis - see Swimmer's Itch
Cerebral Palsy
Cervical Cancer
CFS (Chronic Fatigue Syndrome)
Chagas Disease [*Trypanosoma cruzi* Infection]
Chapare Hemorrhagic Fever (CHHF)
Chest Cold - see Bronchitis
CHHF (Chapare Hemorrhagic Fever)
Chickenpox [Varicella Disease]
Chickenpox Vaccination
Chikungunya Fever (CHIKV)
CHIKV (Chikungunya Fever)
Childhood Arthritis
Childhood Injuries
Childhood Overweight and Obesity
Children's Cough and Cold Medicines - see Cough and Cold Medicines
Chlamydia [Chlamydia trachomatis Disease]
Chlamydia trachomatis Disease - see Chlamydia
*Chlamydophila* (Chlamydia) *pneumoniae* Infection
Cholera [*Vibrio cholerae* Infection]
Chronic Disease Prevention
Chronic Fatigue Syndrome (CFS)
Chronic Kidney Disease (CKD)
Chronic Obstructive Pulmonary Disease (COPD)
Chronic Wasting Disease (CWD)
Ciguatera Fish Poisoning
Ciguatoxin - see Marine Toxins
CJD, Classic (Classic Creutzfeldt-Jakob Disease)
CKD (Chronic Kidney Disease)
CKD (Kidney Disease)
Classic Creutzfeldt-Jakob Disease (CJD, Classic)
Clonorchiasis - see Clonorchis Infection
*Clonorchis* Infection [Clonorchiasis]
*Clostridium botulinim* Infection - see Botulism
*Clostridium difficile* Infection - see *C. diff.* Infection
*Clostridium perfringens* infection
*Clostridium perfringens* infection
*Clostridium tetani* Infection - see Tetanus Disease
Clotting Disorders
CMV (Cytomegalovirus Infection)
Coal Workers' Pneumoconioses - see Black Lung
Coccidioidomycosis - see Valley Fever
Cold, Common
Colorado Tick Fever (CTF)
Colorectal (Colon) Cancer
Colorectal Cancer and Genetics
Colorectal Cancer Control Program (CRCCP)
Common Cold - see Cold, Common
Concussion - see Traumatic Brain Injury
Congenital Hearing Loss - see Hearing Loss in Children
Conjunctivitis - see Pink Eye
Cooleys Anemia
COPD (Chronic Obstructive Pulmonary Disease)
*Corynebacterium diphtheriae* Infection - see Diphtheria
Cough and Cold Medicines
*Coxiella burnetii* Infection - see Q Fever
CRE (Carbapenem-resistant Enterobacteriaceae)
Creutzfeldt-Jakob Disease, Classic - see Classic Creutzfeldt-Jakob Disease TABLE 8-continued Diseases Crimean-Congo hemorrhagic fever (CCHF) [Nairovirus Infection]
CRKP (Carbapenem resistant Klebsiella pneumonia)
Crohn's Disease - see Inflammatory Bowel Disease
Cronobacter Infection
Cryptococcosis, *C. gattii*. - see *C. gattii* cryptococcosis
Cryptococcosis, *C. neoformans* - see *C. neoformans* cryptococcosis
Cryptosporidiosis - see *Cryptosporidium* Infection
*Cryptosporidium* Infection [Cryptosporidiosis]
CTF (Colorado Tick Fever)
CWD (Chronic Wasting Disease)
*Cyclospora* Infection [Cyclosporiasis]
Cyclosporiasis - see *Cyclospora* Infection
Cysticercosis
*Cystoisospora* Infection [Cystoisosporiasis]
Cystoisosporiasis - see *Cystoisospora* Infection
Cytomegalovirus Infection (CMV)
DBA (Diamond Blackfan Anemia)
Deep Vein Thrombosis (DVT)
Dengue Fever (DF)
Dengue Hemorrhagic Fever (DHF) - see Dengue Fever
Dermatophyte Infection - see Ringworm
Dermatophytes - see Ringworm
Developmental Disabilities
DF (Dengue Fever)
DHF (Dengue Hemorrhagic Fever)
Diabetes
Diamond Blackfan Anemia (DBA)
*Dientamoeba fragilis* Infection
Diet and Nutrition - see Nutrition
Diphtheria [*Corynebacterium diphtheriae* Infection]
Diphtheria Vaccination
Diphyllobothriasis - see *Diphyllobothrium* Infection
*Diphyllobothrium* Infection [Diphyllobothriasis]
*Dipylidium* Infection - see Tapeworm, Dog and Cat Flea
Dirofilariasis (Dog Heartworm)
Division of Public Health Systems and Workforce Development (DPHSWD)
Division of Public Health Systems and Workforce Development (DPHSWD) - see Division of Public Health Systems and Workforce Development
Dog Flea Tapeworm - see Tapeworm, Dog and Cat Flea
Dog Heartworm [Dirofilaria]- see Dirofilariasis (Dog Heartworm)
Dogs, Infections from
Down Syndrome [Trisomy 21]
DPHSWD (Division of Public Health Systems and Workforce Development)
Dracunculiasis - see Guinea Worm Disease
Drug Resistance - see Antibiotic and Antimicrobial Resistance
DVT (Deep Vein Thrombosis)
Dwarf Tapeworm [*Hymenolepis* Infection]
*E. coli* Infection [*Escherichia coli* Infection]
Ear Infection [Otitis Media]
Early Hearing Detection and Intervention (EHDI) - see Hearing, Early Detection & Intervention
Eastern Equine Encephalitis (EEE)
Ebola Virus Disease (EVD)
EBV Infection (Epstein-Barr Virus Infection)
Echinococcosis
EEE (Eastern Equine Encephalitis)
EHDI (Early Hearing Detection and Intervention)
Ehrlichiosis, Human
Elephantiasis - see Lymphatic Filariasis
Emerging Infectious Diseases
*Entamoeba histolytica* infection - see Amebiasis, Intestinal
Enteric Diseases from Animals - see Gastrointestinal Diseases from Animals
*Enterobius vermicularis* Infection - see Pinworm Infection
Enterovirus D68
Enterovirus Infections (Non-Polio) - see Non-Polio Enterovirus Infections
Epidemic Typhus - see Typhus Fevers
Epilepsy
Epstein-Barr Virus Infection (EBV Infection)
Ergonomic and Musculoskeletal Disorders
*Escherichia coli* Infection - see *E. coli* Infection
Esophageal Candidiasis - see Thrush
EVD (Ebola Virus Disease)
EV-D68 - see Enterovirus D68
Exserohilum rostratum (Other Pathogenic Fungi)
Extensively Drug-Resistant TB (XDR TB)
Extreme Cold [Hypothermia]
Extreme Heat [Hyperthermia]
Falls from Elevation

TABLE 8-continued

Diseases

Falls, Older Adults
Fasciitis, Necrotizing
*Fasciola* Infection [Fascioliasis]
Fascioliasis - see *Fasciola* Infection
Fasciolopsiasis - see *Fasciolopsis* Infection
*Fasciolopsis* Infection [Fasciolopsiasis]
Fetal Alcohol Syndrome
FETP - see Field Epidemiology Training Program
FETP (Field Epidemiology Training Program)
Fibromyalgia
Fifth Disease [Parvovirus B19 Infection]
Filariasis, Lymphatic
Fireworks Injuries
Flu
Folliculitis
Foodborne Illness
Food-Related Diseases
Fragile X Syndrome (FXS)
*Francisella tularensis* Infection - see Tularemia
Fungal diseases [Mycotic diseases]
Fungal Keratitis
Fungal Meningitis
Fungal Pneumonia - see Valley Fever
FXS (Fragile X Syndrome)
GAE (Granulomatous amebic encephalitis)
GAS (Group A Strep Infection)
Gastrointestinal Diseases from Animals [Zoonotic enteric diseases]
GBS (Group B Strep Infection)
GBS and Menactra Meningococcal Vaccine - see Guillain-Barré Syndrome and Menactra Meningococcal Vaccine
GDDER (Global Disease Detection and Emergency Response)
Genetics and Autism - see Autism and Genetics
Genetics and Colorectal Cancer - see Colorectal Cancer and Genetics
Genetics and Heart Disease - see Heart Disease and Genetics
Genetics and Mental Health - see Mental Health and Genetics
Genetics and Obesity - see Obesity and Genetics
Genetics and Skin Cancer - see Skin Cancer and Genetics
Genetics and Stroke - see Stroke and Genetics
Genital Candidiasis (VVC) [Vulvovaginal Candidiasis]
Genital Herpes [Herpes Simplex Virus Infection]
Genital Warts - see Human Papillomavirus Infection
German Measles (Rubella Virus)
*Giardia* Infection [Giardiasis]
Giardiasis - see *Giardia* Infection
Glanders [*Burkholderia mallei*]
*Gnathostoma* Infection - see Gnathostomiasis
Gnathostomiasis [*Gnathostoma* Infection]
Gonorrhea [*Neisseria gonorrhoeae* Infection]
Gout
Granulomatous amebic encephalitis (GAE) - see *Balamuthia* Infection
Group A Strep Infection (GAS) [Group A Streptococcal Infection]
Group A Streptococcal Infection - see Group A Strep Infection
Group B Strep Infection (GBS) [Group B Streptococcal Infection]
Group B Streptococcal Infection - see Group B Strep Infection
Guillain-Barré Syndrome and Menactra Meningococcal Vaccine
Guinea Worm Disease [Dracunculiasis]
Gynecologic Cancers
H1N1 Flu
H3N2v influenza
H5N1 - see Avian Influenza
Haemophilus influenzae Serotype b - see Hib Infection
Haemophilus influenzae Infection (including Hib Infection)
Hand, Foot, and Mouth Disease (HFMD)
Hansen's Disease
Hantavirus Pulmonary Syndrome (HPS)
Hazardous Drug Exposures in Healthcare
Head Lice [*Pediculus humanus capitis*]
Health Disparities in Cancer
Health Disparities in HIV/AIDS, Viral Hepatitis, STDs, and TB
Health Security - see Global Health Security
Healthcare Associated Infections
Healthy Pets, Healthy People - see Animal-Related Diseases
Hearing Loss in Children
Heart Disease [Cardiovascular Health]
Heart Disease and Genetics
Heat Stress
Hemochromatosis
Hemoglobinopathies TABLE 8-continued Diseases Hemophilia
Hemophilia Treatment Centers (HTC)
Hemorrhagic Fevers, Viral - see Viral Hemorrhagic Fevers
Hendra Virus Disease (HeV Infection)
Hepatitis A Vaccination
Hepatitis B Vaccination
Hepatitis, Viral - see Viral Hepatitis
Hereditary Bleeding Disorders - see Hemophilia
Herpes B virus - see B virus Infection
Herpes Simplex Virus Infection - see Genital Herpes
Herpes Zoster - see Shingles
Herpes Zoster Vaccination - see Shingles Vaccination
Herpes, Genital - see Genital Herpes
Herpesvirus B - see B virus Infection
Herpesvirus simiae - see B virus Infection
*Heterophyes* Infection [Heterophyiasis]
Heterophyiasis - see *Heterophyes* Infection
HeV Infection (Hendra Virus Disease)
HFMD (Hand, Foot, and Mouth Disease)
Hib Infection [*Haemophilus influenzae* Serotype b]
Hib Vaccine (*Haemophilus influenzae* Serotype b Vaccination)
High Blood Pressure
*Histoplasma capsulatum* Infection [Histoplasmosis]
Histoplasmosis - see *Histoplasma capsulatum* Infection
Histoplasmosis [*Histoplasma capsulatum* Infection]
HIV/AIDS
HIV/AIDS and STDs
Hookworm, Human [*Ancylostoma duodenale* Infection, *Necator americanus* Infection]- see
Human Hookworm
Hookworm, Zoonotic - see Zoonotic Hookworm
Horses, Infections from
Hot Tub Rash [*Pseudomonas dermatitis* Infection]
HPIV (Human Parainfluenza Viruses)
HPS (Hantavirus Pulmonary Syndrome)
HPV Infection (Human Papillomavirus Infection)
HPV Vaccination (Human Papillomavirus Vaccination)
HPV-Associated Cancers
HTC (Hemophilia Treatment Centers)
Human Ehrlichiosis - see Ehrlichiosis, Human
Human Hookworm [*Ancylostoma duodenale* Infection, *Necator americanus* Infection]
Human Immunodeficiency Virus - see HIV/AIDS
Human Papillomavirus Infection (HPV Infection)
Human Papillomavirus Vaccination (HPV Vaccination)
Human Parainfluenza Viruses (HPIV)
*Hymenolepis* Infection - see Dwarf Tapeworm
Hypertension - see High Blood Pressure
Hyperthermia - see Extreme Heat
Hypothermia - see Extreme Cold
IBD (Inflammatory Bowel Disease)
IMMPaCt (International Micronutrient Malnutrition Prevention and Control Program) - see
Micronutrient Malnutrition
Impetigo - see Group A Strep Infection
including Hib Infection (*Haemophilus influenzae* Infection)
Infectious Mononucleosis - see Epstein-Barr Virus Infection
Infertility
Inflammatory Bowel Disease (IBD)
Influenza
Influenza and Cancer - see Cancer and Flu
Influenza in Pigs - see Swine Influenza
Influenza Vaccination
Influenza, Avian - see Avian Influenza
Influenza, Pandemic - see Pandemic Flu
Injury, Healthy Swimming and Recreational Water
International Micronutrient Malnutrition Prevention & Control Program (IMMPaCt) - see
Micronutrient Malnutrition
Intestinal Amebae Infection, Nonpathogenic - see Nonpathogenic (Harmless) Intestinal
Protozoa
Invasive Candidiasis
Iron Deficiency - see Anemia
Iron Overload [Hemochromatosis]- see Hemochromatosis
Iron Storage Disease
*Isospora* Infection [Isosporiasis]- see *Cystoisospora* Infection
Japanese Encephalitis (JE)
Jaundice - see Newborn Jaundice
JE (Japanese Encephalitis)
*K. pneumoniae* (*Klebsiella pneumoniae*)
Kala-Azar - see *Leishmania* Infection
Kawasaki Syndrome (KS)

TABLE 8-continued

Diseases

Keratitis, Fungal - see Fungal Keratitis
Kernicterus - see Newborn Jaundice
KFD (Kyasanur Forest disease)
Kidney Disease (CKD)
*Klebsiella pneumoniae* (*K. pneumoniae*)
KS (Kawasaki Syndrome)
Kyasanur Forest disease (KFD)
La Crosse Encephalitis (LAC)
La Crosse Encephalitis virus (LACV) - see La Crosse Encephalitis
LAC (La Crosse Encephalitis)
LACV (La Crosse Encephalitis virus)
Lassa Fever
Latex Allergies
LCM (Lymphocytic Choriomeningitis)
Lead Poisoning
Legionellosis - see Legionnaires' Disease
Legionnaires' Disease [Legionellosis]
*Leishmania* Infection [Leishmaniasis]
Leishmaniasis - see *Leishmania* Infection
Leprosy - see Hansen's Disease
*Leptospira* Infection [Leptospirosis]
Leptospirosis - see *Leptospira* Infection
Lice
*Listeria* Infection [Listeriosis]
Listeriosis - see *Listeria* Infection
Liver Disease and Hepatitis - see Viral Hepatitis
Loa loa Infection - see Loiasis
Lockjaw - see Tetanus Disease
Lockjaw Vaccination - see Tetanus (Lockjaw) Vaccination
Loiasis [Loa loa Infection]
Lou Gehrig's Disease - see ALS
LUHF (Lujo Hemorrhagic Fever)
Lujo Hemorrhagic Fever (LUHF)
Lung Cancer
Lupus (SLE) [Systemic lupus erythematosus]
Lyme Disease [*Borrelia burgdorferi* Infection]
Lymphatic Filariasis
Lymphedema - see Lymphatic Filariasis
Lymphocytic Choriomeningitis (LCM)
MAC (Mycobacterium avium Complex)
Mad Cow Disease (BSE) - see Bovine Spongiform Encephalopathy
Malaria
Marburg Hemorrhagic Fever
Marine Toxins
MD (Muscular Dystrophy)
MDR TB (Multidrug-Resistant TB)
Measles
Melioidosis [*Burkholderia pseudomallei* Infection]
Meningitis
Meningococcal Disease
Meningococcal Vaccination
Men's Health
Mental Health
Mental Health and Genetics
Mental Retardation
MERS-CoV (Middle East Respiratory Syndrome Coronavirus)
Methicillin Resistant *Staphylococcus aureus* - see MRSA
Micronutrient Malnutrition
Microsporidia Infection
Middle East Respiratory Syndrome Coronavirus (MERS-CoV)
MMR Vaccination
Molluscum Contagiosum
Monkey B virus - see B virus Infection
Monkeypox
Monkeypox Vaccination
Mononucleosis, Infectious - see Epstein-Barr Virus Infection
Motor Vehicle Injuries
Mouse and Rat Control - see Rodents, Diseases from
MRSA [Methicillin Resistant *Staphylococcus aureus*]
Mucormycosis
Mucus - see Cold, Common
Multidrug-Resistant TB (MDR TB)
Multiple organ dysfunction syndrome - see Sepsis
Mumps
Muscular Dystrophy (MD)
Musculoskeletal Disorders - see Ergonomic and Musculoskeletal Disorders
Mycobacterium abscessus Infection
Mycobacterium avium Complex (MAC)

TABLE 8-continued

Diseases

Mycobacterium tuberculosis Infection - see Tuberculosis
*Mycoplasma pneumoniae* Infection
Mycotic diseases - see Fungal diseases
Myelomeningocele - see Spina Bifida
Myiasis
*Naegleria* Infection [Primary Amebic Meningoencephalitis (PAM)]
*Nairovirus* Infection - see Crimean-Congo hemorrhagic fever
National Amyotrophic Lateral Sclerosis (ALS) Registry - see ALS
Necrotizing Fasciitis - see Group A Strep Infection
Neglected Tropical Diseases (NTD)
Neisseria gonorrhoeae Infection - see Gonorrhea
Neurocysticercosis - see Cysticercosis
Newborn Hearing - see Hearing, Early Detection & Intervention
Newborn Jaundice [Kernicterus]
*Nocardia asteroides* Infection - see Nocardiosis
Nocardiosis [*Nocardia asteroides* Infection]
Nonpathogenic (Harmless) Intestinal Protozoa
Non-Polio Enterovirus Infections
Norovirus Infection
Norwalk-like Viruses (NLV) - see Norovirus Infection
NTD (Neglected Tropical Diseases)
OA (Osteoarthritis)
Obesity and Genetics
Obesity and Overweight
Obesity and Overweight, Childhood - see Childhood Overweight and Obesity
Occupational Cancers
Occupational Skin Conditions - see Skin Conditions, Occupational
Occupational Stress - see Stress, Occupational
OHF (Omsk hemorrhagic fever)
Omsk hemorrhagic fever (OHF)
Onchocerciasis - see River Blindness
Opisthorchis Infection
Oral Cancer
Orf Virus Infection - see Sore Mouth Infection
Oropharyngeal Candidiasis - see Thrush
Oroya fever - see Carrion's disease
Osteoarthritis (OA)
Osteoporosis - see Bone Health
Otitis Media - see Ear Infection
Outbreaks
Ovarian and Breast Cancer and Family Health History - see Breast and Ovarian Cancer and Family Health History
Ovarian Cancer
PAD (Peripheral Arterial Disease)
Pandemic Flu
Paragonimiasis - see Paragonimus Infection
*Paragonimus* Infection [Paragonimiasis]
Parainfluenza - see Human *Parainfluenza* Viruses
Parasitic Diseases
Parvovirus B19 Infection - see Fifth Disease
PCP (*Pneumocystis* pneumonia)
PCV (Pneumococcal Conjugate Vaccine)
PE (Pulmonary Embolism)
Pedestrian Injury
Pediculus humanus capitis - see Head Lice
Pediculus humanus corporis - see Body Lice
Pelvic Inflammatory Disease (PID)
Peripheral Arterial Disease (PAD)
Peripheral Arterial Insufficiency - see Peripheral Arterial Disease
Peripheral Arterial Occlusive Disease - see Peripheral Arterial Disease
Peripheral Vascular Disease - see Peripheral Arterial Disease
Pertussis (Whooping Cough)
Pertussis (Whooping Cough) Vaccination
Pet-Related Diseases - see Animal-Related Diseases
Phthiriasis - see Pubic Lice
PID (Pelvic Inflammatory Disease)
Pigs, Influenza in - see Swine Influenza
Pink Eye [Conjunctivitis]
Pinworm Infection [*Enterobius vermicularis* Infection]
Plague [*Yersinia pestis* Infection]
Pneumococcal Conjugate Vaccine (PCV)
Pneumococcal Disease
Pneumococcal Polysaccharide Vaccine (PPV)
Pneumoconioses, Coal Workers'- see Black Lung
*Pneumocystis* carinii Pneumonia (PCP) Infection - see *Pneumocystis* pneumonia
*Pneumocystis jirovecii* pneumonia (previously *Pneumocystis* carinii) - see *Pneumocystis* pneumonia

TABLE 8-continued

Diseases

*Pneumocystis* pneumonia (PCP) [*Pneumocystis jirovecii* pneumonia (previously *Pneumocystis carinii*)]
Pneumonia
Polio Infection [Poliomyelitis Infection]
Polio Vaccination [Poliomyelitis Vaccination]
Poliomyelitis Infection - see Polio Infection
Poliomyelitis Vaccination - see Polio Vaccination
Pontiac Fever - see Legionnaires' Disease
Powassan (POW) virus
Poxvirus Infections
PPV (Pneumococcal Polysaccharide Vaccine)
Primary Amebic Meningoencephalitis (PAM) - see *Naegleria* Infection
Prion Diseases (TSEs) [Transmissible spongiform encephalopathies]
Prostate Cancer
*Pseudomonas dermatitis* Infection - see Hot Tub Rash
Psittacosis
Psoriasis
Pubic Lice [Phthiriasis]
Pulmonary Embolism (PE) - see Deep Vein Thrombosis
Pulmonary Hypertension
Q Fever [*Coxiella burnetii* Infection]
RA (Rheumatoid Arthritis)
Rabies
Raccoon Roundworm Infection [*Baylisascaris* Infection]
Rat-Bite Fever (RBF) [*Streptobacillus moniliformis* Infection]
RBF (Rat-Bite Fever)
Recreational Water Illness (RWI)
Reptiles, Infections from
Respiratory Syncytial Virus Infection (RSV)
Rheumatoid Arthritis (RA)
*Rickettsia rickettsii* Infection - see Rocky Mountain Spotted Fever
*Rickettsia*, Spotted Fever Group - see Spotted Fever Group *Rickettsia*
Rickettsial Diseases
Rift Valley Fever (RVF)
Ringworm [Dermatophyte Infection]
Ringworm [Dermatophytes]
Ringworm in Animals
River Blindness [Onchocerciasis]
RMSF (Rocky Mountain Spotted Fever)
Rocky Mountain Spotted Fever (RMSF) [*Rickettsia rickettsii* Infection]
Rodent Control - see Rodents, Diseases from
Rodents - see Rat-Bite Fever
Rodents, Diseases from
Rotavirus Infection
RSV (Respiratory Syncytial Virus Infection)
Rubella (German Measles) Vaccination
Rubeola - see Measles
Runny Nose - see Cold, Common
RVF (Rift Valley Fever)
RWI (Recreational Water Illness)
*Salmonella typhi* Infection - see Typhoid Fever
*Salmonella* Infection [Salmonellosis]
Salmonellosis - see *Salmonella* Infection
*Sappinia diploidea* and *Sappinia pedata* - see *Sappinia* Infection
*Sappinia* Infection [*Sappinia diploidea* and *Sappinia pedata*]
SARS [Severe Acute Respiratory Syndrome]
Scabies
Scarlet Fever
*Schistosoma* Infection - see Schistosomiasis
Schistosomiasis [*Schistosoma* Infection]
Seasonal Flu
Sepsis [Septicemia]
Septic shock - see Sepsis
Septicemia - see Sepsis
Severe Acute Respiratory Syndrome - see SARS
Sexually Transmitted Disease Surveillance Reports
Sexually Transmitted Diseases (STDs)
SFGR (Spotted Fever Group Rickettsia)
*Shigella* Infection [Shigellosis]
Shigellosis - see *Shigella* Infection
Shingles [Varicella Zoster Virus (VZV)]
Shingles Vaccination
Sickle Cell Disease
SIDS (Sudden Infant Death Syndrome)
Sinus Infection [Sinusitus]
Sinusitus - see Sinus Infection
Skin Cancer
Skin Cancer and Genetics TABLE 8-continued Diseases Skin Conditions, Occupational
SLE (Lupus)
Sleep and Sleep Disorders
Sleeping Sickness [African Trypanosomiasis]
Smallpox [Variola Major and Variola Minor]
Smallpox Vaccination
Smoking and Tobacco Use
Sodium - see Salt
Soil Transmitted Helminths
Sore Mouth Infection [Orf Virus Infection]
Sore Throat
Southern Tick-Associated Rash Illness (STARI)
Spina Bifida [Myelomeningocele]
*Spirillum minus* Infection - see Rat-Bite Fever
*Sporothrix schenckii* infection - see Sporotrichosis
Sporotrichosis
Sporotrichosis [*Sporothrix schenckii* infection]
Spotted Fever Group *Rickettsia* (SFGR)
Staph - see *Staphylococcus aureus* Infection
*Staphylococcus aureus* Infection
START (Southern Tick-Associated Rash Illness)
STDs (Sexually Transmitted Diseases)
STDs and HIV/AIDS - see HIV/AIDS and STDs
Strep Infection, Group A - see Group A Strep Infection
Strep Infection, Group B - see Group B Strep Infection
Strep Throat - see Sore Throat
*Streptobacillus moniliformis* Infection - see Rat-Bite Fever
*Streptococcus pneumoniae* Infection
Stress, Occupational
Stroke
Stroke and Genetics
Strongyloidiasis - see *Strongyloides* Infection [Strongyloidiasis]
Strongyloidiasis - see Strongyloidiasis - see *Strongyloides* Infection
Sudden Infant Death Syndrome (SIDS)
surgical site infection (SSI)
Surveillance Reports, Sexually Transmitted Disease - see Sexually Transmitted Disease
Surveillance Reports
Swimmer's Itch [Cercarial Dermatitis]
Swimming-related Illness - see Recreational Water Illness
Swine Influenza
Symptom Relief for Upper Respiratory Infections
Syphilis [*Treponema pallidum* Infection]
Systemic lupus erythematosus - see Lupus
*Taenia* Infection - see Tapeworm Infection
Tapeworm Infection [*Taenia* Infection]
Tapeworm, Dog and Cat Flea [*Dipylidium* Infection]
TB (Tuberculosis)
TB (Tuberculosis) Vaccination
TB and HIV Coinfection
TBI (Traumatic Brain Injury)
Testicular Cancer
Tetanus (Lockjaw) Infection
Tetanus (Lockjaw) Vaccination
Tetanus Disease [*Clostridium tetani* Infection]
Thalassemia - see Cooleys Anemia
Thoracic Aortic Aneurysm - see Aortic Aneurysm
Throat, Sore - see Sore Throat
Throat, Strep - see Sore Throat
Thrombophilia - see Clotting Disorders
Thrombosis - see Clotting Disorders
Thrush [Oropharyngeal Candidiasis]
Tickborne Diseases - see Ticks
Ticks
Tinea - see Ringworm
Tobacco Use, Smoking and - see Smoking and Tobacco Use
Tourette Syndrome (TS)
*Toxocara* Infection - see Toxocariasis
Toxocariasis [*Toxocara* Infection]
*Toxoplasma* Infection - see Toxoplasmosis
Toxoplasmosis [*Toxoplasma* Infection]
Trachoma Infection
Transmissible spongiform encephalopathies - see Prion Diseases
Traumatic Brain Injury (TBI)
Traumatic Occupational Injuries
Trench fever [*Bartonella quintana* Infection]
*Treponema pallidum* Infection - see Syphilis
Trichinellosis (Trichinosis)
*Trichomonas* Infection - see Trichomoniasis TABLE 8-continued Diseases Trichomoniasis [*Trichomonas* Infection]
Trichuriasis - see Whipworm Infection
Trisomy 21 - see Down Syndrome
*Trypanosoma cruzi* Infection - see Chagas Disease
Trypanosomiasis, African - see Sleeping Sickness
TS (Tourette Syndrome)
TSEs (Prion Diseases)
Tuberculosis (TB) [*Mycobacterium tuberculosis* Infection]
Tuberculosis (TB) Vaccination
Tuberculosis and HIV Coinfection - see TB and HIV Coinfection
Tuberculosis Skin Test - see TB Testing & Diagnosis
Tuberculosis Training - see TB Education and Training Network
Tuberculosis Vaccine (BCG)
Tularemia [*Francisella tularensis* Infection]
Typhoid Fever [*Salmonella typhi* Infection]
Typhoid Fever Vaccination
Typhus Fevers
Ulcerative Colitis - see Inflammatory Bowel Disease
Undulant Fever - see Brucella Infection
Unexplained Respiratory Disease Outbreaks (URDO)
Upper Respiratory Infection Symptom Relief - see Symptom Relief for Upper Respiratory Infections
URDO (Unexplained Respiratory Disease Outbreaks)
Uterine Cancer
Vaginal and Vulvar Cancers
Vaginal Candidiasis - see Genital Candidiasis
Valley Fever [Coccidioidomycosis]
Vancomycin-Intermediate/Resistant *Staphylococcus aureus* Infections [VISA/VRSA]
Vancomycin-resistant Enterococci Infection (VRE)
Variant Creutzfeldt-Jakob Disease (vCJD)
Variant Viruses - see Influenza
Varicella Disease - see Chickenpox
Varicella Zoster Virus (VZV) - see Shingles
Varicella-Zoster Virus Infection
Variola Major and Variola Minor - see Smallpox
vCJD (Variant Creutzfeldt-Jakob Disease)
verruga peruana - see Carrion's disease
VHF (Viral Hemorrhagic Fevers)
*Vibrio cholerae* Infection - see Cholera
*Vibrio* Illness [Vibriosis]
Vibriosis - see Vibrio Illness
Viral Hemorrhagic Fevers (VHF)
Viral Hepatitis
Viral Meningitis [Aseptic Meningitis]
VISA/VRSA - see Vancomycin-Intermediate/Resistant *Staphylococcus aureus* Infections
Vision Impairment
VRE (Vancomycin-resistant Enterococci Infection)
Vulvovaginal Candidiasis - see Genital Candidiasis
VVC (Genital Candidiasis)
VZV (Varicella Zoster Virus) - see Shingles
Water-Related Diseases
Weight, Healthy - see Healthy Weight
West Nile Virus Infection (WNV Infection)
Whipworm Infection [Trichuriasis]
Whitmore's Disease - see Melioidosis
Whooping Cough - see Pertussis (Whooping Cough)
Wildlife, Infections from
WNV Infection (West Nile Virus Infection)
Women's Bleeding Disorders
XDR TB (Extensively Drug-Resistant TB)
Xenotropic Murine Leukemia Virus-related Virus Infection - see XMRV Infection
XMRV Infection [Xenotropic Murine Leukemia Virus-related Virus Infection]
Yeast Infection - see Genital Candidiasis
Yellow Fever
Yellow Fever Vaccination
*Yersinia enterocolitica* Infection - see Yersiniosis
*Yersinia pestis* Infection - see Plague
Yersiniosis [*Yersinia enterocolitica* Infection]
Zoonotic Diseases from Animals - see Animal-Related Diseases
Zoonotic enteric diseases - see Gastrointestinal Diseases from Animals
Zoonotic Hookworm
Zoster - see Shingles
Zygomycosis - see Mucormycosis

III. System and Method to Control the Delivery of Oral Medications

Various embodiments will be described hereinafter with reference to the accompanying drawings. These embodiments are illustrated and described by example only and are not intended to be limiting. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

The word "exemplary" is used herein to mean "serving as an example, instance, or illustration". Any embodiment described herein as "exemplary" or "example" is not necessarily to be construed as preferred or advantageous over other embodiments. Likewise, the term "embodiments of the invention" does not require that all embodiments of the invention include the discussed feature, advantage or mode of operation.

Further, many embodiments are described in terms of sequences of actions to be performed by, for example, elements of a computing device. It will be recognized that various actions described herein can be performed by specific circuits (e.g., application specific integrated circuits (ASICs)), by program instructions being executed by one or more processors, or by a combination of both. Additionally, these sequences of actions described herein can be considered to be embodied entirely within any form of computer readable storage medium having stored therein a corresponding set of computer instructions that upon execution would cause an associated processor to perform the functionality described herein. Thus, the various aspects of the invention may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

FIG. 1 illustrates an exemplary embodiment of the present invention, an integrated drug dispensing and disease management system composed of a Drug Specific App 10 which contains a Drug Specific Dispensing Algorithm 15 resident on an Interface Device (Smart Phone, computer Tablet, portable or desktop computer, standalone drug dispenser, etc. with Internet communications capabilities) 20 used to control dispensing by a (single or multidrug) Drug Dispenser 30; an Integrated Support Center 40; a Patient 50; a Prescriber 60; and the Patient's Electronic Medical Record 70.

Figure 2:
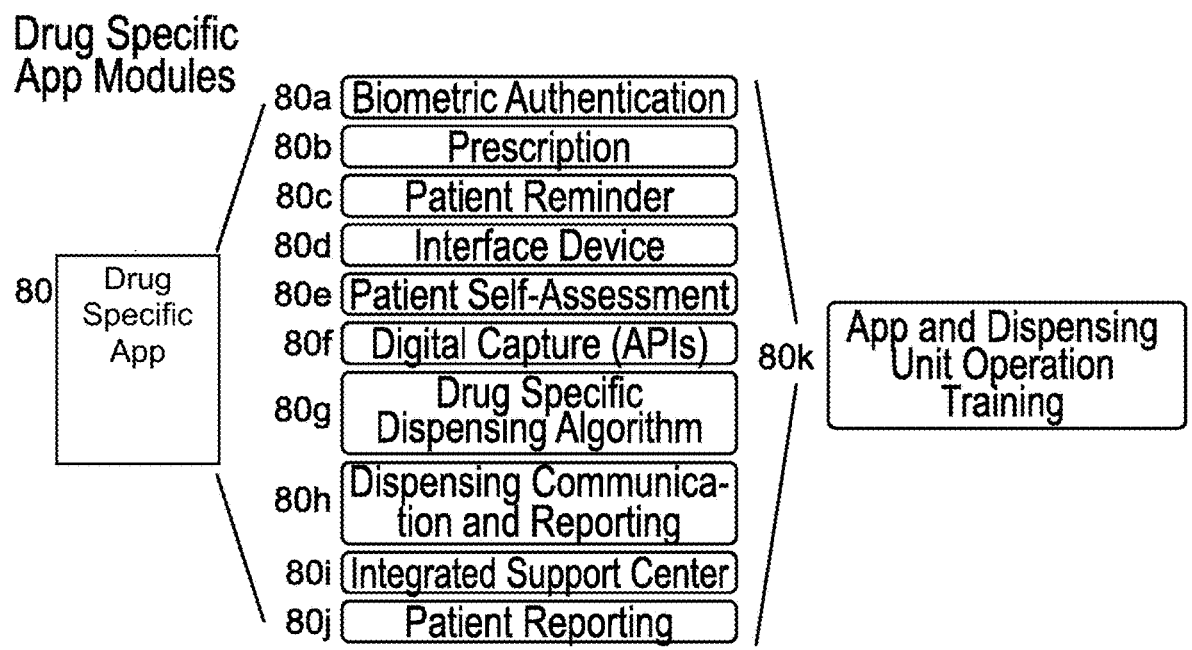
FIG. 2 is an exemplary embodiment showing a Drug Specific App which controls the Drug Dispensing Unit.

FIG. 2 is an exemplary embodiment depicting a Drug Specific Dispensing App 80 which resides on an Interface Device 20 and controls drug dispensing. When the Patient 50 is prescribed a Drug, the Patient 50 is trained on the operation of the Drug Specific Dispensing App 80 and the related Drug Dispenser 30 using the Apps training interface.

In this embodiment of the invention, the Drug Specific App 80 is comprised of the following software modules: (i) Biometric Authentication 80a, (ii) Prescription 80b module which can be programmed remotely by the Integrated Support Center 40, (iii) Patient Reminder 80c, (iv) Interface Device 80d, (v) Patient Self-Assessment 80e module which is unique for each drug, (vi) Digital Capture (APIs) 80f, (vii) the Drug Specific Dispensing Algorithm 80g which is unique for each drug, (viii) Dispensing Communication and Reporting 80h, (ix) the Integrated Support Center 80i, (x) the Patient Reporting 80j, and (xi) the App and Dispensing Unit Operation Training Interface 80k.

The following are exemplary descriptions of the FIG. 2 embodiments of the invention:

Biometric Authentication module 80a encompasses the utilization of a biometric authentication screen and/or digital interface which allows the patient, upon authentication, to automatically move to the Patient Self-Assessment screens 100, 102, 104 if: (i) the authentication routine recognizes the Drug Dispenser's 30 serial number to be one that was registered to the Patient 50, (ii) digitally Handshake with the Drug Specific App 10 and (iii) the Biometric Authentication 80a recognizes the Patient 50. If the Biometric Authentication 80a does not recognize the Patient 50, it asks the Patient 50 to try again. After a given number of tries, it alerts the patient to talk with the Integrated Support Center 40 and alerts the Integrated Support Center 40 of the failed attempts and lists the Patient 50 for a follow-up call if the drug has not been properly dispensed within a drug specific timeframe. If the App 50 does not recognize the Drug Dispenser 30, the patient gets an alert screen explaining why it does not recognize the dispenser, this may include but is not limited to: (i) unable to locate the Drug Dispenser 30, (ii) the Drug Dispenser 30 does not have the right serial number, etc. Simultaneously, if the App 10 senses that the Drug Dispenser does not have the right serial number, it will send a message to the Integrated Support Center 40 indicating the serial number of the recognized Drug Dispenser for follow-up action by the Integrated Support Center 40. One alternative for the Integrated Support Center 40 is to lock the App screen to only give the Patient 50 the choice of calling the Integrated Support Center 40 to resolve his dispensing issue.

The Prescription module 80b, which is unique to the drug, encompasses the ability of the Prescriber 60, other authorized healthcare professionals, or the Integrated Support Center 40 to input the prescribing information into the Drug Specific App 10. After loading the Drug Specific App 10 onto the Interface Device 20, the person entering the prescription information begins by entering the drugs Brand and/or generic name, strength/dosage, NCD number, Batch Number, any pertinent required contact information in case of an overdose or emergency, and the drug's expiration date. This input can be done manually and/or via a barcode scan of the Individualized Drug Cassette 170. The prescribing information defines the dosing strength and administration schedule (e.g, q.d., b.i.d., t.i.d., q.i.d., q.h.s., −X a day, −X per week, −X per month, q.4h, q.6h, q.o.d., a.c., p.c., prn, etc.). The prn dosing, and/or for example the patient self-analgesia dosing, can be designated to allow the Patient 50 to self-medicate using multiple smaller doses to a maximum cumulative dose over a specified period of time. Once the maximum does is dispensed, the Drug Dispenser is locked by the Drug Specific App 10 until the next dosing period begins and the patient enters the requisite information to enable the Drug Specific App 10 to signal the Drug Dispenser to dispense.

The Patient Reminder module 80c encompasses the ability of the Drug Specific App 10 to alert the Patient 50 using different methodologies including but not limited to: (i) initiating a phone call, (ii) buzzing the device, (iii) sending an email message, (iv) sending a text message, and/or (v) having the Integrated Support Center 40 call the Patient 50, etc.

When the phone call is initiated, the Drug Specific App 10 is shown on the Smart Phone's screen. When the phone is turned on or unlocked, the screen automatically moves to the Biometric Authentication 90 screen. If the Drug Specific App 10 is clicked on a Smart Phone, it opens to the Biometric Authentications 90 screen.

The Interface Device module 80d encompasses many functions: (i) home for the Drug Specific App 10, (ii) enables the Drug Specific App 10 to utilize the Interface Device features to facilitate the Drug Specific App's interface with the Patient 50, (iii) uses the Interface Device's 20 Wi-Fi communications capability to interface with the Drug Dispenser 30 and its Internet communications capability to interface with the Integrated Support Center 40, (iv) uses the phone to call the Integrated Support Center 40, and utilizes the Interface Device's 20 memory to store the prescription, dispensing history, and the Patient Self-Assessment (see illustrative examples in FIG. 4) and digital (see representative examples under FIG. 5) physiological, psychological, lifestyle, currently taken medications, and environmental data.

The Patient 50 is, for example, able to utilize the Interface Device's 20 navigation capabilities to move between screens and to correct prior inputs before exiting by selecting the dispense or exit buttons.

Utilizes the Interface Device's 20 GPS device to capture the location when the medication is dispensed.

Patient Self-Assessment module 80e is specific for each drug based upon, for example, the drug's side effects, potential drug interactions, implications of under and/or overdosing, efficacy measures, dosing schedule, drug strength, single or multidrug regimen, effects of weight gain, aging, development of comorbidities, etc. Certain Patient Self-Assessment 100, 102, 104 screens will, for example, incorporate known self-assessment scales or will incorporate self-assessment screens specifically developed for the specific drug. The screens may also be those which are designed to capture Patient specific information required by regulatory agencies for the subsequent approval of the drug and/or for post marketing studies.

The Digital Capture (APIs) module 80f encompasses, as an exemplary, digital information that is integrated via the Drug Specific App 10 via Digital Capture from, as examples, a wearable monitoring device 110, a digital scale 112, a third-party monitoring App on a smart phone 114, a hand held diagnostic device 116, a lifestyle monitor 117, a digitalized home diagnostic or self-diagnostic 118, a swallowed tracking and/or diagnostic aid, a drug tracking chip, radio frequency identification device (RFID), or care giver or parent patient assessments and/or journal entries, etc.

The Drug Specific Dispensing Algorithm module 80g encompasses, as an example, the Product Expiration 122 date, Properly Stored 123 information (for example, temperature, moisture, etc.), one or more Patient Self-Assessment 125, 126 and/or one or more Digitally Captured 127 values, the Dispensing Algorithm 128, the Dispense 129 command screen and interface with the Drug Dispenser 30, and patient feedback and instruction screens 130, 132, 134, 136, 138, 140, 142, 144, 146, 148, 150, 152, etc.

The Dispensing Communications and Reporting 80h module encompasses, for example, the interface between: (i) the Drug Specific App 10 and the Drug Dispenser 30 via the Interface Device 20; (ii) the interfaces between the Drug Specific App 10 and any proprietary or third-party digital devices, data aggregation devices, computer databases, diagnostic devices, and medication tracking devices, etc., for example, those digital devices listed under FIG. 5, e.g., 110, 112, 114, 116, 117, 118; (iii) the interface between the Drug Specific App and the computer servers and the respective databases that store information captured by the Drug Specific App 10 and data and reports created by the Integrated Support Center 40 and accessed by the Drug Specific App 10; the interface between the Integrated Support Center 40 and the Drug Specific App 10 utilized to change the prescription on the Drug Specific App 10 as well as to update the App software as required, etc.

The Integrated Support Center 80i module encompasses, for example, (i) securely handshaking/connecting the Drug Specific App 10 to the Integrated Support Center 40, (ii) sending to and receiving alerts from the Integrated Support Center 40, (iii) enabling the Integrated Support Center 40 to lock or unlock the Drug Dispenser 30, (iv) alert the Integrated Support Center 40 of unusual attempts to open the Drug Dispenser 30, (v) the ability of the Integrated Support Center 40 to remotely update the Drug Specific App software, and (vi) enables the Drug Specific App 10 to access patient reports, charts, and graphs, (vii) enables the patient to require a refill prescription be sent to his/her pharmacy for refill, etc.

The Patient Reporting 80j module encompasses, as an example: (i) an ability by the Patient 50 to request certain reports, e.g., the last time the Patient 50 took the medication, prescription information details, drug details (brand and generics names, batch number, expiration date, doses remaining, reorder information, drug interactions, typical side effects, etc.; (ii) graphs and charts created by the Drug Specific App 10 based upon Interface Device 20 stored information; (iii) graphs, charts and/or reports downloaded from the Integrated Support Center's servers, etc.

The App and Dispensing Unit Operation Training Module 80k encompasses, as an example, (i) a hot link to a video library resident on the Integrated Support Center's servers, You Tube, and/or other consumer video services covering all aspects of utilizing the Drug Specific App 10, using and troubleshooting the Drug Dispenser 30, (ii) a step by step tutorial resident on the Interface Device 20, (iii) a hot linked "help" button on each respective screen allowing the Patient 50 to bring up usage instructions for the respective screen without interrupting the sequence of entering the required prescription information or selecting a particular command, etc.

FIG. 3 The exemplary embodiment of the Biometric Authentication 90 interface encompasses a system that is compliant with the Health Insurance Portability and Accountability Act (HIPAA), which sets the standard for protecting sensitive patient data. This means that all the required physical, network, and process security measures are in place and followed and incorporated herein by reference.

FIG. 4 The exemplary embodiment of the Patient Self-Reporting Screens 100, 102, 104 encompass, for example, an abdominal pain self-reporting scale adapted from Wong Baker Faces 100; the stool consistency utilizes the Bristol Stool Scale, a well-accepted stool measure 102; and the current abdominal discomfort scale was developed by MMC International from the Defense and Veterans Pain Rating Scale 104. These are examples of patient self-reporting screens that can be utilized in the embodiment as an input to the Drug Specific Dispensing Algorithm 15 to decide whether or not to dispense. The scales can be created, adapted, or integrated to capture the desired patient self-reported information. This can be, for example, for clinical trials, post marketing surveillance, and/or for incorporation into the Drug Specific Dispensing Algorithm 15.

FIG. 5 The exemplary embodiment of the Digitally Captured information 110, 112, 114, 116, 117, 118 is illustrative for the types of digital information which can be collected and integrated into the Decision Tree/logic in the respective Drug Specific Dispensing Algorithms 15. The availability of disease specific Apps and related disease or condition specific digitalized health information is rapidly emerging, making the examples in FIG. 5 wanting not only for the disease information but for lifestyle, medications being taken, digital medication diagnostic and tracking devices, and environmental input, etc.

Figure 6:
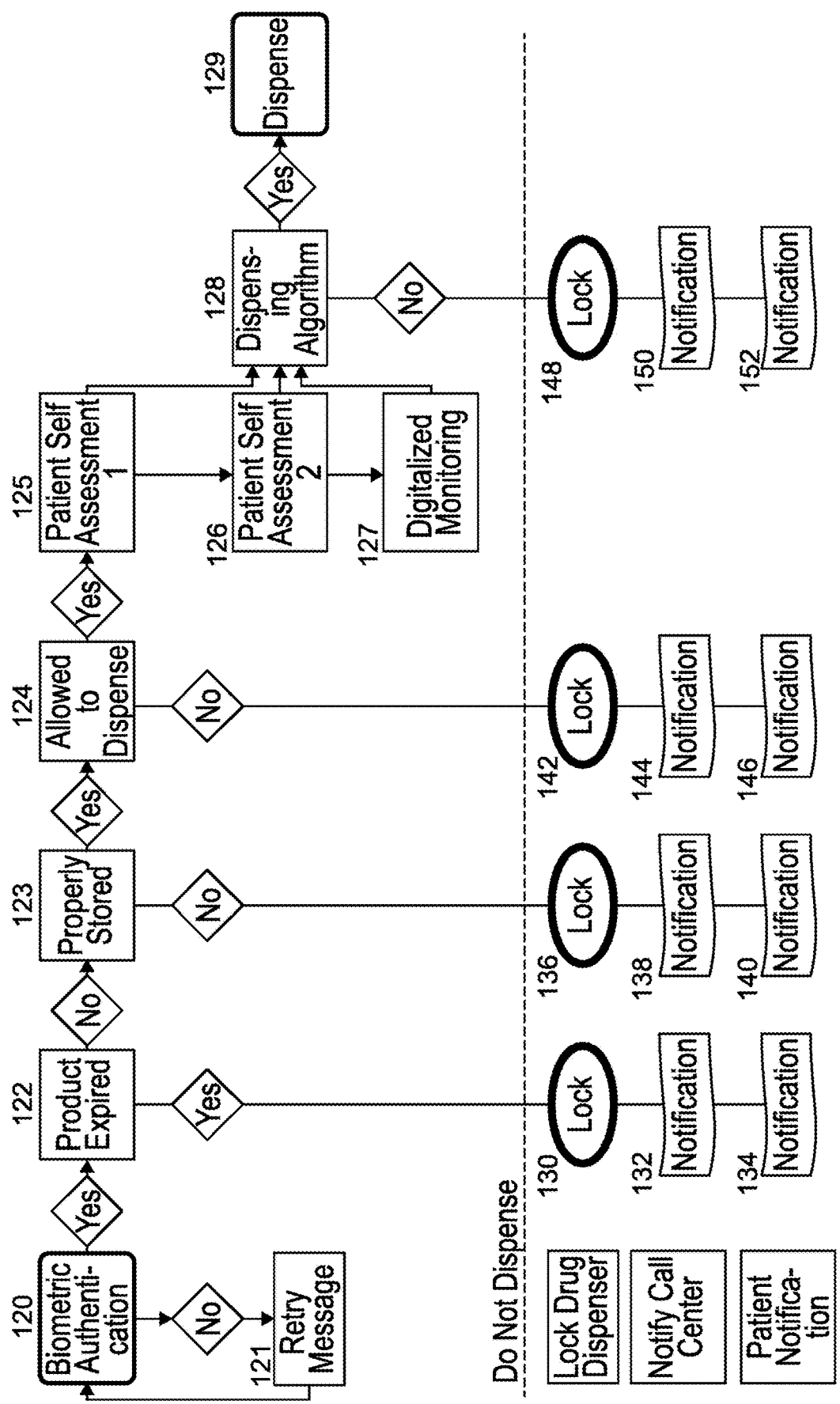
FIG. 6 is an exemplary embodiment of a flow chart/decision tree used by the Drug Dispensing Algorithm.

FIG. 6 The exemplary embodiment of a Drug Specific Dispensing Algorithm 120, 121, 122, 123, 124, 125, 126, 127, 128, 129, 130, 132, 134, 136, 138, 140, 142, 144, 146, 148, 150, 152 is illustrative of the Decision Tree, sequencing, and messaging that is utilized by each Drug Specific Dispensing Algorithm 15. Biometric Authorization 120, 121, Product Expiration 122, and Properly Stored 123 are constant variables in the dispensing decision. The respective messages are either standard, as an example those related to locking the Drug Dispenser 130, 136, 142, 148 or Notify Call Center 132, 138, 144, 150, or Product Expired 132, 134 or the drug was not Properly Stored 138, 140, etc. Screens indicating why a drug is not "Allowed to Dispense" are specifically adapted to the drug and report the reasons why the drug was not dispensed 144, 146. Each Drug Specific Dispensing Algorithm 15 is specifically developed to control the dispensing of a specific medication.

Figure 7A:
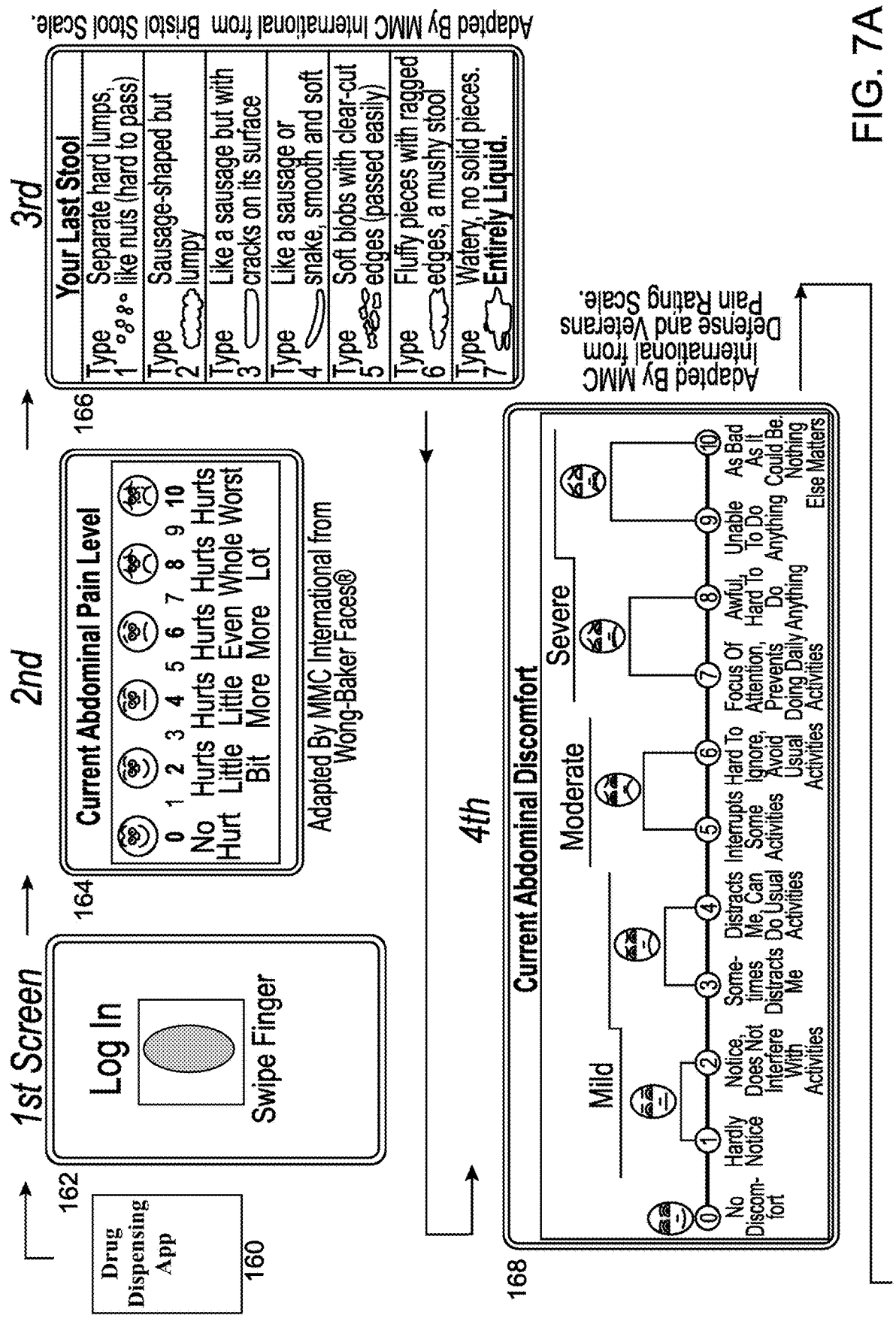
FIG. 7 is an exemplary embodiment of a flow chart of a standard prescription log in, Patient Self-Assessment and drug dispensing control.
Figure 7B:
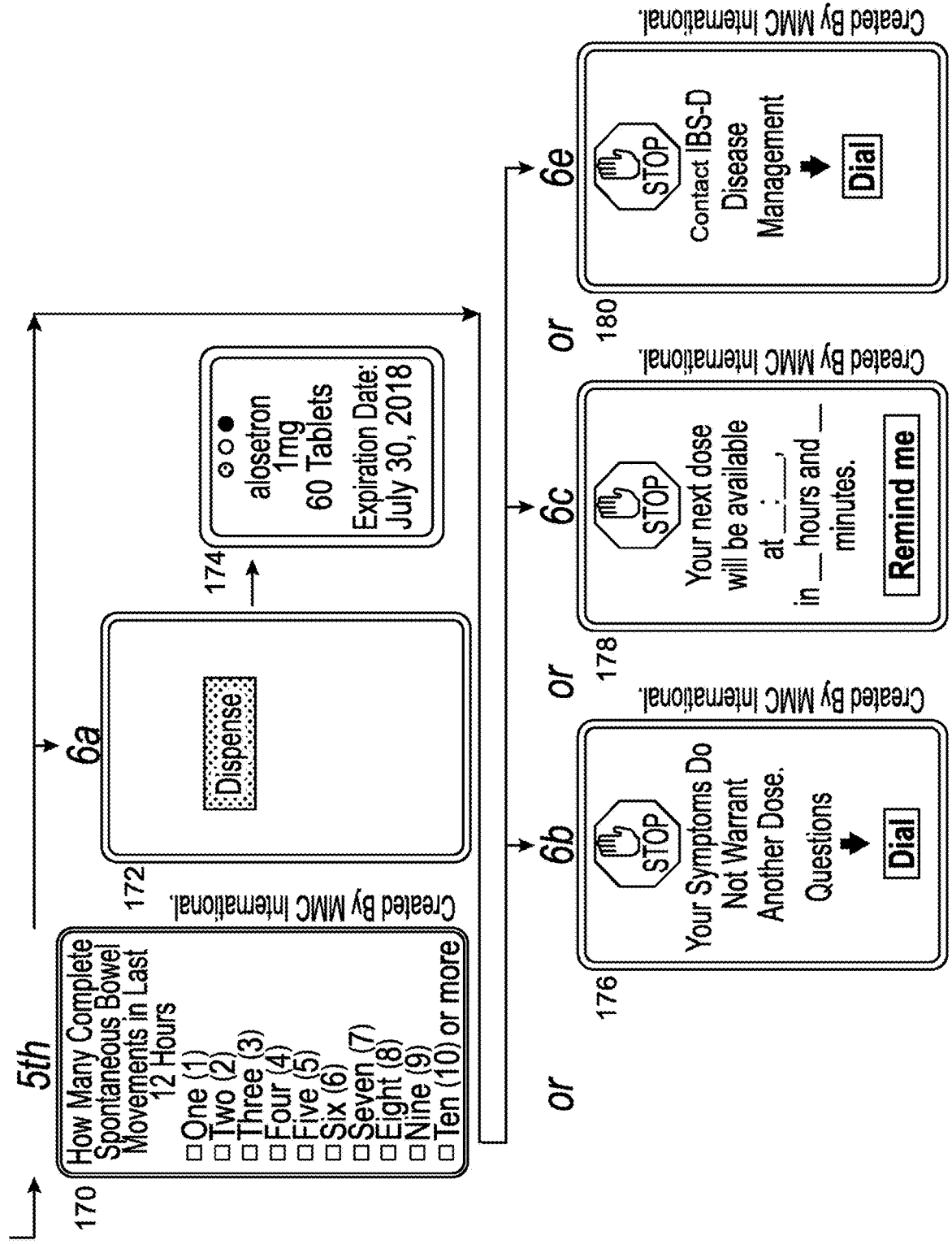

FIG. 7 presents the exemplary embodiment illustration of the Patient 50 interaction to dispense, as example, alosetron, a 5HT3 antagonist for the treatment of diarrhea predominant irritable bowel syndrome (IBS-D). The process begins by the Drug Dispensing App 160 alerting the Patient 50 that it is time to take his/her medication. If it is on a smart phone, it also changes the screen to the Drug Dispenser App 160 graphic' and when the Patient 50 unlocks the phone, the screen automatically changes to the Biometric Authentication screen 162. Alternatively, the Patient 50 can click on the Drug Dispensing App 160 for alosetron, this is automatically followed by a Biometric Authentication screen 162, upon authentication, the screen automatically moves to the Patient Self-Assessment screens 164, 166, 168, 170. A click on a value of the self-assessment screen automatically moves the process to the next screen. If nothing is found to block dispensing by the alosetron Drug Specific Dispensing Algorithm 15, then the Patient 15 sees the Dispense screen 172. By clicking on Dispense, the patient is then able to go to the related Drug Dispenser 30 and click, for example, on top of the dispenser to dispense a single dose—after which the Drug Dispenser goes back to a locked position. If the Patient 50 wants to change a prior entry before dispensing, he/she can use the devices scroll back capabilities to return to the right screen and change the selection. If the alosetron Drug Specific Dispensing Algorithm 15 finds any reason not to allow dispensing, it selects from the appropriate drug specific screen to show why dispensing was rejected and to facilitate the Patient's ability to avail himself/herself of the proper medication support 176, 178, 180.

Figure 8A:
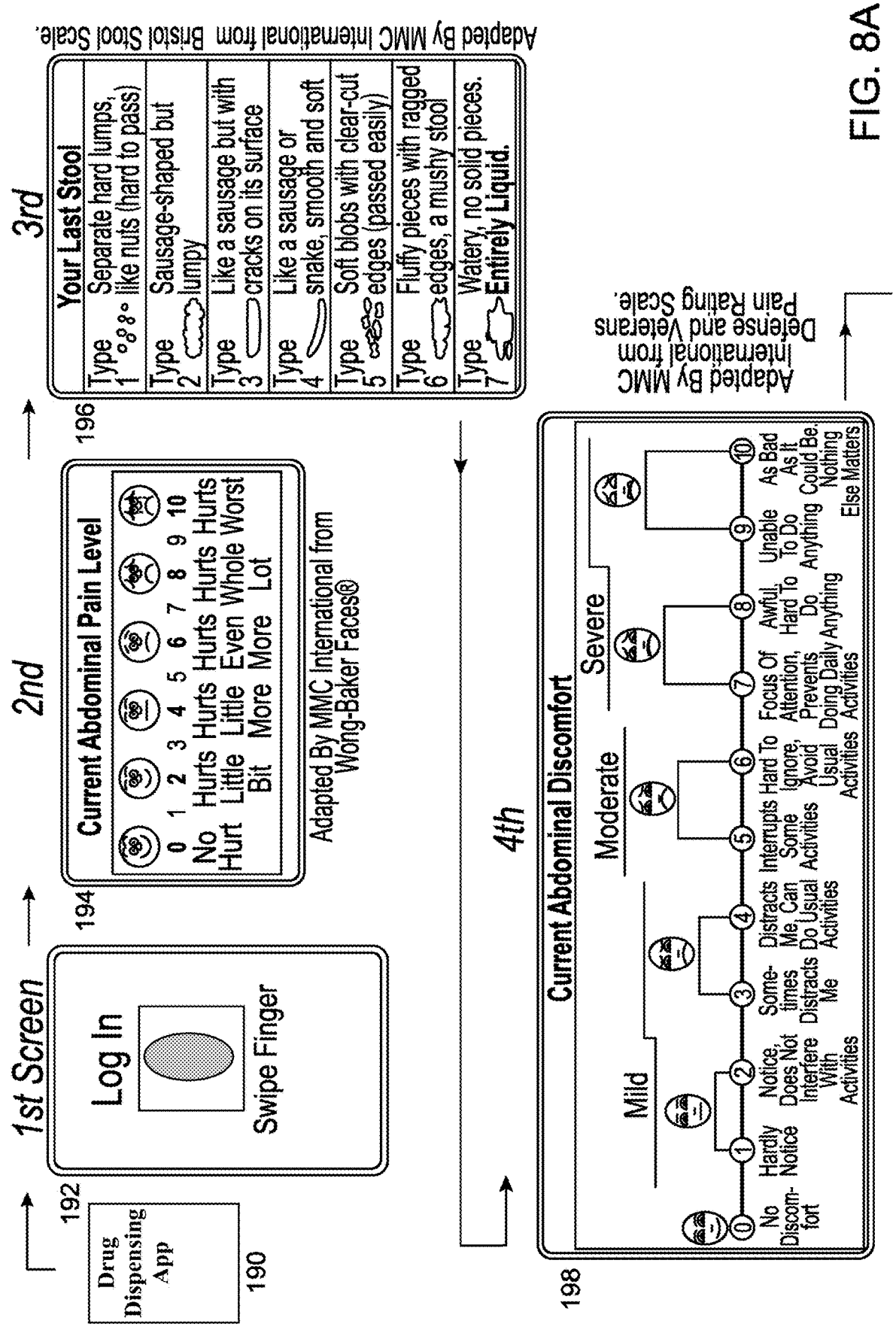
FIG. 8 is an exemplary embodiment of the flow chart of the respective screens utilized to capture clinical trial data and to control the drug dispensing.
Figure 8C:
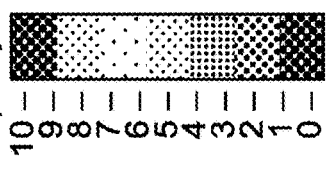
Figure 8D:
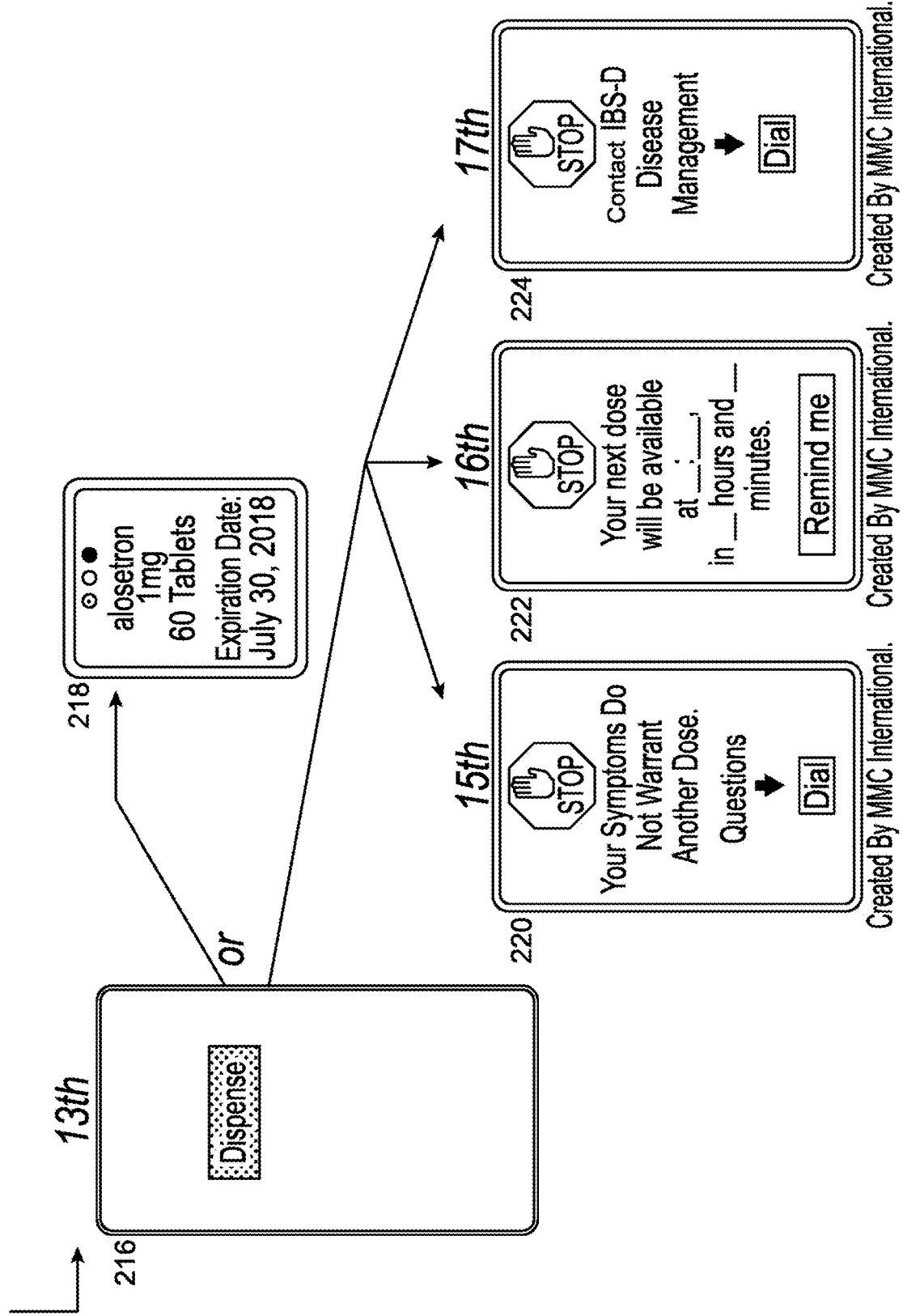

FIG. 8 is an exemplary embodiment of the alosetron Drug Specific App configured to capture all the Patient Self-Assessment information which is required by the FDA or EMA for the approval of a 5HT3 drug. The only difference to FIG. 7 are the additional input screens 200, 202, 204, 208, 210, 212, 214 required by the regulatory agencies. The same Drug Specific Dispensing Algorithm 15, decision tree, would be used for the clinical trial configuration as for the alosetron example in FIG. 7.

The embodiment is applicable for, as an example, clinical trials, post-launch surveillance, for the FDA's Risk Evaluation and Mitigation Strategy (REMS) programs, and to control and ensure drugs are efficacious and safe as dispensed within the Drug Specific Dispensing Algorithm 15 as part of a prescribed drug regimen, etc.

Figure 9:
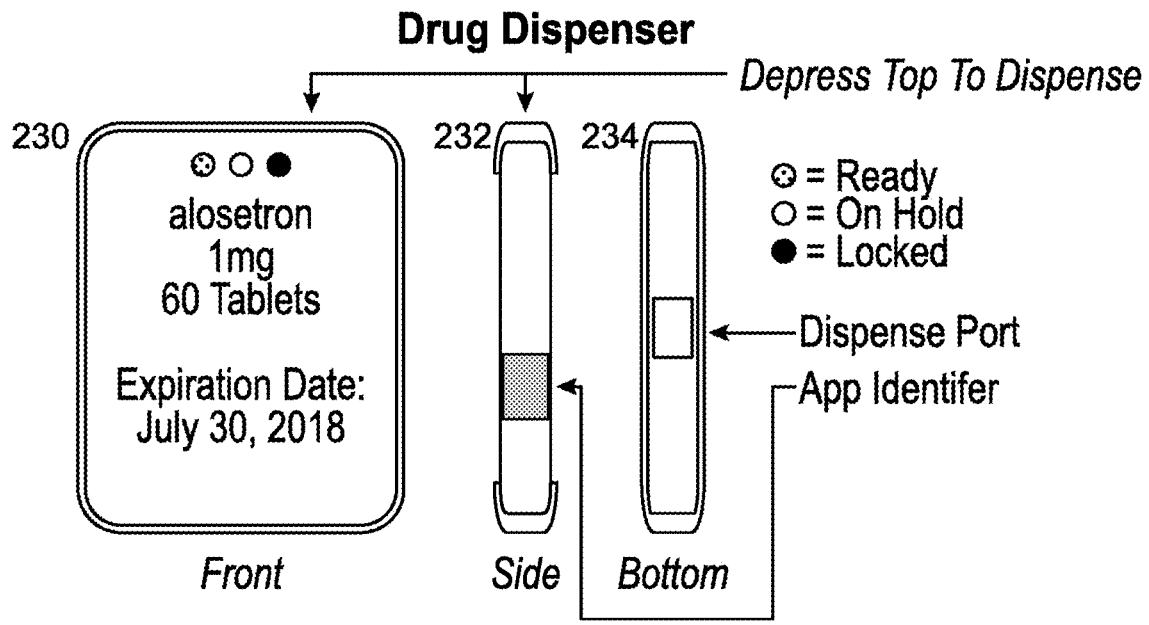
FIG. 9 is an exemplary embodiment of a Drug Dispenser.

FIG. 9 is an exemplary embodiment illustration of the Drug Dispenser 230, 232, 234 designed to be: (i) controlled by a Drug Specific App 10 resident on an Interface Device 20, (ii) water proof, (iii) tamper resistant, (iv) withstand being dropped and/or banged, to be rugged, (v) operate and withstand hot and cold temperatures within defined temperature ranges, (vi) reusable, (vii) rechargeable, and (viii) small enough to be carried in a pants pocket or purse. The Drug Dispenser 230 automatically recognizes the drug based upon the Drug Specific Drug Cassette 240 docked into the device. The Drug Specific Drug Cassette 240 can only be docked or removed by a healthcare professional. The Drug Dispenser 230 remains locked from dispensing unless it receives an encrypted signal from the authorized Drug Specific App 10. The Drug Dispenser 230 dispenses the drug with one click.

The Drug Dispenser 230 when interfaced through a digital handshake with the drug specific App transmits for example: (i) its serial number, (ii) the drug information on the Drug Specific Drug Cassette 240, (iii) current and historic temperatures since the last dispense, (iv) humidity exposure since the last dispense, and (iv) the date and time the drug was last dispensed.

Figure 10:
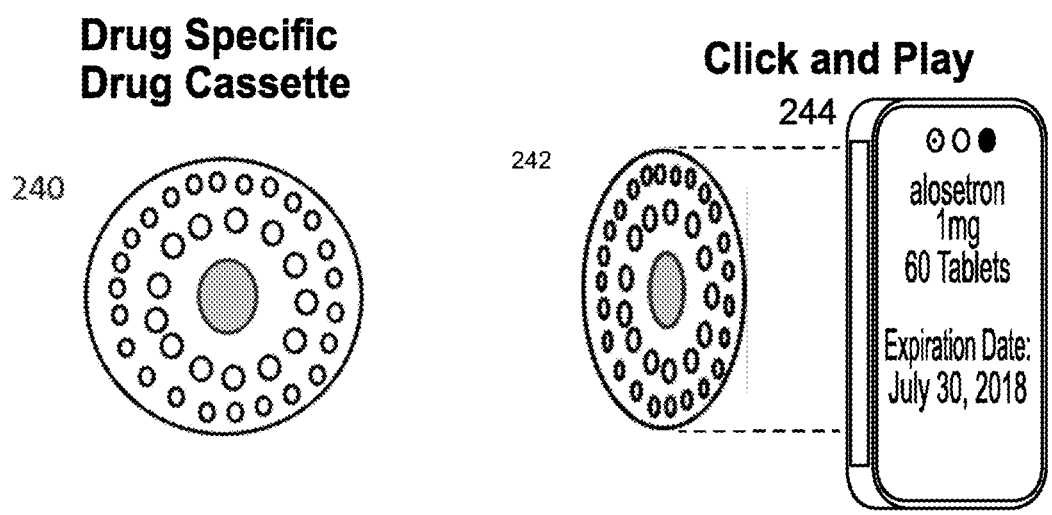
FIG. 10 is an exemplary embodiment of a Drug Cassette.

FIG. 10 is an exemplary embodiment illustration of the Drug Specific Drug Cassette 240 designed: (i) to use approved drug packaging materials, (ii) to dock into the Drug Dispenser 242, 244, and (iii) as a blank cartridge which can accommodate a number of different pills, caplets, capsules, etc. within a specified size range. The blank Drug Specific Drug Cassette 240 is designed to be proprietary to the Drug Dispenser 230 and is marked, as part of the automated cassette fill operation, to allow the Drug Dispenser 230 to ascertain the: (i) name of the drug (brand and/or generic), (ii) drug's NDC number, (iii) drug batch number, (iv) drug's expiration date, etc. The cassette closure is designed to allow printing or any required regulatory information.

FIG. 11 presents exemplary embodiment of the Patient 50 specific charts 250, 252, 254 which illustrate the relationship between when the Patient 50 took their medication versus his/her self-assessment or digitally captured symptoms and/or diagnostic values. This clearly shows the relationship between the medication and symptoms. The charts or tables, which can be requested and viewed by the Patient 50 on the Interface Device 20 are designed to educate the patient and promote Patient 50 prescription compliance and persistence.

Prescribers 60 can utilize the information to ensure the medication is efficacious for the individual Patient 50, to titrate dosing, and to personalize drug therapy (for personalized medicine).

The respective charts, graphs, reports, etc. may be generated by the Drug Specific App 10 and/or by the Integrated Support Centers 40 centralized analytics platform.

Figure 12:
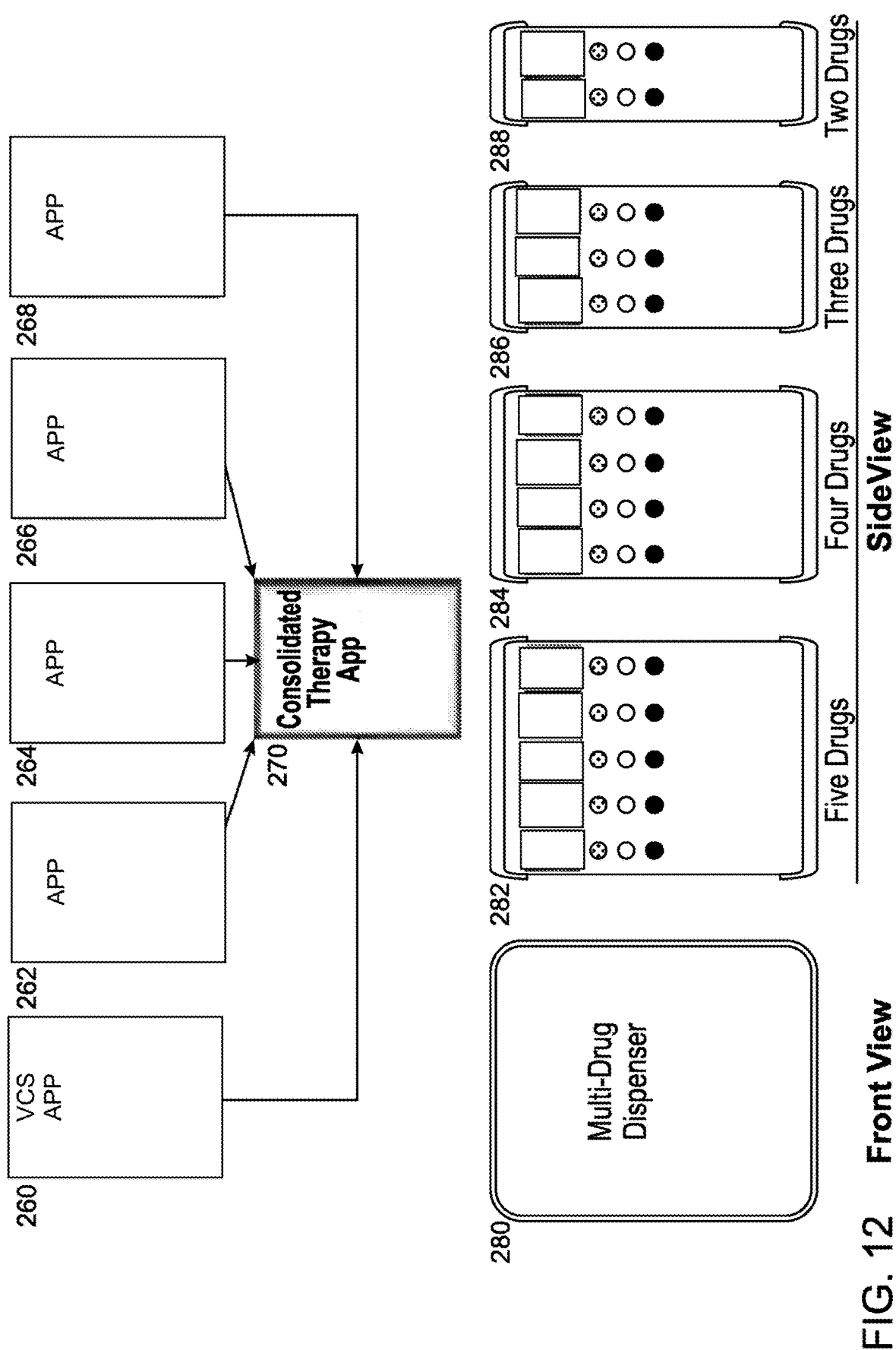
FIG. 12 is an exemplary embodiment of the Consolidated Therapy App and various Multi-Drug Dispensing devices.

FIG. 12 is an exemplary embodiment illustration of Drug Dispensers designed to serve the needs of most Patients 50. Approximately half of all Patients 50 take two medications and 20 percent take five or more. Consolidated Therapy App 270 automatically senses other Drug Specific Apps 10 that or on the Interface Device 20. It consolidates from two to many Drug Specific Apps 10 into a single user interface for all drugs—eliminating duplicate logins, entries, and record keeping. It in turn digitally handshakes with the Multi-Drug Dispenser 280 and uses the individual Drug Specific Dispensing Algorithms to control dispensing of each individual medication. Furthermore, it coordinates the dispensing schedules to have as few dispensing times, within the respective prescriptions, as possible. Multi-Drug Dispenser eliminates concerns about which drugs have to be taken when.

Illustrations 282, 284, 286, and 288 are exemplary of dispensing units containing from two drugs to five drugs. These units are standalone or can be docked into a Multi-Dispenser desktop unit.

Figure 13:
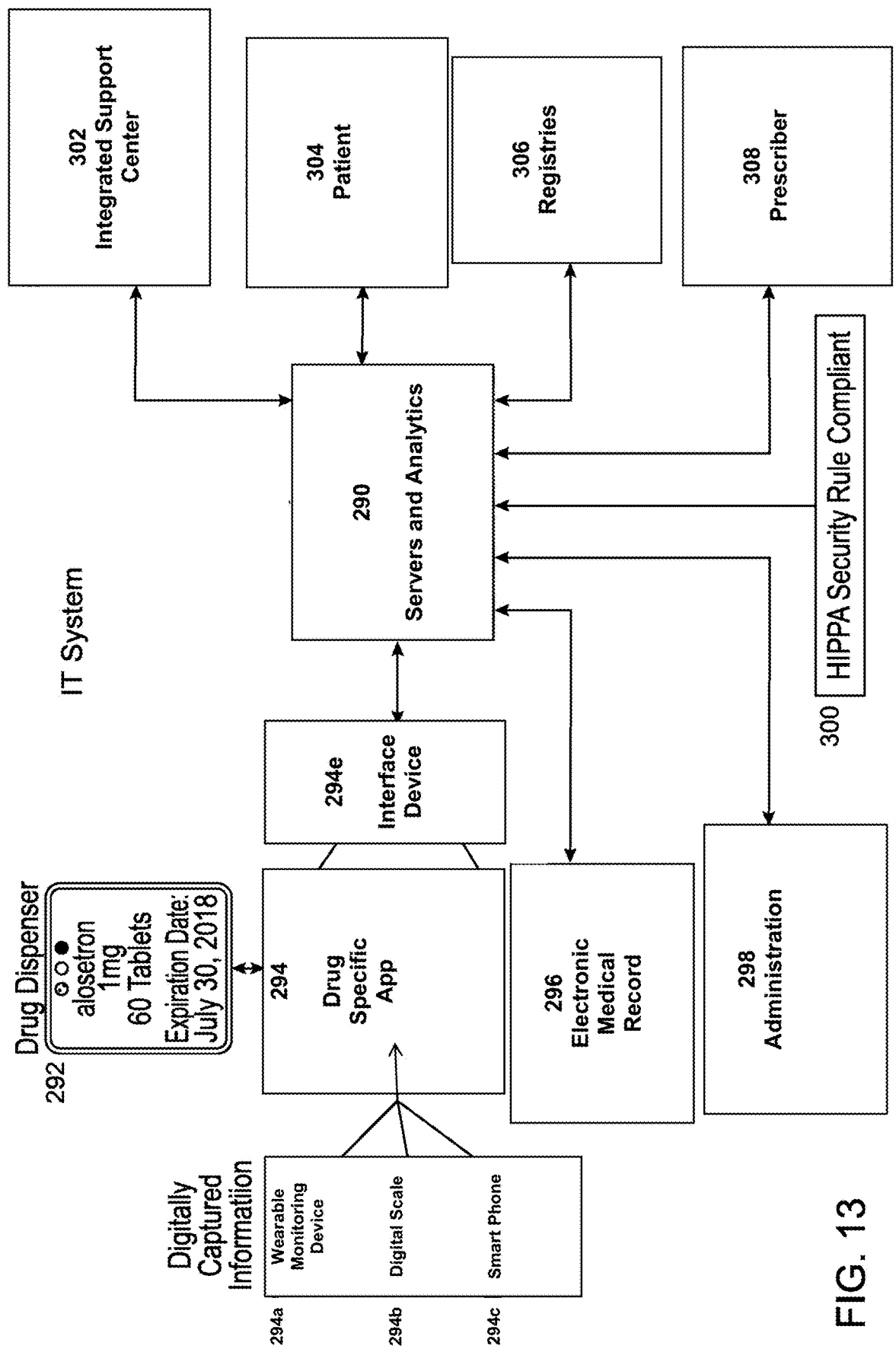
FIG. 13 is an exemplary embodiment of the Centralized IT System.

FIG. 13 is an exemplary embodiment of the Drug Dispenser 292 and the Drug Specific App 294 interfaces with the: (i) centralized Servers, (ii) databases, and (iii) Analytics systems (the IT System 290), through the Interface Device 294e, to ensure the Patient 304 is receiving the best care, tailored to the Patient ("personalized medicine"), for the prescribed Drug.

All the data collected by the Drug Specific App 294, from the Drug Dispenser 292, Digitally Captured Information 294a, 294b, 294c, the Patient Self-Assessment screens 100, 102, 104 contained within the Drug Specific App 294, and the respective output of the Drug Specific Dispensing Algorithm 15 are transmitted by the Drug Specific App 294 through the Interface Device 294e to the appropriate Patient database on the centralized Servers 290. The data is utilized to update the respective patient screens used by the Disease Management Counselors in the Integrated Support Center. The data is also made available to the respective Drug Registries 306 and the related Electronic Medical Record 296. Any information that requires a communication with the Patient 304 and/or the Prescriber 308 is handled either automatically by the patient management software or by the Integrated Support Center 302.

The patient's information is continually analyzed by the analytical routines both individually for the patient as well as in comparison with treatment data from other like patients to ascertain if any changes in therapy may be warranted. This analytical capability is utilized by the Integrated Support Center 302 to assist Prescribers 308 when they are trying to develop a treatment plan for difficult patients. The Analytics 290 performed may include the patient's data, pooled patient information, as well as information from Electronic Medical Records 296, clinical studies, and publications, etc.

As further example of the embodiment, the centralized Servers and Analytics 290 provide the following, as well as other, exemplary backbone support:

For the Drug Specific App 294: (i) assigns the App to a specific Patient 304, (ii) links the Drug Dispenser 292 to the Drug Specific App 294 which in turn limits the dispenser and App only to work with one another, (iii) stores the App codes on server, and (iv) enables and updates the Drug Specific App software via communication with the Interface Device 294e, etc.

For the Drug Dispenser 292: (i) stores all reported data in the designated databases on the Servers 290, (ii) syncs the patient data on all the respective Interface Devices 294e; (iii) stores dispensing, dispensing attempts, lock, and malfunction data; (iv) transmits reports to patient via the Drug Specific App 294 on request; (v) enables lock or unlock transmission from the Integrated Support Center 302; changes the Drug prescription on the Drug Specific App 294 as imputed by the Disease Management Represented per the Prescribers 308 instructions, and (vi) stores the authorized medical professional identification code required for the professional to open the Drug Dispenser 292 in order to change or load the Drug Specific Drug Cassette 242, etc.

For the Integrated Support Center 302: (i) aggregate patient data, (ii) presents and updates data on patient specific Managed Care call center screens, (iii) provides the ability to change a Patient's 304 prescription, (iv) enables the remote locking and unlocking of individual Drug Dispensers 292 via their Drug Specific App, (v) enable drug specific transmissions to all Patients 304, (vi) enables simultaneously locking all Drug Dispenser 292 for a specific Drug in the event of a Drug recall, and enables medical professionals to open, load, and close the Drug Dispenser 292, etc.

For the Patient 304: (i) prepares patient specific communications, (ii) creates personalized charts and reports, and (iii) generates "Payer Outcomes Reports", etc.

For Registries 306: (i) maintains the Registry 306, Electronic Medical Record 296 and App databases and analytics. (ii) prepares Therapy efficacy reports, (iii) prepares best practices reports, and (iv) through the Integrated Support Center provides Patient 304 specific diagnosis and therapy assistance to Prescribers 308 as requested.

For the Prescriber 308: (i) prepares and sends Patient 304 alerts, (ii) conducts meta-data analysis, prepares Patient specific reports and shares the results with the Prescriber 308, (iii) provides the Prescriber 308, through the Integrated Support Center 302, assistance/guidance based upon Prescriber 308 requested database and analytics queries, and (iv) prepares best practices reports based upon patient and Electronic Medical Records 296 meta-data analysis, etc.

For Electronic Medical Records 296: (i) interfaces with the Electronic Medical Record 296, (ii) updates Patient 304 dispensing, compliance, and persistence information, (iii) updates any Integrated Support Center counseling notes, and (iv) extracts patient data, within HIPAA guidelines, for meta-data analysis, etc.

Figure 14:
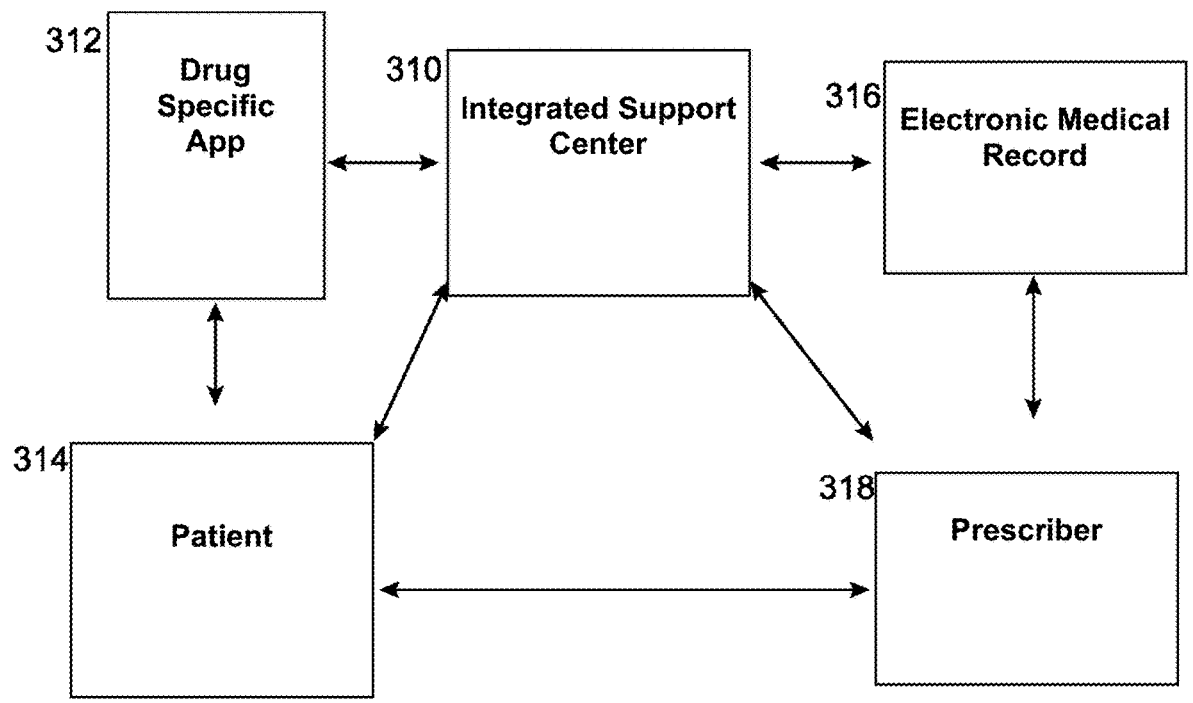
FIG. 14 is an exemplary embodiment of an Integrated Support Center.

FIG. 14 is an exemplary embodiment illustration of how the Integrated Support Center 310 interfaces with the Drug Specific App 312, the Patient 314, the Prescriber 318, and the Electronic Medical Record 316.

The Integrated Support Center's 310 interactions with the Patient 314 can be instigated by a number of different scenarios and take on many different forms. Examples include but are not limited to: (i) receipt of a patient alert from the Patient's Drug Specific Drug App 312; (ii) Patient 314 calls; (iii) answering Patient 314 questions about the device, App, the drug, or their therapy; (iv) Patient 314 counseling within the support center's guidelines; (v) locking the individual patient's Drug Dispenser 30 based upon: (a) an Drug Specific App alert, (b) an Integrated Support Center Analytics alert, (c) a patient conversation, etc.; (vi) unlocking the individual patient's Drug Dispenser 30 based upon: (a) a conversation with the Patient 314, (b) a conversation with the Prescriber 318, etc.

In addition, as an example, the Integrated Support Center 310 provides: (i) "Compliance" and "Adherence" support; (ii) outbound patient telephone calls; (iii) patient monitoring; (iv) emails and/or calls the patient's physician to recommend therapy change, etc.; (v) patient disease management education; (vi) ensures patient has access to their drug; (vii) as required, works with payers to obtain coverage for high cost medications; (viii) looks for prescription financial assistance programs; (ix) patient education and reeducation; (x) patient follow-up, and (xi) Medical Affairs support.

The Integrated Support Center's 310 interactions with the Prescriber 318 can be instigated by a number of different scenarios and take on many different forms. Examples include but are not limited to: (i) locking or unlocking a specific patient's Drug Dispenser 30; (ii) changing the prescription; (iii) patient specific physician support using the Integrated Support Center's 310 Analytics 290 to ascertain patient specific treatment alternatives; (iv) assist with patient specific data analysis; (v) provide disease/condition specific information; and (vi) Medical Affairs support, etc.

Figure 15:
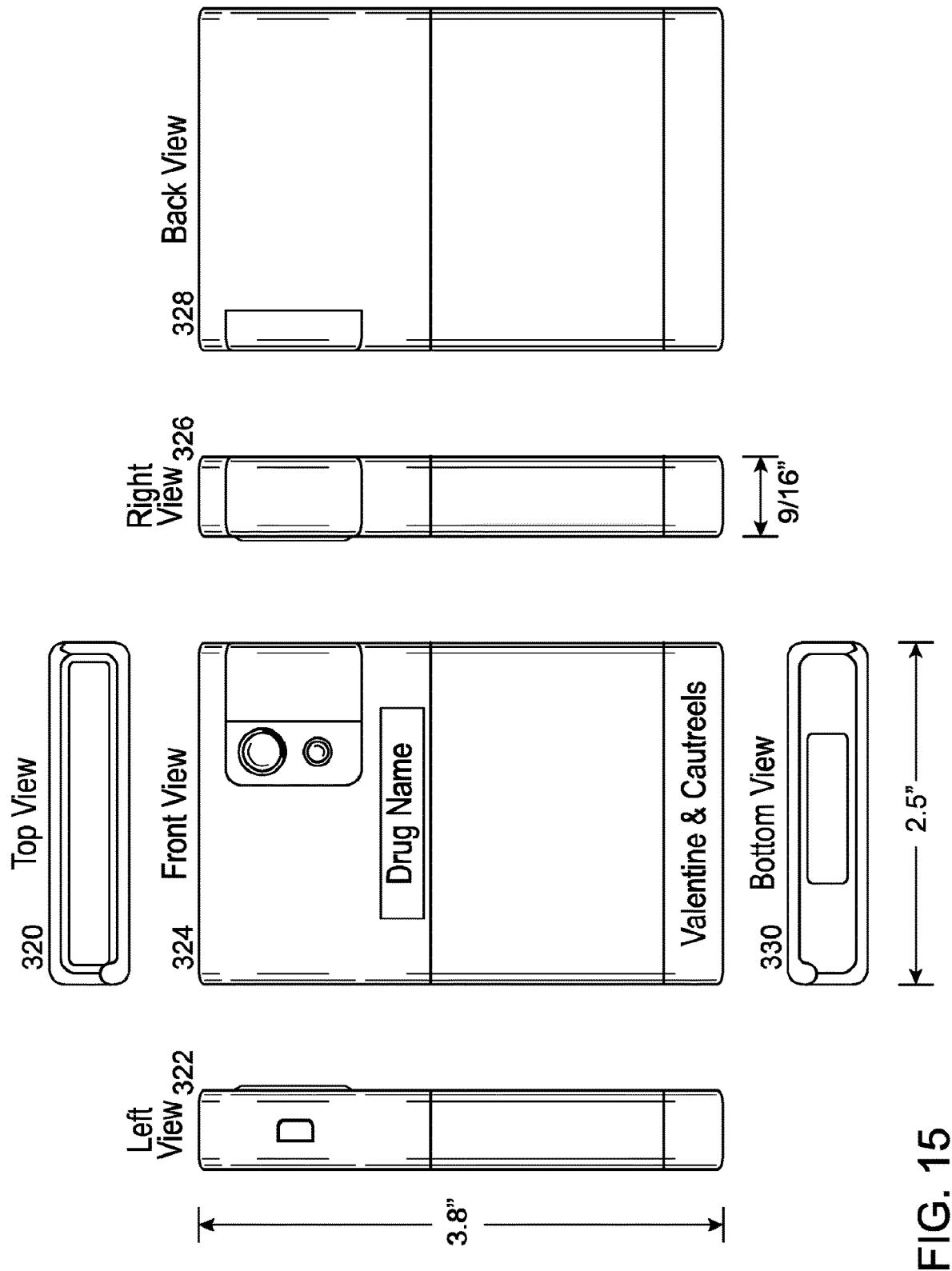
FIG. 15 is an exemplary embodiment of the design for a single drug Drug Dispenser.

FIG. 15 illustrates an exemplary embodiment of the design of a single drug Drug Dispenser 324. The size of said dispenser 324 in the exemplary being 3.8 inches tall by 2.5 inches wide by 9/16$^{th}$ inches wide. The design incorporates a clam shell design 320, 330 with a pivot on one corner and a tamper resistant and waterproof seal on the opposite edge right before the corner. All design work meets the respective FDA 21 CFR 820 Quality System Regulation, design center ISO 13485:2003 certification and Risk Management process for design, ISO14971, requirements. The Drug Dispenser 320, 322, 324, 326, 328, 330 has been designed for manufacturing (on both PCB and plastics or sheet metal parts), assembly (PCBA and Box Build), and cost. The design incorporates failure modes and effects analysis (FMEA) to address all possible failures in design, manufacturing, assembly, interface with the Drug Specific App 10 or when used by a patient. It is designed for testing, continual design improvement, the environment, and reliability.

Figure 16:
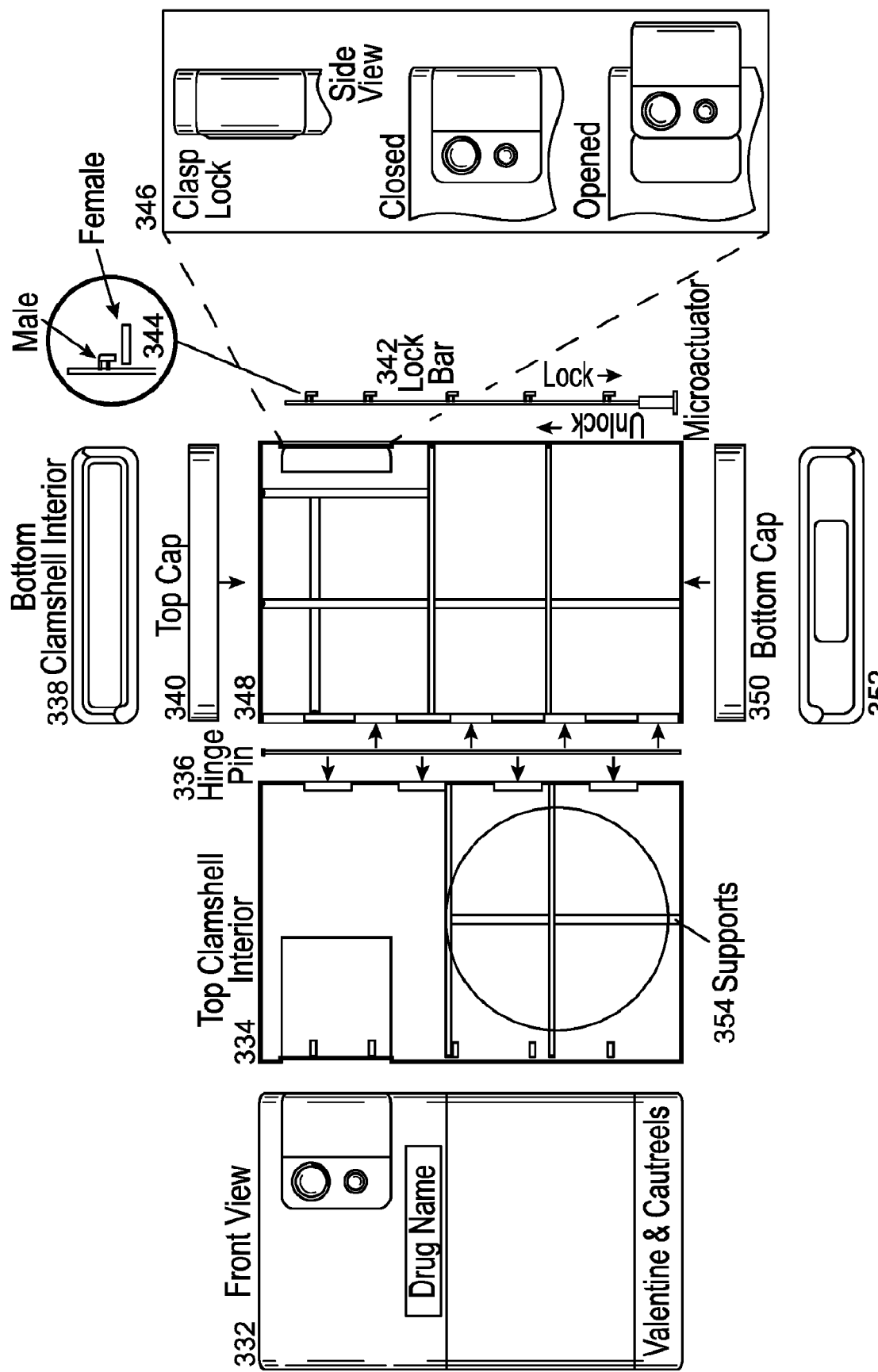
FIG. 16 is an exemplary embodiment of how the Drug Dispenser's clam shell design is assembled for secure closing and opening.

FIG. 16 is an exemplary embodiment illustration of the assembly and locking mechanism for the Drug Dispenser's 332 clamshell design. The interior of the top of the clamshell 334 incorporates hinges that marry with the hinges on the inside of the bottom clamshell interior 338. These are locked together with a hinge pin 336 that is treaded through the holes in the respective hinges, much the same as the hinges are held together on most common entry doors.

The top 334 and bottom 348 clamshells are locked closed and together by use of a microactuator moved locking bar 342. When the top of the clamshell is closed with the bottom clamshell, the locking bar is pulled down by the microactuator and the hook's male member docks into the female orifice on the locking buttons 344.

The design incorporates integrated supports 354 to ensure the integrity and durability of the design. They are also instrumental in adding strength, as required, for adding anchors for the respective Drug Dispenser 332 components.

The design eliminates the ability to open the Drug Dispenser without an authorized signal to cause the microactuator to unlock 342. The Top Cap 340 is fitted to close the top of the Bottom Clamshell. The top of the Top Cap 340 covers the top of the Hinge Pin 336 and holds it in place. The Bottom Cap 350 covers the bottom of the Hinge Pin 336 and holds it in place.

The right interior to the Top Cap provides for a dock for the end of the Lock Bar 342 and allows it to move up and down, to lock or unlock, as required. The Bottom Cap 350 provides the seat that supports the Microacturator 342 that lock and unlocks the clamshell by moving the Lock Bar 342 up and down.

The Top 340 and Bottom 350 Caps are secured to the Bottom Clamshell Interior 348 by screws that securely marry each of the pieces together. The unit then forms a ridged platform for the Top Clamshell Interior 334 to dock with. When the Drug Dispenser 332 is closed, it forms a sturdy, tamper resistant housing for the Drug Specific Drug Cassette 240.

In order to provide the requisite downward pressure to ensure the unit is both water and dust resistant and to contribute to its rugged design, the Drug Dispenser 332 has a Clasp Lock 346 designed to exert the desired level of pressure on the closing joints to secure design integrity.

In this embodiment, the Top Cap 338 incorporate the one click dispensing button. The Bottom Cap 352 houses the dispensing port.

Figure 17:
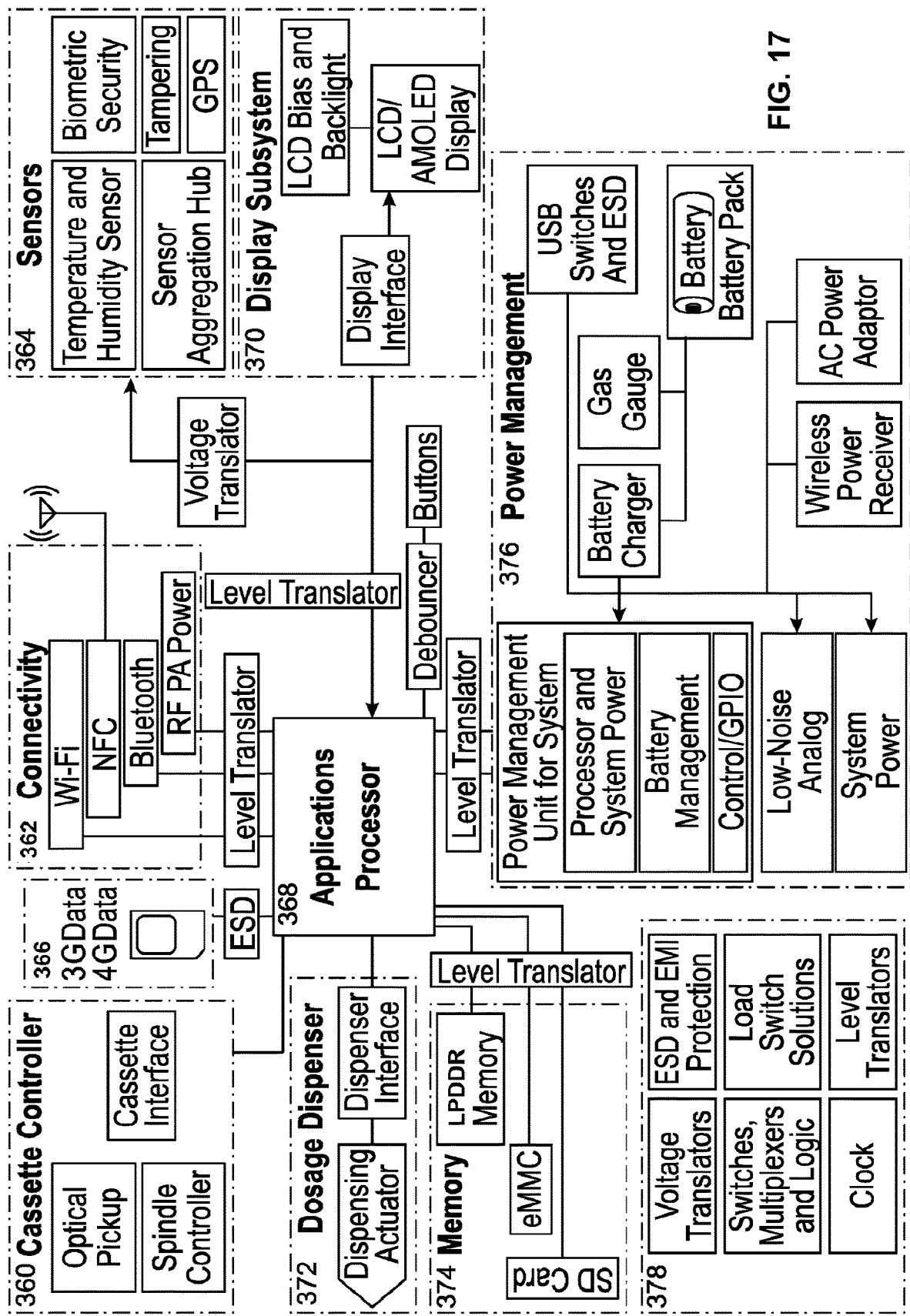
FIG. 17 is an exemplary embodiment of the electronic schematic for the Drug Dispenser.

FIG. 17 is an exemplary embodiment of the Drug Dispenser's 324 electronics and features schematic. The Drug Dispenser's 324 system is comprised of an Applications Processor 368 that contains the units Firmware, individual Drug Dispenser 324 serial number, and manages all functions. The main unit components are the: (i) communications connectivity 362 module, (ii) its data transfer capability 366, (iii) the units sensors and/or applications 364 that allow the unit to authenticate the user, sense efforts to tamper/open the unit without authority, measure drug storage temperature and humidity, to time stamp an action or event (clock function), and locate the unit via GPS; (iv) the display module 370; (v) the Power Management and recharge system 376; (vi) Memory management 374; (vii) Cassette Controller which rotates the Drug Specific Drug Cassette 240 which enables dispensing as well as the unit to read specific drug cassette information; (viii) the Dosage Dispenser system 372; and (ix) the various components designed to facilitate and protect the different system functions.

Figure 18:
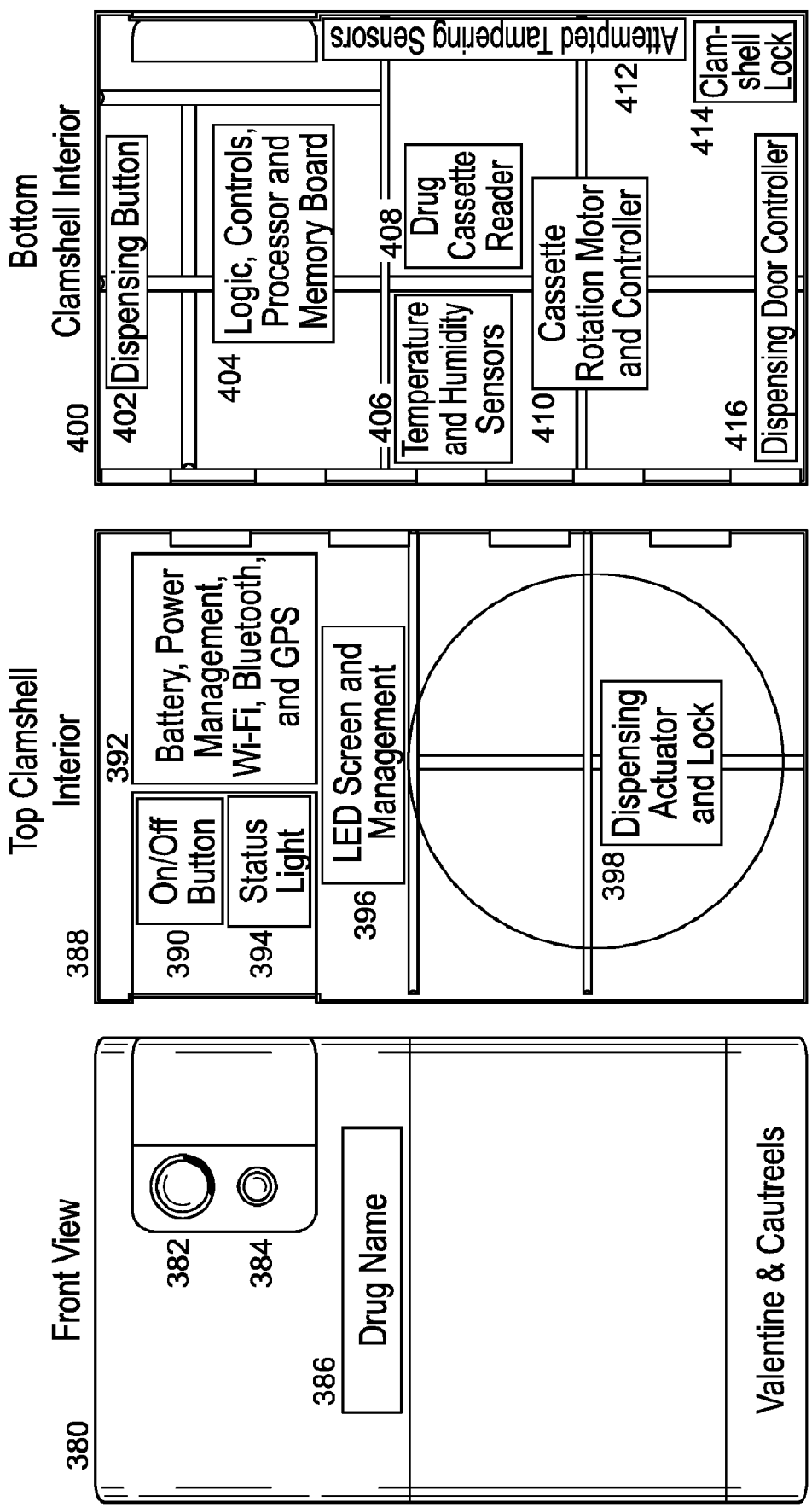
FIG. 18 is an exemplary embodiment of the placement of electronics and mechanical components on the outside and within the Drug Dispenser.

FIG. 18 is an exemplary embodiment of the placement of electronics and mechanical components on the outside and within the Drug Dispenser. The front of the Drug Dispenser 380 contains an On Off Button 382 which the user can depress if the Drug Dispenser 380 does not automatically come on when the Drug Specific App 10 handshakes with the Drug Dispenser 380. When a handshake is effectuated or the On Off Button 382 are pushed, a blue led light comes on 384. The light 384 turns to green if the unit is ready to dispense, yellow 384 if it is awaiting authority to dispense, and red 384 if the unit is locked and will not dispense. The display on 386 resides on the center of the face, Front View, of the Drug Dispenser 380.

A number of components fit on the Top Clamshell Interior 388; these include: (i) the On Off Button 382 switch 390, (ii) the LED status light 384 LED and electronics 394; (iii) the battery, power management, Wi-Fi, Bluetooth, GPS and antenna systems 392; (iv) the LED Screen 386 electronics and management system 396; and (v) the drug dispensing actuator arm and dispensing lock 398. The Bottom Clamshell Interior 400 houses the: (vi) single click Dispensing Button 402; (vii) the Logic, Controls, Processor and Memory Board and its various components 404; (viii) Temperature and Humidity sensors 406; (iv) the Attempting Tampering Sensors 412; (x) the Cassette Rotation Motor and Controller (works like a CD-Rom rotator) 410; (xi) the Drug Cassette Reader 408; (xii) the Clamshell Lock microactuator controller 414, and (xiii) the Dispensing Door Controller 416.

IV. Examples

The embodiment of the invention can be utilized, for among other uses, 1) to improve the drug's safety profile by ensuring proper, personalized drug utilization (e.g., Dispensing), 2) as a diagnostic aid/tool, 3) to preclude drug related adverse events, 4) to decrease the chance of addiction, 5) to preclude overdosing, 6) to manage drug dependence withdrawal, 7) to manage oral patient controlled analgesia, 7) to preclude drug divergence, 8) to guard the medication against accidental ingestion by a child, and 9) to capture the information required and control drug dispensing during clinical trials.

A. Dispensing

Ensuring the proper utilization of antihypertensive medications serves as an example of how the embodiment can be used to ensure proper drug utilization. As patients get older, they have a tendency to gain weight and to develop comorbidities. These factors can interfere with how the medication is metabolized and alter the need or effectiveness of the drug over time. As a result, certain patients may become dizzy or faint as a result of a hypotensive event. If the patient is prescribed an antihypertensive, it is beneficial to prevent a potential hypotensive event, especially as it may lead to an untoward accident.

Under the current embodiment, the patient would be prescribed an antihypertensive dispensed using the Drug Specific App 10 controlled Drug Dispenser 30. When the Patient 50 clicks on the Drug Specific App 10 to take his/her next dose, the Drug Specific Dispensing Algorithm 15 would automatically check to ensure the drug has not expired, and if it has not, then to see if it has been stored correctly, and if the Drug has been stored correctly, then, for example, it would handshake with designated devices to digitally capture blood pressure and heart rate information. Thereafter, it asks the Patient 50 at least one Patient Self-Assessment question. Examples include but are not limited to: (i) have you gotten dizzy since the last time you took your antihypertensive medication, (ii) do you have blurry vision, (iii) have you felt like fainting since you took your last antihypertensive, etc. If the patient answered yes to any of the Patient Self-Assessment questions, the Drug Specific Dispensing Algorithm 15 would check the trending of the Patient's 50 blood pressure and heart rate information since the last dose. If the indication would be that the Patient 50 may suffer a hypotensive event as defined by the Decision Tree, the Drug Specific Dispensing Algorithm 15 would lock the Drug Dispenser 30 and inform the Patient 50 that he/she should call the Integrated Support Center 40 or talk with their Prescriber 60 or a physician prior to being able to dispense the next dose, even if the dose is within prescribing parameters. After talking with the Patient 50, the Disease Management representative at the Integrated Support Center 40 can decide within their operating constraints whether or not to unlock the Drug Dispenser 30 and allow the Patient 50 to dispense and take the prescribe antihypertensive. If not appropriate, the representative would send an email, text, and/or call the Prescriber 60 to advise him/her that an adjustment has to be made to the Patient's 50 hypertension treatment. The Drug Dispenser 30 can then be unlocked and allowed to dispense the medication if those are the Prescriber's 60 instructions or the prescription can be changed based upon the Prescriber's 60 instructions.

In the process, an accident and/or costlier intervention can be averted, the drug efficacy for the specific Patient 50 is assured, the patient's quality of care is personalized and improved, and the patient's quality of life is enhanced.

B. Diagnostic

The embodiment of the Invention can also be utilized to assist in diagnosis. As an example, there are many different types of pain and different types of headaches. Patients will generally begin by self-medicating with over the counter (OTC) analgesics such as aspirin. As the pain or discomfort increases, patients increase the number of tablets taken (i.e., the dosage), as well as the frequency of self-medication. At a certain point, they go to their doctor seeking adequate relief.

When the doctor talks with the Patient 50, he/she may describe many different types of pain, making it difficult to diagnose. Pain has multiple causes, and people respond to it in multiple and individual ways. The pain that one person pushes their way through might be incapacitating to someone else.

Headaches represents an example. It is important to figure out what type of headache is causing the pain. If the doctor knows the type of headache, he/she can treat it correctly. However, as was highlighted by a 2004 study, 80% of people who had a recent history of self-described or doctor-diagnosed sinus headache, but no signs of sinus infection, actually met the criteria for migraine. The following discusses the different types of headaches:

1) Tension headaches, the most common type of headache, can generally be adequately treated with over-the-counter treatments such as aspirin, ibuprofen, or acetaminophen (Tylenol). Experts believe these may be caused by the contraction of neck and scalp muscles (including in response to stress), and possibly changes in brain chemicals.
2) Cluster headaches, which affect more men than women, are recurring headaches that occur in groups or cycles. They appear suddenly and are characterized by severe, debilitating pain on one side of the head, and are often accompanied by a watery eye and nasal congestion or a runny nose on the same side of the face. During an attack, people often feel restless and unable to get comfortable; they are unlikely to lie down, as someone with a migraine might. The cause of cluster headaches is unknown, but there may be a genetic component. There is no cure, but medication can cut the frequency and duration.
3) Sinus headaches occur when a sinus becomes inflamed, often due to an infection. They can generally be diagnosed by symptoms or the presence of pus viewed through a fiber-optic scope. Headaches due to sinus infection can be treated with antibiotics, as well as antihistamines or decongestants.
4) Rebound headaches, ironically, can be caused by the overuse of painkillers for headaches. Culprits include over-the-counter medications like aspirin, acetaminophen (Tylenol), or ibuprofen (Motrin, Advil), as well as prescription drugs.
5) Migraine headaches can run in families and are diagnosed using certain criteria: (i) at least five previous episodes of headaches, (ii) last between 4-72 hours, (iii) at least two out of four headaches have one-sided pain, throbbing pain, moderate-to-severe pain, and pain that interferes with, is worsened by, or prohibits routine activity, and (iv) at least one of the following is associated with the pain: nausea and/or vomiting, or, if those are not present, then sensitivity to light and sound. A migraine may be foreshadowed by aura, such as visual distortions or hand numbness. (About 15 percent to 20 percent of people with migraines experience these.)
6) Mixed headache syndrome, also called transformed migraines, is a combination of migraine and tension headaches.
7) Acute headaches are headaches that occur suddenly and have symptoms that subside after a relatively short period of time.
8) Hormone headaches are often associated with women's changing hormone levels during menstruation, pregnancy, and menopause. Chemically induced hormone changes, such as with birth control pills, also trigger headaches in some women.
9) Chronic progressive headaches also called traction or inflammatory headaches, are chronic progressive headaches that get worse and happen more often over time. These are the least common type of headache, accounting for less than five percent of all headaches in adults and less than two percent of all headaches in kids. Chronic progressive headaches may be the result of an illness or disorder of the brain or skull.

Diagnosis requires a headache evaluation that includes: (i) headache history, (ii) description of the headaches, (iii) headache symptoms, (iv) characteristics, (v) a list of things that cause the headache, (vi) aggravate the headache, and (vii) things the patient has done to relieve a headache. The patient is also requested to keep a headache diary.

The proper treatment will depend on several factors, including the type and frequency of the headache and its cause. There are many migraine and headache medications and other treatments are available. The appropriate treatment often depends on the type of headache.

Headache pain may need to be managed with medications. Headache drugs used to treat headache pain can be grouped into three different categories: symptomatic relief (drugs used to treat the headache pain or accompanying symptoms of migraines like nausea), abortive therapy (drugs used to stop a migraine headache), and preventive therapy (drugs used to prevent a migraine). Botox injections represents another migraine and headache treatment.

The way the body responds to migraine and headache medications may change over time, so medications may need to be adjusted.

The embodiment of the Invention enables the aggregation of Patient 50 specific dispensing information and Patient Self-Assessment information specifically developed to assist in the diagnosis and management of headaches.

C. Management of Complex Drug Therapy

Cystic fibrosis (CF) serves as an example of how the system can be utilized to manage complex drug therapy. There is no cure for CF, but treatment can ease symptoms and reduce complications, physician office visits and hospitalizations. Close monitoring and early, aggressive intervention is recommended.

Managing CF is complex, so treatment is best if managed by a center that specializes in cystic fibrosis. The goals of treatment include: (i) preventing and controlling lung infections, (ii) loosening and removing mucus from the lungs, (iii) preventing and treating intestinal blockage, (iv) providing adequate nutrition, and (v) medications.

The patient must take multiple drugs, the schedule and combination which must be personalized for each patient. The medicines include those to help treat or prevent lung infections, reduce swelling and open up the airways, and thin mucus. If the patient has mutations in a gene called G551D, which occurs in about 5 percent of people who have CF, the doctor may prescribe the oral medicine ivacaftor (approved for people with CF who are 6 years of age and older). Adherence and persistence with each drug regimen is critical to avoid costly complications. The options include:

a. antibiotics to treat and prevent lung infections (Most people with CF have ongoing, low-grade lung infections. Sometimes, these infections become so serious that the patient may need to be hospitalized. Antibiotics are the primary treatment.)

b. mucus-thinning drugs to help the patient cough up the mucus, which improves lung function.

c. bronchodilators to help keep the airways open by relaxing the muscles around the bronchial tubes, and d. oral pancreatic enzymes to help your digestive tract absorb nutrients.

The embodiment of the Invention enables the complex management of the CF Patient 50 via the utilization of the Multi-Drug Dispenser 280. The Consolidated Therapy App 270 consolidates from two to as many Drug Specific Apps 10 as are resident on the Interface Device 20 into a single user interface for all drugs—eliminating duplicate logins, entries, and record keeping. It in turn digitally handshakes with the Multi-Drug Dispenser 280 and uses the individual Drug Specific Dispensing Algorithms 15 to control dispensing of each individual medication. Furthermore, it coordinates the dispensing schedules to have as few dispensing times, within the respective prescriptions, as possible. Multi-Drug Dispenser 280 eliminates concerns about which drugs have to be taken when. It can also be programmed to provide alerts for the patient to take his/her related injectable and/or inhaled medications. In this way, the Dispensing System simplifies CF drug management, encourages prescription compliance and persistence, avoids complications, and thereby reduces the total cost of treating a CF patient by decreasing the number of physician interventions and hospitalizations.

D. Opioids

Opioid medications (examples include: codeine, fentanyl and analogs, hydrocodone, hydromorphone, methadone, oxycodone, Oxymorphone, etc.) are effective in controlling pain. However, physicians are reluctant to prescribe them due to their overdose, abuse, addiction and divergence potential and related REMS programs. Some patients are also reluctant to take them due to their addiction potential. The embodiment provides control and real time monitoring and thereby address each of these shortcomings.

Overdosing is addressed by the inability of the patient to dispense a dose more frequently than allowed by the prescription. This is handled by the Drug Specific Dispensing Algorithm 15 which controls dispensing by the Drug Dispenser 30.

Abuse is addressed by the design of the tamper resistant Drug Dispenser 230. The Drug Specific Drug Cassette 240 can only be docked with the Drug Dispenser 244 by an authorized medical professional. Any attempt by an unauthorized person to open the Drug Dispenser 244 triggers a signal to the Drug Specific App 10 which automatically locks the Drug Dispenser 244 and alerts the Integrated Support Center 40. The Integrated Support Center 40 then calls the Patient 50 to ascertain why they are trying to open the Drug Dispenser 30. At this point, the Integrated Support Center 40 works with the Patient 50 to address any dispensing related issues and unlocks the Drug Dispenser 30 or, if attempted abuse is suspected, contacts the Prescriber 60 to alert them of the conversation with the Patient 50 and asks the Prescriber 60 whether or not the Drug Dispenser 30 should remain locked or if it should be unlocked. If authorized, the Integrated Support Center 40 updates the Electronic Medical Record 70 related to the calls to the Patient 50 and the Prescriber 60.

The potential for addiction is mitigated by: (i) the patient's inability to dose more frequently than the prescribed medication schedule, (ii) by tracking attempted earlier than prescribed dosing events, (iii) by capturing any attempts to open the Drug Dispenser 30, and (iv) through the use of patient self-assessment 100, 102, 104 and/or digitally captured relevant information, trended over time, to ascertain the effectiveness of the drug on the specific patient. The centralized drug specific patient and population focused analytics programs 290 are designed to take a myriad of patient specific actions and inputs into account in order to identify potential movement of the Patient 50 toward addiction. When potential addiction is identified, the analytics software 290 is programmed to alert the Integrated Support Center 40 so they may alert the Prescriber 60 and update the patient's Electronic Medical Record 70.

Divergence is precluded by a number of combined features: (i) the serial number of the Drug Specific Drug Cassette 240 and the drug's batch number are digitally married to the Drug Dispenser 244, (ii) the serial number of the Drug Dispenser 230 is linked to the Patient's Drug Specific App 10, (iii) the use of the Drug Specific App is restricted to a specific Patient 50, and (iv) the Drug Specific App 10 requires a biometric login 90 to access the Drug Specific App 10 in order to instruct the Drug Dispenser 230 to dispense the drug. The unit further supplies additional control of the drug being taken can be tracked with RFID tracking which would allow the Drug Specific App 10 to track the drug until it is ingested by the patient. The time interval between the time the drug is dispensed and the time it is ingested, over time, provides an indication of compliance or abuse. When coupled with mega-data analytics conducted by the Integrated Support Center, the probability of accurately identifying potential abusers is significantly increased.

The system is designed to comply with the respective REMS program and to virtually eliminate required data capture and automate patient specific tracking and dispensing report preparation. The Integrated Support Center 40 will also support the Prescriber 60 by preparing the required REMS reports encompassing all his/her patients.

The system also allows for the redefinition of Prescription Drug Monitoring Programs by closing the loop between pharmacies and healthcare providers and the patient by controlling and tracking use on an individual patient basis.

Attributes of the system enable oral patient controlled analgesia. Studies have shown that patients that have the ability to self-medicate as warranted, e.g., PRN with set prescription parameters, tend to use less medication, further mitigating potential side effects.

The system may also be utilized to predict, for example, opioid related constipation and to alert the patient to take a laxative at the appropriate time. If the system's multi-drug dispenser is utilized, the program can dispense the laxative as well as the opioid and/or other medication as prescribed.

E. Addiction and Withdrawal

Addiction is a global crisis with an estimated 2.4 million opioid-dependent people in United States, 1.3 million in Europe and twenty million in the rest of the world. Opioid overdose is the second leading cause of accidental death in the US. Overdoses claimed 16,000 lives in the United States alone in 2012.

If other kinds of addiction are added, 4.5% of disease and injury around the globe can be attributed to alcohol, and these numbers are most likely underreported. The true population that suffers from opioid, prescription drug, and alcohol addiction is estimated to be much greater.

Addiction can either be treated with buprenorphine and/or naloxone (examples of brand names include Butrans, Suboxone, Zubsolv). In cases of physical dependent, withdrawal must be managed through the gradual decrease of doses of the dependent drug (e.g., barbiturates, benzodiazepines, methamphetamines, narcotics, opioids, methadone, etc.).

Appropriate precautions must be taken to minimize risk of misuse, abuse, or diversion, appropriate protection from theft, and unintended pediatric exposure; much the same as with the opioids. In addition, appropriate clinical monitoring as to the patient's level of stability is essential. The embodiment of the system provides control and real time monitoring and thereby address each of these shortcomings.

Overdosing is addressed by the inability of the patient to dispense a dose more frequently than allowed by the prescription. This is handled by the Drug Specific Dispensing Algorithm 15 which controls dispensing by the Drug Dispenser 30. The controls are in place even for the Drug Specific App 10 and Drug Dispenser 30 enabled oral PRN dosing regimen.

Abuse is addressed by the design of the tamper resistant Drug Dispenser 230. The Drug Specific Drug Cassette 240 can only be docked with the Drug Dispenser 244 by an authorized medical professional. Any attempt by an unauthorized person to open the Drug Dispenser 244 triggers a signal to the Drug Specific App 10 which automatically locks the Drug Dispenser 244 and alerts the Integrated Support Center 40. The Integrated Support Center 40 then calls the Patient 50 to ascertain why they are trying to open the Drug Dispenser 30. At this point, the Integrated Support Center 40 works with the Patient 50 to address any dispensing related issues and unlocks the Drug Dispenser 30 or, if attempted abuse is suspected, contacts the Prescriber 60 to alert them of the conversation with the Patient 50 and asks the Prescriber 60 whether or not the Drug Dispenser 30 should remain locked or if it should be unlocked. If authorized, the Integrated Support Center 40 updates the Electronic Medical Record 70 related to the calls to the Patient 50 and the Prescriber 60.

The potential for addiction is mitigated by: (i) the patient's inability to dose more frequently than the prescribed medication schedule, (ii) by tracking attempted earlier than prescribed dosing events, (iii) by capturing any attempts to open the Drug Dispenser 30, and (iv) through the use of patient self-assessment 100, 102, 104 and/or digitally captured relevant information, trended over time, to ascertain the effectiveness of the drug on the specific patient. The centralized drug specific patient and population focused analytics programs 290 are designed to take a myriad of patient specific actions and inputs into account in order to identify potential movement of the Patient 50 toward addiction. When potential addiction is identified, the analytics software 290 is programmed to alert the Integrated Support Center 40 so they may alert the Prescriber 60 and update the patient's Electronic Medical Record 70.

Divergence is precluded by a number of combined features: (i) the serial number of the Drug Specific Drug Cassette 240 and the drug's batch number are digitally married to the Drug Dispenser 244, (ii) the serial number of the Drug Dispenser 230 is linked to the Patient's Drug Specific App 10, (iii) the use of the Drug Specific App is restricted to a specific Patient 50, and (iv) the Drug Specific App 10 requires a biometric login 90 to access the Drug Specific App 10 in order to instruct the Drug Dispenser 230 to dispense the drug.

The system is designed to comply with the respective REMS program and to virtually eliminate required data capture and automate patient specific tracking and dispensing report preparation. The Integrated Support Center 40 will also support the Prescriber 60 by preparing the required REMS reports encompassing all his/her patients.

F. Clinical Trial

The system is designed to capture, store, analyze, and act upon drug specific patient reported self-assessment (AKA self-reported outcomes, patient-reported outcomes, PROs, etc.) and digitally captured physiological, psychological, lifestyle, other drugs currently being taken, and environmental information along with the drug's prescription and drug dispensing history in order for the Drug Specific App 10 to decide if the drug should or should not be dispensed. Dispensing can be precluded by the Drug Specific App 15 if the required dispensing criteria are not met, even if without the self assessment and digitally captured data, the prescription would normally allow dispensing.

Most of the time, clinical outcomes are held as the ultimate outcome in a clinical trial because they often provide more objective interpretation, increased reliability and greater simplicity of interpretation. However, certain disease conditions require consideration of subjective outcomes. As a result, regulatory agencies, such as the FDA, are combining patient reported outcomes (PROs) and clinical outcomes in their approval decisions. Examples include the: (i) FDA's "Guidance for Industry, Irritable Bowel Syndrome—Clinical Evaluation of Drugs for Treatment", dated May 2012 and (ii) the European Medicines Agency (EMA) "Guideline on the evaluation of medicinal products for the treatment of irritable bowel syndrome" dated April 2015. They utilize a combination of PROs and patient self-assessment reporting to measure primary and secondary endpoints required for regulatory approval of any 5HT3 drugs for irritable bowel syndrome (B S).

Interest in developing and applying patient-reported outcomes (PROs) across the drug development and postmarket spectrum is growing-among sponsors, clinicians, payers, regulators and patients. A growing number of clinical trials now are going beyond conventional randomized control measurements to collect self-reported outcomes from patients-focusing on improving patients' involvement by including their perspectives throughout the drug development process. An analysis of sponsor-funded interventional studies listed on CenterWatch's Clinical Trials Listing Service found between 2005 and 2007, only 6.1% of total study procedures involved some type of subjective outcome assessment. That grew to 11.8% in the 2008 to 2010 timeframe and, most recently, between 2011 and 2013, increased to 16.3% of total study procedures. PROs can capture a range of information, from symptom changes and level of functioning, to health-related qualify of life and treatment satisfaction and adherence.

Although their value is widely recognized, PRO use often is inconsistent and underutilized in understanding how patients feel in relation to their diseases, such as cancer, cardiovascular disease, diabetes, etc. Generally, regulatory agencies do not require sponsors to consider PROs in clinical trials and, until recently, did not do much to encourage their use. However, signs point to that sentiment is changing. Janet Woodcock, M.D., director of the FDA's Center for Drug Evaluation & Research (CDER) stated: "We understand that people with chronic diseases are experts in that disease, as far as the symptoms and the impact on quality of life, and what might be acceptable tradeoffs on risk and uncertainty. The challenge for the FDA is incorporating that knowledge in a way that accurately informs regulatory decisions." She asked, "how can we meaningfully collect that knowledge in a rigorous manner, given there's a spectrum of opinions and a spectrum of disease burden in any given disease?" PRO measurements often are used to evaluate products that treat chronic, disabling conditions, for which the goal of treatment is focused on alleviating the frequency, severity or duration of disease symptoms.

PROs generally are used as primary endpoints in clinical trials in indications such as migraines and irritable bowel syndrome, in which specific symptoms play a major role in treatment. PROs also are important in the final product labeling manufacturers are allowed to use to promote their products, and to clinicians seeking information to support their prescribing choices. Now, trials for psychiatric and age-related illnesses, among others, are including PROs as part of the protocol design.

Pain studies initially used PROs as a primary outcome in a clinical trial because attempts to obtain an objective measure of pain through a dolorimeter, a spring-loaded instrument with a gauge for measuring sensitivity to, or levels of, pain, or through a galvanic skin response lacked validity compared to simple pain scales. Other disease examples where PROs are preferable include neurology, depression, anxiety, and irritable bowel syndrome (IBS) which may utilize co-primary and/or key secondary PROs.

Keeping trial participants involved also is the hallmark of the publication and promotion of the FDA's PRO guidance at the end of 2009. In 2011, the FDA took the next step, seeking multiple ways to give the patient a clear voice in clinical research by ensuring all measurements and outcomes reflect what is happening with the patient through instruments or tools, along with PROs. Increasingly, we are seeing patients in clinical trials demanding to know what is going on and they want to be given a greater voice.

Generally, larger clinical sites can handle adding PROs more easily, while smaller sites, especially in more remote locations, can find it more challenging. Collecting data directly from the patient can provide stronger information. As an example, patients can be hesitant to report outcomes if they have been asked to take a medication a certain way and have not done so.

Furthermore, collecting data through specific data streams provides, in some cases, better quality. Patients will contact the independent group, such as the clinical trial CRO or in the embodiment, the Integrated Support Center 40 and not necessarily go back to their physicians for technical issues and concerns.

While using PROs is becoming critical in many clinical trials to prove safety and effectiveness to gain FDA approval, the next step for biopharmaceutical companies and payers will be to combine PROs with other observational studies to create real world evidence (RWE). RWE is becoming essential for sound medical coverage, payment and reimbursement decisions, according to the International Society for Pharmaeconomics Outcomes Research Real-World Data Task Force. RWE can be used with randomized clinical trials to design more efficient trials and understand a drug's benefit-risk profile, as well as to gain understanding of the market for launch planning, according to the task force. RWE shows how a drug is accepted from patients who have experience using it. It reveals how a drug is utilized in different geographies and can be used to help frame policy or regulatory decisions. It is a highly credible source of information.

The embodiment provides:" (i) the requisite data capture, (ii) patient involvement, (iii) dispensing control, (iv) avoidance of certain drug related side effects, (v) real time reminders for the patient to take the medication, (vi) intervention alerts if the patient fails to take their medication within a predefined time interval, (vii) dispensing tracking (date and time), (viii) real time monitoring, and (ix) reporting. It addresses the shortcomings of current systems to capture and compile real time, patient and drug specific data to facilitate ongoing clinical trial data aggregation, analysis, and reporting while minimizing the number of calls to the clinical trial physician.

Under the current embodiment, the patient would be prescribed the medication to be dispensed per a defined prescription using the Drug Specific App 10 controlled Drug Dispenser 30. When the Patient 50 clicks on the Drug Specific App 10 to take his/her next dose, the Drug Specific Dispensing Algorithm 15 automatically handshakes with the Drug Dispenser 30, handshakes with defined digital devices (e.g., blood pressure, heart rate, etc.) FIG. 5 and downloads the latest data to the Interface Device's 20 Drug Specific App 10 data base, checks to ensure the drug has not expired, and if it has not, then to see if it has been stored correctly. If the Drug has been stored correctly, then, for example, it automatically moves to the next screen and asks the Patient 50 to answer the specific questions. In this example, the Patient 50 would answer the PRO and data capture screens 194 to 214 required by the FDA and EMA to get approval for a 5HT3 drug to treat IBS-D. The ability to capture the requisite PRO primary and secondary end point data and the related compliance and persistence data are illustrated in FIG. 8. These screens can be configured to capture and aggregate drug specific information.

The Drug Specific Dispensing Algorithm 15 then utilizes its decision tree FIG. 6 to check the prescription instructions and when the drug was last dispensed to ascertain if the drug can be dispensed. It then either generates a screen stating that the dose will not be authorized for a specific period of time 222 or proceeds to ascertain if the designated digital and self-assessment reported values allow the medication to be dispensed. If yes, then the screen shows a green dispense 216. If the Drug Specific Dispensing Algorithm 15 indicates that the patient should not receive the medication, even if it is within the prescription guidelines, then it will either generate, for example, a screen stating that the dose is not warranted at the specific time and provide the Patient 50 the ability to click on dial to call the Integrated Support Center 40 or if a problem is ascertained, it will either show a specifically designed screen or a screen that the Integrated Support Center should be called 224. The type and sequence of screens is dictated by the drug's clinical trial data capture requirements. The algorithm can contain routines that only ask for specific information if certain predefined criteria are met.

Every non-fruitful event to dispense the medication is tracked. At a certain point the Drug Specific Dispensing Algorithm's 15 logic will send a message for the Integrated Support Center 40 to call the Patient 50.

The embodiment allows for better prescription compliance, an improved drug safety profile, increased prescription persistence, uniform data capture, facilitates data analysis, decreases required interventions by the clinical trial physician(s), decreases the cost of the trial, and provides real time data capture and analysis.

G. Intermittent Chronic Conditions

There are a number of chronic conditions that come and go and do not always require treatment. Examples include IBS, pain, allergies, arthritis, certain heart conditions, anxiety, depression, intermittent claudication, etc. The Drug Specific App 10 is capable of being programmed to control PRN dosing in various configurations and schedules. This allows for real time data capture which is useful in diagnosis, patient management, and dispensing control.

H. Revitalization of Select Drugs that Previously Failed to Get Regulatory Approval There are a myriad of drugs that failed to get regulatory approval due to dosing-related side effects. Examples include certain $5HT^3$ antagonists used to treat diarrhea predominant irritable bowel syndrome (IBS-D). Some physicians hypothesize that there is a relationship between dosing (both strength and frequency) and constipation. In turn, that constipation has a relationship with Ischemic colitis.

Patients prefer to use PRN dosing. They can take the medication when symptoms arise and continue taking it until they resolve themselves. Lostronex® (alosetron), a $5HT^3$, approved only in the United States which requires a complex REMS program, serves an example of how the Embodiment can transform drugs that failed to get approval with similar profiles into approvable agents. To lower the risk of constipation, Lostronex® should be started at a dosage of 0.5 mg twice a day. Patients who become constipated at this dosage should stop taking Lostronex® until the constipation resolves. They may be restarted at 0.5 mg once a day. If constipation recurs at the lower dose, Lostronex® should be discontinued immediately.

Patients well controlled on 0.5 mg once or twice a day may be maintained on this regimen. If after 4 weeks the dosage is well tolerated but does not adequately control IBS symptoms, then the dosage can be increased to up to 1 mg twice a day. Lostronex® should be discontinued in patients who have not had adequate control of IBS symptoms after 4 weeks of treatment with 1 mg twice a day.

Cilansetron, a more potent 5HT3 antagonist for the treatment of IBS-D failed to get FDA and European regulatory approval because of the concerns related to potential constipation that could potentially lead to ischemic colitis. The utilization of the system designed to identify and block dispensing FIG. 4 if potential constipation is suspected would address this concern. If we use the Lotronex® example, the system could also change the dosing to allow PRN dosing using, for example, 0.5 mg for up to four times per day. This would control the maximum dosing to 2 mg per day. The system would ensure compliance with the prescription and would protect against potential constipation.

What is claimed:

1. A drug dispensing system, comprising:
   (i) hardware comprising:
   (a) an interface device having a computer processor and memory storing computer code to execute a drug specific app with a plurality of modules wherein the interface device has internet communication capability and is selected from the group consisting of a smart phone, a computer, or a tablet computer wherein the smart phone, the computer or the tablet computer are in communication with a separate drug dispenser device, or wherein the interface device is a standalone tamper-resistant drug dispenser device having a computer processor and memory storing computer code to execute the drug specific app with a plurality of modules, and
   (b) at least one digital data capture device and/or at least one RFID drug chip;
   wherein the drug specific app is assigned to a specific patient;
   (ii) a biometric authentication module to authenticate the patient and to ensure digitally captured data is from the patient;
   (iii) a prescription module having a prescription for the patient;
   (iv) a patient reminder module;
   (v) an application program interface (API) (a) between the separate drug dispenser device and the smart phone, the computer or the tablet computer to link the drug dispenser device to the drug specific app, or (b) in the standalone drug dispenser device to link it to the drug specific app;
   (vi) one or more APIs between (a) the interface device and one or more digital data capture devices, and/or (b) the interface device and one or more RFID drug chips, and/or (c) the interface device and an integrated support center's servers;
   (vii) a patient self-assessment screen(s) module;

(viii) a drug specific dispensing algorithm module;
(ix) an interface device database module, comprising digitally-captured or patient-entered patient values, drug information, and dispensing-related information;
(x) a dispensing communications and reporting module;
(xi) a patient reporting module;
(xii) a security controlled drug cassette replacement module; and
(xiii) an app and dispensing unit operation training module;
wherein the system utilizes information comprising prescription information, drug dispenser device information, drug cassette information, patient self-assessment information, digitally captured physiological, psychological, and lifestyle information, information of medications administered to the patient, or environmental data information,
wherein the system captures such information before, during or after each drug dispensing and which is utilized by the drug specific diagnostic algorithm to decide if the separate or standalone drug dispenser device should dispense the drug or preclude dispensing and stay locked even in circumstances when the prescribed dose would have otherwise been allowed by the prescription, thereby preventing dose-mediated adverse events, and
wherein the drug specific diagnostic algorithm further utilizes symptom data obtained from the patient regarding the patient's symptoms and, based on the symptom data, decides if the separate or standalone drug dispenser device should dispense the drug or preclude dispensing and stay locked even in circumstances when the prescribed dose would have otherwise been allowed by the prescription, thereby preventing dose-mediated adverse events.

2. The drug dispensing system according to claim 1, wherein the symptoms analyzed by the drug specific diagnostic algorithm are selected from the group consisting of pupil size, level of pain, stool and bowel movement information, respiratory rate, blood oxygen saturation, pulse, heart rhythm, blood pressure, gait, muscle spasms, and skin temperature.

3. The drug dispensing system according to claim 2, wherein the drug cassette comprises an opioid.

4. The drug dispensing system according to claim 1, wherein the drug specific dispensing algorithm automatically handshakes with the separate or standalone drug dispenser device and the one or more digital capture devices.

5. The drug dispensing system according to claim 4, wherein the drug specific dispensing algorithm downloads data captured by the one or more digital capture devices to the interface device and then prompts the patient self-assessment module to ask the patient one or more questions about his/her condition.

6. The drug dispensing system according to claim 1, wherein the app checks a serial number of the separate or standalone drug dispenser device to ensure it is authorized to interface with the app.

7. The drug dispensing system according to claim 1, wherein the app checks the expiration date of the drug.

8. The drug dispensing system according to claim 1, wherein the app checks the storage temperature history to ensure the drug has been stored within a specific temperature range.

9. The drug dispensing system according to claim 1, wherein the app checks the storage humidity history to ensure the drug has been stored within an authorized humidity range.

10. The drug dispensing system according to claim 1, wherein the app retrieves drug information from the separate or standalone drug dispenser device.

11. The drug dispensing system according to claim 1, wherein the app is designed to receive alerts of unauthorized attempts to open the separate or standalone drug dispenser device.

12. The drug dispensing system according to claim 1, wherein the app stores a drug's prescription and dosing schedule.

13. The drug dispensing system according to claim 1, wherein the app reminds the patient to take his/her medication and after a specific period of time alerts the integrated support center and/or authorized care givers that the patient has not taken his/her medication.

14. The drug dispensing system according to claim 1, wherein the app is designed to automatically handshake with the patient's digital diagnostic, monitoring and/or tracking devices.

15. The drug dispensing system according to claim 1, wherein the app presents drug specific patient self-assessment and/or data input screen(s).

16. The drug dispensing system according to claim 1, wherein the app maintains a database of patient responses captured by self-assessment and/or data input screen(s) and digitally captured values.

17. The drug dispensing system according to claim 1, wherein the interface device is a smart phone.

18. The drug dispensing system according to claim 1, wherein the app allows the patient to click on a screen to automatically call the integrated support center.

19. The drug dispensing system according to claim 1, wherein the app records all unsuccessful attempts to dispense a dose earlier than prescribed.

20. The drug dispensing system according to claim 1, wherein the app has reporting routines that allow the patient to request certain reports created using the patient self-assessment, digital captured information, drug cassette information, and/or dosing information to ascertain if the drug is efficacious for the patient and the effect that dosing has on the patient's condition and/or symptoms.

21. The drug dispensing system according to claim 1, wherein the app effectuates a handshake with the integrated support center's computers.

22. The drug dispensing system according to claim 1, wherein the app downloads the patient's drug related dispensing information, comprising drug dispenser, patient self-assessment, or digitally captured information into the patient's records in the integrated support center's data base.

23. The drug dispensing system according to claim 1, wherein the app allows the patient to request specific drug related information stored in the app.

24. The drug dispensing system according to claim 1, wherein the app allows the patient to request specific reports or information stored on the integrated support center's servers.

25. The drug dispensing system according to claim 1, wherein the app allows the patient to correct responses entered in prior screens before dispensing the medication.

26. The drug dispensing system according to claim 1, wherein the app contains a copy of or enables access to a patient app and drug dispenser operations training and troubleshooting manual.

27. The drug dispensing system according to claim 1, wherein the app utilizes a security system to limit the ability to change the drug cassette in the drug dispenser to authorized medical professionals.

28. The drug dispensing system according to claim 1, wherein the app further comprises a GPS module to record the patient's location to ascertain where the patient is when the medication is dispensed.

* * * * *